(12) United States Patent
Mousa et al.

(10) Patent No.: US 10,328,043 B1
(45) Date of Patent: Jun. 25, 2019

(54) COMPOSITION AND METHOD FOR DUAL TARGETING IN TREATMENT OF NEUROENDOCRINE TUMORS

(71) Applicant: NANOPHARMACEUTICALS LLC, Rensselaer, NY (US)

(72) Inventors: Shaker Mousa, Wynantskill, NY (US); Mehdi Rajabi, Albany, NY (US); Ozlem O. Karakus, Glenmont, NY (US)

(73) Assignee: NANOPHARMACEUTICALS, LLC., Rensselaer, NY (US)

( * ) Notice: Subject to any disclaimer, the term of this patent is extended or adjusted under 35 U.S.C. 154(b) by 0 days.

(21) Appl. No.: 15/950,870

(22) Filed: Apr. 11, 2018

(51) Int. Cl.
| | |
|---|---|
| A61K 31/198 | (2006.01) |
| A61P 35/00 | (2006.01) |
| A61K 47/22 | (2006.01) |
| A61K 31/191 | (2006.01) |
| A61K 47/16 | (2006.01) |
| A61K 47/10 | (2017.01) |

(52) U.S. Cl.
CPC .......... A61K 31/198 (2013.01); A61K 47/22 (2013.01); A61P 35/00 (2018.01); A61K 31/191 (2013.01); A61K 47/10 (2013.01); A61K 47/16 (2013.01)

(58) Field of Classification Search
CPC ........ A61K 31/198; A61K 47/22; A61P 35/00
USPC ...................................................... 514/634
See application file for complete search history.

(56) References Cited

U.S. PATENT DOCUMENTS

| | | |
|---|---|---|
| 3,625,214 A | 12/1971 | Higuchi |
| 4,205,058 A | 5/1980 | Wagner et al. |
| 4,208,483 A | 6/1980 | Lee |
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,449,665 A | 9/1995 | Sollevi |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,733,871 A | 3/1998 | Alps et al. |
| 5,766,635 A | 6/1998 | Spenleuhauer et al. |
| 6,013,641 A | 1/2000 | Lussow et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,515,100 B2 | 2/2003 | Harris |
| 6,534,676 B2 | 3/2003 | Morkin et al. |
| 6,596,712 B2 | 7/2003 | Zasloff et al. |
| 6,677,473 B1 | 1/2004 | Madison et al. |
| 6,740,680 B1 | 5/2004 | Danforth, Jr. et al. |
| 6,818,620 B2 | 11/2004 | Bhatnagar |
| 6,821,947 B2 | 11/2004 | Renato |
| 6,936,274 B2 | 8/2005 | Hanshew, Jr. |
| 7,166,155 B2 | 1/2007 | Takeshi |
| 7,358,085 B2 | 4/2008 | Zhang et al. |
| 7,638,558 B2 | 12/2009 | Breitenkamp et al. |
| 7,785,632 B2 | 8/2010 | Mousa et al. |
| 7,807,621 B2 | 10/2010 | Mazar et al. |
| 8,026,209 B2 | 9/2011 | Gaillard et al. |
| 8,071,134 B2 | 12/2011 | Mousa et al. |
| 8,242,171 B2 | 8/2012 | Sinclair et al. |
| 8,518,451 B2 | 8/2013 | Mousa et al. |
| 8,668,926 B1 | 3/2014 | Davis et al. |
| 8,802,240 B2 | 8/2014 | Davis et al. |
| 9,180,107 B2 | 11/2015 | Mousa et al. |
| 9,198,887 B2 | 12/2015 | Mousa et al. |

(Continued)

FOREIGN PATENT DOCUMENTS

| | | |
|---|---|---|
| CA | 2673133 A1 | 11/2008 |
| CN | 1126589 | 7/1996 |

(Continued)

OTHER PUBLICATIONS

Office Action (dated Oct. 5, 2012) for U.S. Appl. No. 12/644,493, filed Dec. 22, 2009.
Office Action (dated Oct. 16, 2014) for U.S. Appl. No. 12/644,493, filed Dec. 22, 2009.
Office Action (dated Oct. 12, 2016) for U.S. Appl. No. 12/644,493, filed Dec. 22, 2009.
Office Action (dated Apr. 24, 2017) for U.S. Appl. No. 12/644,493, filed Dec. 22, 2009.
Office Action (dated Apr. 2, 2013) for U.S. Appl. No. 13/156,047, filed Jun. 8, 2011.
Office Action (dated Feb. 25, 2014) for U.S. Appl. No. 13/156,047, filed Jun. 8, 2011.
Office Action (dated Apr. 16, 2015) for U.S. Appl. No. 13/156,047, filed Jun. 8, 2011.

(Continued)

Primary Examiner — Yong L Chu
(74) Attorney, Agent, or Firm — Schmeiser, Olsen & Watts, LLP

(57) ABSTRACT

Chemical compositions and methods of synthesis thereof. The compositions disclosed and described herein are directed toward thyroid hormone αvβ3 integrin receptor antagonists conjugated to targets of the norepinephrine transporter (NET) or the catecholamine transporter. The compositions have a dual targeting effect and increased targeting efficiency in the treatment and diagnostic imaging of neuroendocrine tumors.

21 Claims, 24 Drawing Sheets
(7 of 24 Drawing Sheet(s) Filed in Color)

(56) References Cited

U.S. PATENT DOCUMENTS

| | | | |
|---|---|---|---|
| 9,220,788 B2 | 12/2015 | Davis et al. | |
| 9,272,049 B2 | 3/2016 | Alexander-Bridges et al. | |
| 9,289,395 B2 | 3/2016 | Davis et al. | |
| 9,498,536 B2 | 11/2016 | Mousa et al. | |
| 9,539,345 B2 | 1/2017 | Kim et al. | |
| 9,579,300 B2 | 2/2017 | Mousa et al. | |
| 9,750,709 B2 | 9/2017 | Mousa et al. | |
| 9,839,614 B2 | 12/2017 | Mousa et al. | |
| 2001/0021763 A1 | 9/2001 | Harris | |
| 2001/0023254 A1 | 9/2001 | McElroy | |
| 2001/0046521 A1 | 11/2001 | Zasloff et al. | |
| 2002/0049247 A1 | 4/2002 | Chen | |
| 2002/0013205 A1 | 9/2002 | Faour | |
| 2002/0137676 A1 | 9/2002 | Hsiang et al. | |
| 2002/0151594 A1 | 10/2002 | Morkin et al. | |
| 2003/0027940 A1 | 2/2003 | Lang et al. | |
| 2003/0104999 A1 | 6/2003 | Iozzo | |
| 2003/0138557 A1 | 7/2003 | Allison | |
| 2003/0143727 A1 | 7/2003 | Chang | |
| 2003/0157098 A1 | 8/2003 | Laug | |
| 2003/0162758 A1 | 8/2003 | Schwartz et al. | |
| 2003/0165576 A1 | 9/2003 | Fujii et al. | |
| 2004/0013728 A1 | 1/2004 | Oh et al. | |
| 2004/0033259 A1 | 2/2004 | Hanshew, Jr. et al. | |
| 2004/0208844 A1 | 10/2004 | Ignatious | |
| 2004/0219668 A1 | 11/2004 | Frei et al. | |
| 2005/0124862 A1 | 6/2005 | Mousa et al. | |
| 2005/0158376 A1 | 7/2005 | Sardi et al. | |
| 2005/0171027 A1 | 8/2005 | Sinclair et al. | |
| 2005/0222387 A1 | 10/2005 | Debatin et al. | |
| 2005/0249721 A1 | 11/2005 | Houston et al. | |
| 2005/0266393 A1 | 12/2005 | Baxter et al. | |
| 2005/0272817 A1 | 12/2005 | Heino | |
| 2006/0166303 A1 | 7/2006 | Spanuth | |
| 2006/0210539 A1 | 9/2006 | Zhang | |
| 2006/0216251 A1 | 9/2006 | Morariu | |
| 2007/0117841 A1 | 5/2007 | Ozes et al. | |
| 2007/0190160 A1 | 8/2007 | Turos et al. | |
| 2008/0081074 A1 | 4/2008 | Gu et al. | |
| 2008/0124280 A1 | 5/2008 | Mousa et al. | |
| 2008/0193377 A1 | 8/2008 | Line et al. | |
| 2008/0199850 A1 | 8/2008 | Sutter et al. | |
| 2009/0022806 A1 | 1/2009 | Mousa et al. | |
| 2009/0175862 A1 | 7/2009 | Silverio et al. | |
| 2009/0197240 A1 | 8/2009 | Fishman et al. | |
| 2010/0159021 A1 | 6/2010 | Davis et al. | |
| 2010/0209382 A1 | 8/2010 | Alexander-Bridges et al. | |
| 2010/0255108 A1* | 10/2010 | Lin | A61K 31/192 424/491 |
| 2011/0052715 A1 | 3/2011 | Davis et al. | |
| 2011/0112079 A1 | 5/2011 | Mousa et al. | |
| 2011/0142941 A1 | 6/2011 | Davis et al. | |
| 2012/0258069 A1 | 10/2012 | Alexander-Bridges et al. | |
| 2012/0315320 A1 | 12/2012 | Davis et al. | |
| 2013/0224115 A1* | 8/2013 | Wang | A61K 49/0032 424/9.1 |
| 2014/0744646 | 2/2014 | Li et al. | |
| 2014/0072635 A1 | 3/2014 | Mousa et al. | |
| 2014/0072646 A1 | 3/2014 | Mousa et al. | |
| 2014/0170066 A1 | 6/2014 | Rajopadhye et al. | |
| 2014/0199375 A1 | 7/2014 | Mousa et al. | |
| 2014/0294931 A1 | 10/2014 | Mousa et al. | |
| 2015/0139934 A1 | 5/2015 | Mousa et al. | |
| 2015/0238631 A1 | 8/2015 | Kim et al. | |
| 2016/0178615 A1 | 6/2016 | Alexander-Bridges et al. | |
| 2016/0348052 A1 | 12/2016 | Lin et al. | |
| 2017/0080058 A1 | 3/2017 | Mousa et al. | |
| 2017/0348425 A1* | 12/2017 | Mousa | A61K 47/545 |
| 2017/0348428 A1 | 12/2017 | Mousa et al. | |

FOREIGN PATENT DOCUMENTS

| | | |
|---|---|---|
| KR | 100830889 B1 | 5/2008 |
| WO | 95/00135 | 1/1995 |
| WO | 96/40048 | 12/1996 |
| WO | 98/33942 | 8/1998 |
| WO | 98/56771 | 12/1998 |
| WO | 99/58119 A1 | 11/1999 |
| WO | 99/59548 A1 | 11/1999 |
| WO | 99/62549 | 12/1999 |
| WO | 0064431 A1 | 11/2000 |
| WO | 0078815 A1 | 12/2000 |
| WO | 01/133031 A1 | 2/2001 |
| WO | 01/13936 A1 | 3/2001 |
| WO | 01/76589 A1 | 10/2001 |
| WO | 02/03914 A2 | 1/2002 |
| WO | 02/49501 A2 | 6/2002 |
| WO | 2002/060389 A2 | 8/2002 |
| WO | 03/75741 A2 | 9/2003 |
| WO | 2004/013728 A2 | 2/2004 |
| WO | 2004/069201 A2 | 8/2004 |
| WO | 2005/027895 A2 | 3/2005 |
| WO | 2006/003014 A2 | 1/2006 |
| WO | 2006/031922 A2 | 3/2006 |
| WO | 2007/035612 A2 | 3/2007 |
| WO | 2008/051291 A2 | 5/2008 |
| WO | 2008/140507 A2 | 11/2008 |
| WO | 2010075332 A1 | 7/2010 |
| WO | 2010/120506 A1 | 10/2010 |
| WO | 2010/148007 A1 | 12/2010 |

OTHER PUBLICATIONS

Notice of Allowance (dated Nov. 2, 2015) for U.S. Appl. No. 13/156,047, filed Jun. 8, 2011.
Office Action (dated Oct. 14, 2014) for U.S. Appl. No. 14/242,041, filed Apr. 2, 2014.
Office Action (dated Jun. 11, 2015) for U.S. Appl. No. 14/242,041, filed Apr. 1, 2014.
Final Office Action (dated Oct. 16, 2015) for U.S. Appl. No. 14/242,041, filed Apr. 1, 2014.
Advisory Action (dated Jan. 21, 2016) for U.S. Appl. No. 14/242,041, filed Apr. 1, 2014.
Office Action (dated May 26, 2016) for U.S. Appl. No. 14/242,041, filed Apr. 2, 2014.
Notice of Allowance (dated Jul. 19, 2016) for U.S. Appl. No. 14/242,041, filed Apr. 1, 2014.
Office Action (dated Dec. 29, 2017) for U.S. Appl. No. 15/357,818, filed Nov. 21, 2016.
Office Action (dated Apr. 20, 2018) for U.S. Appl. No. 15/357,818, filed Nov. 21, 2016.
Notice of Allowance (dated Jul. 3, 2018) for U.S. Appl. No. 15/357,818, filed Nov. 21, 2016.
Restriction Requirement (dated Nov. 4, 2015) for U.S. Appl. No. 15/546,440, filed Nov. 18, 2014.
Office Action (dated Mar. 24, 2016) for U.S. Appl. No. 15/546,440, filed Nov. 18, 2014.
Office Action (dated Sep. 30, 2016) for U.S. Appl. No. 15/546,440, filed Nov. 18, 2014.
Office Action (dated Oct. 4, 2017) for U.S. Appl. No. 15/546,440, filed Nov. 18, 2014.
Notice of Allowance (dated May 3, 2018) for U.S. Appl. No. 15/546,440, filed Nov. 18, 2014.
Restriction Requirement (dated Feb. 9, 2017) for U.S. Appl. No. 15/056,522, filed Feb. 29, 2016.
Office Action (dated Jun. 13, 2018) for U.S. Appl. No. 15/056,522, filed Feb. 29, 2016.
Office Action (dated Jun. 11, 2018) for U.S. Appl. No. 14/903,149, filed Jan. 6, 2016.
Office Action (dated May 10, 2018) for U.S. Appl. No. 15/616,637, filed Jun. 7, 2017.
Notice of Allowance (dated Jul. 25, 2018) for U.S. Appl. No. 15/616,637, filed Jun. 7, 2017.
European Patent Application No. 10 790 068.0, Office Action dated Jul. 11, 2018. 4 pages.
A.D.A.M. Medical Encyclopedia, www.ncbi.nlm.nih.gov/pubmedhealth/PMH0001308/ , downloaded Jul. 12, 2012 6 pages.
Abdollahi et al., "Inhibition of αvβ3 Integrin Survival Signaling Enhances Antiangiogenic and Antitumor Effects of Radiotherapy", Clin. Cancer Research., 11(17):6270-6279 (2005) 10 pages.

(56) References Cited

OTHER PUBLICATIONS

Albert et al., "Integrin αvβ3 Antagonist Cilengitide Enhances Efficacy of Radiotherapy in Endothelial Cell and Non-Small-Cell Lung Cancer Models", Int. J. Radial Oncol. Biol. Phys., 65(5):1536-1543 (2006) 8 pages.
Alexis et al., "Nonocclusive Common Carotid Artery Thrombosis in the Rat Results in Reversible Sensorimotor and Cognitive Behavorial Deficits", Stroke, 26:2338-2346 (1995) 16 pages.
Ali et al., "Angiogenesis as a potential biomarker in prostate cancer chemoprevention trials", Urology, 57(Suppl 4A):143-147 (2001) 5 pages.
Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.
Ali et al., "High levels of oestrogen receptor-α in tumorigenesis: inhibition of cell growth and angiogenic factors", Cell Prolit, 34(4):223-231 (2001) 10 pages.
Allen, A.R., "Surgery of experimental lesion of spinal cord equivalent to crush injury of fracture dislocation of spinal column", J. Am. Med. Assoc., 57(11):878-880 (1911) 4 pages.
Almog et al., "Transcriptional Switch of Dormant Tumors to Fast-Growing Angiogenic Phenotype", Cancer Res., 69(3):836-844 (2009).
Amirkhosravi et al., "Antimetastatic effect of tinzaparin, a low-molecular-weight heparin", J. Thromb. Haemost., 1:1972-1976 (2003) 5 pages.
Amirkhosravi et al., "Inhibition of tumor cell-induced platelet aggregation and lung metastasis by the oral GpIIb/IIIa antagonist XV454", J. Thrombosis and Haemostasis, 3:549-554 (2003) 6 pages.
Ando et al., "Induction by carbon-ion irradiation of the expression of vascular endothelial growth factor in lung carcinoma cells", Int. J. Radiat. Biol., 76(8):1121-1127 (2000) 7 pages.
Application No. PCT/US2004/030583, International Search Report and the Written Opinion of the International Searching Authority, or the Declaration dated Mar. 7, 2005. 11 pages.
Application No. PCT/US2005/032813, International Search Report dated Dec. 22, 2006. 6 pages.
Application No. PCT/US2007/009026, International Search Report dated Nov. 7, 2008. 5 pages.
Application No. PCT/US2009/069104, International Search Report dated Mar. 4, 2010 5 pages.
Application No. PCT/US2007/026167, International Search Report dated Oct. 30, 2008. 3 pages.
Application No. PCT/US2010/038700, Supplemental European Search Report dated Apr. 20, 2015. 7 pages.
Application No. PCT/US2010/038700, International Search Report dated Mar. 21, 2011. 4 pages.
Application No. PCT/US2006/036243, International Search Report dated Jul. 30, 2007. 7 pages.
Application No. PCT/US2010/029371, International Search Report dated Aug. 24, 2010. 5 pages.
Audus et al., "Bovine Brain Microvessel Endothelial Cell Monolayers as a Model System for the Blood-Brain Barrier", in Biological Approaches to the Controlled Delivery of Drugs, Ann. N.Y. Acad. Sci., 507:9-18 (1987) 11 pages.
Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.
Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.
Baur et al., "Resveratrol improves health and survival of mice on a high-calorie diet", Nature, 444:337-342 (2006) 6 pages.

Baur et al., "Therapeutic potential of resveratrol: the in vivo evidence", Nat. Rev. Drug Discov., 5:493-506 (2006) 14 pages.
Bederson et al., "Rat Middle Cerebral Artery Occlusion: Evaluation of the Model and Development of a Neurologic Examination", Stroke, 17(3):472-476 (1986) 6 pages.
BelenIcy et al., "NAD+ metabolism in health and disease", Trends Biochem. Sci., 32(1):12-19 (2007) 9 pages.
Application No. PCT/US2017/36396, International Search Report dated Jun. 7, 2017.
Application No. PCT/US2014/66154, International Search Report dated Jan. 27, 2015. 12 pages.
Gu et al. 2007, Nanotoday 2:14-21.
Wood, J., et al. "Novel Antiangiogenic Effects of the u Bisphosphonate Compound Zoledronic Acid." The Journal of Pharmacology and Experimental Therapeutics, vol. 302, No. 3, 2002, pp. 1055-1061.
Park, T.G., "Bioconjugation of Biodegradable Poly (lactic'glycolic acid) to Protein, Peptide, and Anti-Cancer Drug: An Alternative Pathway for Achieving Controlled Release from Micro- and Nanoparticles." in Polymeric Drugs and Drug Delivery Systems, Ottenbrite R.M. and Kim S.W., eds., Ch. 7, pp. 101-114 (2001).
Oh, Jong Eun, et al., "Conjugation of drug to poly (D,L-lacitic-co-glycoli acid) for controlled release from biodegradable microspheres." Journal of Controlled Release 57, 269-280 (1999).
Ditsch, Nina, et al., "Thyroid Function in Breast Cancer Patients." Anticancer Research 30: 1713-1718 (2010).
Webmd.com (http://www.webmd.com/women/news/20030410/underactive-thyroid-lowers-breast-cancer). Dated Apr. 10, 2003.
Mousa, Shaker A., et al., "Tetraiodothyroacetic acid and its nanoformulation inhibit thyroid hormone stimulation of non-small cell lung cancer cells in vitro and its growth in xenografts." Lung Cancer 76; 39-45 (2012).
Leuthy,A.; et al. "autologous stem cell transplantation: leukapheresis product has anti-angiogenic effects in vivo correlating with neutrophil-derived VEGFR1" Anticancer Research, 2001, v.31, 9.3115-3124.
Mythyroid.com. "Blood tests" (Http://222.mythyroid.com/bloodtests.html) cached 2005 wayback machine.
Huang, Kuo-Shiang, et al. "Combination of Baculovirus-Mediated Gene Delivery and Packed-Bed Reactor for Scalable Production of Adeno-Associated Virus", Human Gene Therapy, Mary Ann Liebert, Inc., Publishers, US., vol. 18, No. 11. 2007, pp. 1161-1170.
Lin, Hung-Yun, et al. "Pharmacodynamic Modeling of Anti-Cancer Activity of Tetraiodotheyroacetic Acid in a Perfused Cell Culture System" Plos Computational Biology, vol. 7, N.2, 2011, p. e1001073.
European Examination Report for EP Application No. 07867073.4, dated Jul. 16, 2015.
Veronese, "Peptide and protein PEGylation: a review of problems and solutions" Biomaterials 22 (2001) 405-417.
Oshaghi, Ebrahim Abbasi, et al., "Role of resveratrol in the management of insulin resistance and related conditions: Mechanism of action," Critical Reviews in Clinical Laboratory Sciences, 2017. vol. 54, No. 4, pp. 27-293.
Mayo Clinic, "Multiple sclerosis—Diagnosis and treatment," URL: https://www.mayoclinic.org/diseases-conditions/multiple-sclerosis/diagnosis-treatment/drc-20350274 accessed Dec. 21, 217, 12 printed pages. (Year: 2017).
Susman, E., "Beware of Non-Aspirin NSAIDs for Kidney Cancer Patients." Genitourinary Cancers Symposium, oncology-times.com, 2016, p. 21. (Year: 2016).
Lane, N.E., et al., "Osteoarthritis year in review 2016: clinical," Osteoarthritis and Cartilage, vol. 25, 2017, pp. 209-215 (Year: 2017).
*Kennecott Corporation*, Plaintiff-Appellant v. *Kyocera International, Inc.*, and *Kyoto Ceramic Co., Ltd.*, Defendant-Appellee. Case Decided Dec. 22, 1987. (https://law.resource.org/pub/us/case/reporterF2/835/835.F2d.1419.871151.html), accessed Jan. 15, 2016, 5 printed pages.
Application No. PCT/US11/043837, International Preliminary Report on Patentability dated Jan. 15, 2013. 5 pages.
Tetraiodothyroacetic Acid-Tagged Liposomes for Enhanced Delivery of Anticancer Drug to Tumor Tissue via Integrin Receptor http://www.sciencedirect.com/sciencearticle/pii/S0168365912004567.

(56) References Cited

OTHER PUBLICATIONS

64Cu-Labeled Tetraiodothyroacetic Acid-Conjugated Liposomes for PET Imaging of Tumor Angiogenesis http://www.sciencedirect.con/science/article/pii/S969805113001704.
Office Action (dated Jun. 21, 2011) for U.S. Appl. No. 12/947,389, filed Nov. 16, 2010.
Office Action (dated Apr. 4, 2012) for U.S. Appl. No. 12/947,389, filed Nov. 16, 2010.
Office Action (dated Oct. 17, 2012) for U.S. Appl. No. 12/947,389, filed Nov. 16, 2010.
Office Action (dated Mar. 12, 2014) for U.S. Appl. No. 12/947,389, filed Nov. 16, 2010.
Office Action (dated Sep. 4, 2014) for U.S. Appl. No. 12/947,389, filed Nov. 16, 2010.
Notice of Allowance (dated Nov. 16, 2015) for U.S. Appl. No. 12/947,389, filed Nov. 16, 2010.
Office Action (dated May 23, 2012) for U.S. Appl. No. 12/816,287, filed Jun. 15, 2010.
Office Action (dated Apr. 11, 2013) for U.S. Appl. No. 12/816,287, filed Jun. 15, 2010.
Office Action (dated Oct. 24, 2013) for U.S. Appl. No. 12/816,287, filed Jun. 15, 2010.
Office Action (dated May 8, 2014) for U.S. Appl. No. 12/816,287, filed Jun. 15, 2010.
Notice of Allowance (dated May 12, 2015) for U.S. Appl. No. 12/816,287.
Restriction Requirement (dated May 5, 2016) for U.S. Appl. No. 14/977,776.
Office Action (dated Nov. 4, 2016) for U.S. Appl. No. 14/977,776.
Office Action (dated Apr. 8, 2013) for U.S. Appl. No. 11/786,723, filed Apr. 11, 2007.
Restriction Requirement (dated Dec. 3, 2015) for U.S. Appl. No. 14/184,889, filed Feb. 20, 2014.
Office Action (dated May 6, 2016) for U.S. Appl. No. 14/184,889, filed Feb. 20, 2014.
Notice of Allowance (dated Oct. 13, 2016) for U.S. Appl. No. 14/184,889, filed Feb. 20, 2014.
Restriction Requirement (dated Dec. 2, 2015) for U.S. Appl. No. 14/184,889, filed Feb. 20, 2014.
Office Action (dated Sep. 9, 2016) for U.S. Appl. No. 14/185,010, filed Feb. 20, 2014.
Notice of Allowance for U.S. Appl. No. 14/185,010 (dated Apr. 4, 2017).
Office Action (dated May 12, 2015) for U.S. Appl. No. 14/078,713, filed Nov. 13, 2013.
Notice of Allowance (dated Aug. 3, 2015) for U.S. Appl. No. 14/078,713, filed Nov. 13, 2013.
Office Action (dated Mar. 24, 2015) for U.S. Appl. No. 13/975,725, filed Aug. 26, 2013.
Final Office Action (dated Oct. 9, 2015) for U.S. Appl. No. 13/975,725, filed Aug. 26, 2013.
Advisory Action (dated Dec. 31, 2015) for U.S. Appl. No. 13/975,725, filed Aug. 26, 2013.
Office Action (dated Jun. 17, 2016) for U.S. Appl. No. 13/975,725, filed Aug. 26, 2013.
Final Office Action (dated Apr. 3, 2017) for U.S. Appl. No. 13/975,725, filed Aug. 26, 2013.
Notice of Allowance (dated Jan. 31, 2018 for U.S. Appl. No. 13/975,725, filed Aug. 26, 2013.
Strieth, et al., "Antiangiogenic combination tumor therapy blocking αv-integrins and VEGF-receptor-2 increases therapeutic effects in vivo", Int. J. Cancer, 119:423-431 (2006) 9 pages.
Sumi et al., "Wound healing using regenerative medicine", Surg. Front., 10(2):162-165 (2003) 4 pages.
Sunwoo et al., "Novel Proteasome Inhibitor PS-341 Inhibits Activation of Nuclear Factor-κB, Cell Survival, Tumor Growth, and Angiogenesis in Squamous Cell Carcinoma", Clin. Cancer Res., 7:1419-1428 (2001) 10 pages.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.
Szatmari et al., "Detailed characterization of the mouse glioma 261 tumor model for experimental glioblastoma therapy", Cancer Sci., 97(6):546-553 (2006) 8 pages.
Szumiel, I., "Ca2+, Mg2+ and (Adenosine Diphosphate Ribose)n In Cellular Response to Irradiation", J. Theor. Biol., 101:441-451 (1983) 11 pages.
Takemaru et al., "Chibby, a nuclear β-catenin-associated antagonist of the Wnt/Wingless pathway", Nature, 422:905-909 (2003) 5 pages.
Tanaka et al., J. Soc. Gastroenterological Surgery, 27(2):360 (1996) 3 pages.
Tang et al., "Resveratrol-induced Cyclooxygenase-2 facilitates p53-dependent apoptosis in human breast cancer cells", Mol. Cancer Ther., 5(8):2034-2042 (2006) 9 pages.
Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.
Tator et al., "Review of the secondary injury theory of acute spinal cord trauma with emphasis on vascular mechanisms", J. Neurosurg., 75(1):15-26 (1991) 13 pages.
Theodossiou et al., "Propylthiouracil-induced Hypothyroidism Reduces Xenograft Tumor Growth in Athymic Nude Mice", Cancer, 86:1596-1601 (1999) 6 pages.
Thompson et al., "The Clinical Manipulation of Angiogenesis: Pathology, Side-Effects, Surprises, and Opportunites with Novel Human Therapies." J. Pathol. 190(2000):330-337 8 pages.
Thraves et al., "Radiosensitization of Human Fibroblasts by 3-Aminobenzamide: An Inhibitor of Poly(ADP-Ribosylation)", Radiat Res., 104:119-127 (1985) 9 pages.
Tol et al., "Chemotherapy, Bevacizumab, and Cetuximab in Metastatic Colorectal Cancer", N. Engl. J. Med., 360(6):563-572 (2009) 10 pages.
Tomanek et al., "A Thyroid Hormone Analog Stimulates Angiogenesis in the Post-infarcted Rat Heart", J. Mol. Cell Cardiol., 30(5):923-932 (1998) 10 pages.
Tomanek et al., "Angiogenesis: New Insights and Therapeutic Potential", Anatomical Record (New Anat.), 261:126-135 (2000) 10 pages.
Tomanek et al., "Early Coronary Angiogenesis in Response to Thyroxine: Growth Characteristics and Upregulation of Basic Fibroblast Growth Factor", Circ. Res., 82(5):587-593 (1998) 8 pages.
Tomanek et al., "Growth of the Coronary Vasculature in Hypertrophy: Mechanisms and Model Dependence", Cell. Mol. Bio. Res., 40(2):129-136 (1994) 8 pages.
Toms et al., "Thyroid Hormone Depletion Inhibits Astrocytoma Proliferation via a p53-Independent Induction of p21 (WAF/1CIP1)", Anticancer Res., 18:289-293 (1998) 5 pages.
Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages.
Tzirogiannis et al., "Enhanced Proliferation of Human Lung Adenocarcinoma and Small Cell Lung Carcinoma Cells Directed from the Cell Surface by Thyroid Hormone", in 89th Annual Meeting, the Endocrine Society (2007) Abstract Only 3 pages.
Utsumi et al., "Potentially Lethal Damage Versus Sublethal Damage: Independent Repair Processes in Actively Growing Chinese Hamster Cells", Radiat. Res., 77:346-360 (1979) 9 pages.
Van Waes et al., "Effects of the novel αv integrin antagonist SM256 and cis-platinum on growth of murine squamous cell carcinoma PAM LY8", Int. J. Oncol., 16(6):1189-1195 (2000) 8 pages.
VanCutsem et al., "Cetuximab and Chemotherapy as Initial Treatment for Metastatic Colorectal Cancer", N. Engl. J. Med., 360:1408-1417 (2009) 10 pages.
Vames et al., "The Effect of pH on Potentially Lethal Damage Recovery in A549 Cells", Radiat. Res., 108:80-90 (1986) 11 pages.
Velasco et al., "Dermatological Aspects of Angiogenesis." Brit. J. Dermatol. 147(2002):841-852 12 pages.
Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages.

(56) References Cited

OTHER PUBLICATIONS

Wang et al., "Integrin-associated Protein Stimulates α2β1-dependent Chemotaxis via Gi-mediated inhibition of Adenylate Cyclase and Extracellular-regulated Kinases", J. Cell. Biol., 147:389-399 (1999) 11 pages.

Wen et al., "Prognostic Value of EGFR and TGF-α in Early Laryngeal Cancer Treated With Radiotherapy", Laryngoscope, 106(7):884-888 (1996) 6 pages.

Werdelin et al., "Neuropeptides and neural cell adhesion molecule (NCAM) in CSF from patients with ALS", Acta Neurol. Scand., 79(3):177-181 (1989).

Wilkinson, J.H., "Synthesis of some Possible Metabolites of Thyroxine and Triiodothyronine", Biochem. J., 63:601-605 (1956) 5 pages.

Xia et al., "Chemokines/chemokine receptors in the central nervous system and Alzheimer's disease", J. NeuroVirol. 5:32-41 (1999) 11 pages.

Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.

Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.

Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.

Yanase et al., "Role of N-methyl-D-aspartate receptor in acute spinal cord injury", J. Neurosurg., 83:884-888 (1995) 6 pages.

Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.

Yang, et al., "Enhanced inhibition of adipogenesis and induction of apoptosis in 3T3-L1 adipocytes with combinations of resveratrol and quercetin", Life Sci., 82:1032-1039 (2008) 8 pages.

Yonkers et al., "Sensory Neuron Sodium Current Requires Nongenomic Actions of Thyroid Hormone During Development", J. Neurophysiol., 100:2719-2725 (2008) 7 pages.

Young, W., "Role of Calcium in Central Nervous System Injuries", J. Neurotrauma, 9(Suppl. 1): S9-S25 (1992) 18 pages.

Young, W, "Secondary injury mechanisms in acute spinal cord injury", J. Emerg. Med., 11:13-22 (1993) 11 pages.

Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.

Yu, et al., "The Compressor Silencing Mediator for Retinoid and Thyroid Hormone Receptor Facilitates Cellular Recovery from DNA Double-Strand Breaks", Cancer Res., 66(18):9316-9322 (2006) 7 pages.

Zhang et al., "Oestrogen inhibits resveratrol-induced post-translational modification of p53 and apoptosis in breast cancer cells", Br. J. Cancer, 91:178-185 (2004) 8 pages.

Zhang et al., "Quantitative PET Imaging of Tumor Integrin αvβ3 Expression with 18F-FRGD2", J. Nucl. Med., 47:113-121 (2006) 9 pages.

Zhen et al., "Synthesis and Amyloid Binding Properties of Rhenium Complexes: Preliminary Progress Toward a Reagent for SPECT Imaging of Alzheimer's Disease Brain", J. Med. Chem., 42:2805-2815 (1999) 11 pages.

Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.

Avgoustakis, et al., "PLGA-mPEG nanoparticles of cisplatin: in vitro nanoparticle degradation, in vitro drug release and in vivo drug residence in blood properties" J. Contr. Rel. 2002, 79, 123-135. 13 pages.

NCI Cancer Drug Information, Cetuximab, 2006,http://www.cancer.gov/cancertopics/druginfo/cetuximab,downloaded Jul. 18, 2014.

Goodman, M.M., "Automated Synthesis of Radiotracers for PET Applications", in Clinical Positron Emission Tomography, Mosby Yearbook, K.F. Hubner et al., Chapter 14, pp. 110-122 (1992) 13 pages.

Grant, D.B. "Monitoring TSH concentrations during treatment for congenital hypothyroidism", Arch. Disease Childhood, 66:669-670 (1991) 2 pages.

Gregoriadis, "Liposomes", in Drug Carriers in Biology and Medicine, Chapter 14, pp. 287-341, Academic Press (1979) 57 pages.

Guigon et al., "Regulation of β-Catenin by a Novel Nongenomic Action of Thyroid Hormone β Receptor", Mol. Cell. Biol., 28(14):4598-4608 (2008) 11 pages.

Hahn et al., "Plateau-phase cultures of mammalian cells: An in vitro model for human cancer", Curr. Top. Radiat. Res. Q., 8:39-83 (1972) 45 pages.

Halks-Miller et al., "CCR1 Immunoreactivity in Alzheimer's Disease Brains", Society for Neuroscience Meeting, Abstract #787.6, vol. 24 (1998) Abstract Only. 1 page.

Hansebout, R.R., "A Comprehensive Review of Methods of Improving Cord Recovery After Acute Spinal Cord Injury", in Early Management of Acute Spinal Cord Injury, pp. 181-196 (1982) 16 pages.

Hartert, H., "Blutgerinnungsstud Mit Der Thrombelastogeraphie, Einem Neuen Untersuchungsverfahren", Klinische Wochenschrift 26(37138):577-583 (1948) German Language Only. 9 pages.

Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.

Heller et al., "Inhibition of potentially lethal damage recovery by altered pH, glucose utilization and proliferation in plateau growth phase human glioma cells", Int. J. Radiat. Biol., 66(1):41-47 (1994) 7 pages.

Hercbergs et al., "GL261 brain tumor cells: responses to single or fractionated x-irradiation with the αvβ3 integrin thyroxine receptor antagonist tetrac (tetraiodothyroacetic acid)", 20th EORTC-NCI-AACR Symposium on Molecular Targets and Cancer Therapeutics, Geneva, Switzerland, Oct. 2008.

Hercbergs et al., "GL261 brain tumor cells: responses to single or fractionated x-irradiation with the αvβ3 integrin thyroxine receptor antagonist tetrac (tetraiodothyroacetic acid)", Euro. J. Cancer, 6(12):172 (Abstract Only) 4 pages.

Hercbergs et al., "Propylthiouracil-induced Chemical Hypothyroidism with High-Dose Tamoxifen Prolongs Survival in Recurrent High Grade Glioma: A Phase I/II Study", Anticancer Res., 23:617-626 (2003) 10 pages.

Hercbergs, A., "The Thyroid Gland as an Intrinsic Biologic Response-Modifier in Advanced Neoplasia—A Novel Paradigm", in vivo, 10:"245-247 (1996) 3 pages.

Hercbergs, et al., GL261 Brain Tumor Cells: In Vitro Single and Fractionated Dose Responses to X-Rays and Modification by Tetrac (Tetraiodothyroacetic Acid), The Cleveland Clinic Foundation, Department of Radiation Oncology 46 pages.

Hercbergs, et al., "Radiosensitization of GL261 glioma cells by tetraiodothyroacetic acid (tetrac)", Cell Cycle, 8(16):2586-2591 (2009) 6 pages.

Hermanson, "Modification with Synthetic Polymers", in Bioconjugate Tech., Ch. 15, Academic Press, San Diego, CA, pp. 617-618 (1996) 4 pages.

Hoff et al., "Medullary Thyroid Carcinoma", Hematol. Oncol. Cin. North Am., 21(3):475-488 (2007) 14 pages.

Horuk et al., "Expression of Chemokine Receptors by Subsets of Neurons in the Central Nervous System", J. Immunol., 158:2882-2890 (1997) 9 pages.

Hubner, K.F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages.

Hudlicka et al., "Factors involved in capillary growth in the heart", Mol. Cell. Biochem, 147:57-68 (1995) 12 pages.

Igarashi et al., "Techniques Supporting Angiogenesis Therapy 2: DDS Technique Supporting Regenerative Medicine." Inflamm. Immun. 10.6(2002):652-658 7 pages.

(56) References Cited

OTHER PUBLICATIONS

Illario et al., "Fibronectin-Induced Proliferation in Thyroid Cells is Mediated by αvβ3 Integrin through Ras/Raf-1/MEK/ERK and Calcium/CaMKII Signals", J. Clin. Endocrinol. Metab., 90(5):2865-2873 (2005) 9 pages.
Ingerman-Wojenski et al., "Evaluation of electrical aggregometry: comparison with optical aggregometry, secretion of ATP, and accumulation of radiolabeled platelets", J. Lab. Clin. Med., 101(1):44-52 (1983) 10 pages.
Iwata et al., "A new, convenient method for the preparation of 4-[18F]fluorobenzyl halides", Applied Radiation and Isotopes, 52(1):87-92 (2000) 7 pages.
Jain, K.K., "Strategies and technologies for drug delivery systems", TIPS, 19:155-157 (1998) 5 pages.
Janssen et al., "Pathogenesis of Spinal Cord Injury and Newer Treatments—A Review", Spine, 14(1):23-32 (1989) 11 pages.
Jeffrey et al., "The preparation and characterisation of poly(lactide-co-glycolide) microparticles. 1. Oil-in-water emulsion solvent evaporation", Int. J. Pharm., 77:169-175 (1991) 7 pages.
Jonker et al., "Cetuximab for the Treatment of Colorectal Cancer", N. Engl. J. Med., 357(20):2040-2048 (2007) 9 pages.
Jordan et al., "Thyroid Status is a Key Modulator of Tumor Oxygenation: Implication for Radiation Therapy", Radiat. Res., 168:428-432 (2007) 5 pages.
Kalofonos et al., "Monoclonal Antibodies in the Management of Solid Tumors", Curr. Top. Med. Chem., 6:1687-1705 (2006)19 pages.
Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.
Kastan et al., "A Mammalian Cell Cycle Checkpoint Pathway Utliziing P53 and GADD45 is Defective in Ataxia-Telangiectasia", Cell. 71:587-597 (1992) 11 pages.
Kawasuji et al., Jap. Circ. J., 63(Suppl. 1):65 (1999) Japanese Abstract Only. 3 pages.
Kerr et al., "Novel Small Molecule αv Integrin Antagonists: Comparative Anti-Cancer Efficacy with Known Angiogenesis Inhibitors", Anticancer Res., 19:959-968 (1999).
Kerr et al., "Small molecule αv integrin antagonists: novel anticancer agents", Exp. Opin. Invest. Drugs, 9(6):1271-1279 (2000) 9 pages.
Kim et al., "Regulation of Angiogenesis in Vivo, by Ligation of Integrin α5β1 with the Central Cell-Binding Domain of Fibronectin", Am. J. Pathol., 156(4): 1345-1362 (2000) 18 pages.
Kim et al., "Soluble Flt-1 gene delivery using PEI-g-PEG-RGD conjugate for anti-angiogenesis", J. Control Release, 38 106:224-234 (2005) 11 pages.
Kimelberg, H.K., "Astrocytic Edema in CNS Trauma", J. Neurotrauma, 9(Suppl. 1):S71-S81 (1992) 12 pages.
Kitevska et al., "Caspase-2: controversial killer or checkpoint controller?", Apoptosis, 14:829-848(2009) 20 pages.
Kleczkowska et al., "Differential poly(ADP-ribose) metabolism in repair-proficient and repair-deficient murine lymphoma cells", Mut. Res., 235:93-99 (1990) 7 pages.
Klunk et al., "Development of Small Molecule Probes for the Beta-Amyloid Protein of Alzheimer's Disease", Neurobiol. Aging, 15(6):691-698 (1994) 8 pages.
Kobayashi et al., "Drug Delivery Catheter." Surg. Front. 9.1(2002):55-57 3 pages.
Konno et al., "Antiogenetic therapy for carcinoma", Igaku No Ayumi, 194(10): 824-828 (2000) 5 pages.
Koutras et al., "Antiproliferative effect of exemestane in lung cancer cells", Mol. Cancer, 8(1):109 (2009) 12 pages.
Koyama et al., "Recent Status and Future Perspectives in Therapeutic Angiogenesis", Prog. Med., 22(12):3070-3076 (2002) (English Abstract) 7 pages.
Kramer et al., "Human Microvascular Endothelial Cells Use β1 and β3 Integrin Receptor Complexes to Attach to Laminin", J. Cell Biol., 111:1233-1343 (1990) 11 pages.

Kumar et al., "Enhancing Effect of Thyroxine on Tumor Growth and Metastases in Syngeneic Mouse Tumor Systems", Cancer Res., 39:3515-3518 (1979) 4 pages.
Kuroki et al., "Diabetic retinopathy—The mechanisms of the ocular neovascularization of the development of antiangiogenic drugs-", Nippon Rinsho, 57(3):584-589 (1999) (English Abstract Only) 6 pages.
Kwok et al., "Differences in EGF rated radiosensitisation of human squamous carcinoma cells with high and low numbers of EGF receptors", Br. J. Cancer, 64:251-254 (1991) 4 pages.
Lameloise et al., "Differences between the effects of thyroxine and tetraiodothyroacetic acid on TSH suppression and cardiac hypertrophy", Eur. J. Endocrinol., 144:145-154 (2001) 10 pages.
Lawler et al., "Cell Attachment to Thrombospondin: The Role of ARG-GLY-ASP, Calcium and Integrin Receptors", J. Cell Biol., 107(6 Pt. 1): 2351-2361 (1988) 11 pages.
Letterio et al., "Maternal Rescue of Transforming Growth Factor-β1 Null Mice", Science, 264:1936-1938 (1994) 4 pages.
Li et al., "Requirement of hypoxia-inducible factor-1α downregulation in mediating the antitumor activity of the anti-epidermal growth factor receptor monoclonal antibody cetuximab", Mol. Cancer Ther., 7(5):1207-1217 (2008) 11 pages.
Lin et al., "Androgen-induced human breast cancer cell proliferation is mediated by discrete mechanisms in estrogen receptor-α-positive and -negative breast cancer cells", J. Steroid Biochem. Mol. Biol., 113:182-188 (2009) 7 pages.
Lin et al., "Identification of the Putative MAP Kinase Docking Site in the Thyroid Hormone Receptor-β1 DNA-Binding Domain: Functional Consequences of Mutations at the Docking Site", Biochem., 42:7571-7579 (2003) 9 pages.
Lin et al., "Integrin αvβ3 contains a receptor site for resveratrol", FASEB J., 20(10): 1742-1744 (2006) 3 pages.
Lin et al., "L-Thyroxine v. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages.
Lin et al., "Resveratrol Causes COX-2- and p53-Dependent Apoptosis in Head and Neck Squamous Cell Cancer ells", J. Cell Biochem., 104:2131-2142 (2008) 12 pages.
Lin et al., "Resveratrol Induced Serine Phosphorylation of p53 Causes Apoptosis in a Mutant p53 Prostate Cancer Cell Line", J. Urol., 168:748-755 (2002) 8 pages.
Lin et al., "Resveratrol is pro-apoptotic and thyroid hormone is anti-apoptotic in glioma cells: both actions are integrin and ERK mediated", Carcinogenesis, 29(1):62-69 (2008) 8 pages.
Lin et al., "The pro-apoptotic action of stilbene-induced COX-2 in cancer cells: Convergence with the anti-apoptotic affect of thyroid hormone", Cell Cycle, 8(12):1877-1882 (2009) 6 pages.
Lin et al., "Thyroid hormone is a MAPK-dependent growth factor for thyroid cancer cells and is anti-apoptotic", Steroids, 72:180-187 (2007) 8 pages.
Liu et al., "Calcineurin Is a Common Target of Cyclophilin-Cyclosporin A and FKBP-FK506 Complexes", Cell, 66:807-815 (1991) 9 pages.
Lorger et al., "Activation of tumor cell integrin αvβ3 controls angiogenesis and metastatic growth in the brain", Proc. Natl. Acad. Sci. USA, 106(26):10666-10671 (2009) 7 pages.
Louie et al. "Pharmacodynamics of Levofloxacin in a Murine Pneumonia Model of *Pseudomonas aeruginosa* Infection: Determination of Epithelial Lining Fluid Targets", Antimicrob Agents Chemother., 53(8):3325-3330 (2009) 6 pages.
Luidens et al., "Thyroid hormone and angiogenesis", Vascular Pharmacology, 52(3-4): 142-145 (2010) 4 pages.
Lyons et al., "The Expression of an N-CAM Serum Fragment is Positively Correlated with Severity of Negative Features in Type II Schizophrenia", Biol. Psychiatry, 23:769-775 (1988) 7 pages.
Ma, et al., "Use of Encapsulated Single Chain Antibodies for Induction of Anti-Idiotypic Humoral and Cellular Immune Responses", J. Pharm. Sci., 87:1375-1378 (1998). 4 pages.
Mahmood et al., "An N2S2 Teradentate Chelate for Solid-Phase Synthesis: Evaluation in Solution and Solid Phase and Character-

(56) References Cited

OTHER PUBLICATIONS ization of Technetium-99 Complexes", Technetium, Rhenium and Other Metals in Chemistry and Nuclear Medicine, 5:71-76 (1999) 6 pages.

Mandelin et al., "Extracellular and Intracellular Mechanisms That Mediate the Metastatic Activity of Exogenous Osteopontin", Cancer, 115:1753-1764 (2009) 12 pages.

Mangale et al., "Identification of genes regulated by an interaction between αvβ3 integrin and vitronectin in murine decidua", Reprod. Fertil. Dev., 20:311-319 (2008) 10 pages.

Markgraf et al., "Sensorimotor and cognitive consequences of middle cerebral artery occlusion in rats", Brain Res., 575(2):238-246 (1992) 10 pages.

Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", Clin. Cancer Res., 14(17):5447-5458 (2008) 12 pages.

Masson-Gadais et al., "Integrin αvβ3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.

McCarty et al., "Promises and Pitfalls of Anti-Angiogenic Therapy in Clinical Trials." Trends Mol. Med. 9.2(2003):53-58 6 pages.

Meneses et al., "Recombinant angiostatin prevents retinal neovascularization in a murine proliferative retinopathy model", Gene Therapy, 8(8):646-648 (2011) 3 pages.

Mezosi et al., "Nongenomic effect of thyroid hormone on free-radical production in human polymorphonuclear leukocytes", J. Endocrinol., 185:121-129 (2005) 9 pages.

Mishkin et al., "Increased Survival of Rats Bearing Morris Hepatoma 7800 after Induction of Hypothyroidism", Cancer Res., 39:2371-2375 (1979) 5 pages.

Miyaguchi et al., "Correlation of Epidermal Growth Factor Receptor and Radiosensitivity in Human Maxillary Carcinoma Cell Lines", ActaOtolaryngol., 118:428-431 (1998) 4 pages.

Moeller et al., "Cytosolic Action of Thyroid Hormone Leads to Induction of Hypoxia-inducible Factor-1α and Glycolytic Genes", Molec. Endo., 19(12):2955-2963 (2005) 9 pages.

Moeller et al., "Thyroid hormone mediated changes in gene expression can be initiated by cytosolic action of the thyroid hormone receptor beta through the phosphatidylinositol 3-kinase pathway", Nuclear Receptor Signaling, 4: E020 (2006) 4 pages.

Mohamed et al., "Wound healing properties of cimetidine in vitro", Drug Intell. Clin. Pharm., 20(12):973-975 (1986) 4 pages.

Monferran et al., "αvβ3 and αvβ5 integrins control glioma cell response to ionising radiation through ILK and RhoB" Int. J. Cancer, 123:357-364 (2008) 8 pages.

Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.

Moreno et al., "Metabolic Effects of Thyroid Hormone Derivatives", Thyroid, 18(2):239-253 (2008) 15 pages.

Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18(2):239-253 (2008) 15 pages.

Mousa et al., "Cellular and Molecular Mechanisms of Nicotine's Pro-Angiogenesis Activity and Its Potential Impact on Cancer", J. Cell. Biochem., 97:1370-1378 (2006) 9 pages.

Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages.

Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages.

Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages.

Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages.

Mousa et al., "The Proangiogenic Action of Thyroid Hormone Analogue GC-1 Is Initiated at an Integrin", J. Cardiovasc. Pharmacol., 46(3):356-360 (2005) 6 pages.

Mousa, et al., "Pro-angiogenesis action of thyroid hormone and analogs in a three-dimensional in vitro microvascular endothelial sprouting model", Int. Angiol., 25(4):407-413 (2006).

Mousa, S.A., "Mechanisms of Angiogenesis: Potential Therapeutic Targets", in Angiogenesis Inhibitors and Stimulators: Potential Therapeutic Implications, Landes Bioscience, Georgetown, Texas, Chapter I, pp. 1-12 (2000) 14 pages.

Mousa, S.A., et al., "Effect of Resveratrol on Angiogenesis and Platelet/Fibrin-Accelerated Tumor Growth in the Chick Chonoallantoic Membrane Model," Nutr. Cancer, 52(1):59-65 (2005) 7 pages.

Muller et al., "The Double Life of the Ku Protein: Facing the DNA Breaks and the Extracellular Environment", Cell Cycle, 4(3):438-441 (2005) 4 pages.

Ndiaye et al., "Red wine polyphenol-induced, endothelium-dependent N-mediated relaxation is due to the redox-sensitive PI3-kinase / Akt-dependent phosphorylation of endothelial NO-synthase in the isolated porcine coronary artery", FASEB J., 19(3):455-457 (2005) 3 pages.

Nehls et al., "A microcamer-based concultivation system for the investigation of factors and cells involved in angiogenesis in three-dimensional fibrin matrices in vitro", Histochem. Cell Biol., 104(6):459-466 (1995) 8 pages.

Estrada-Ortiz, Natalia, et al. "Artificial Macrocycles as Potent p53-MDM2 Inhibitors," ACS Med. Chem. Lett. 2017, 8, 1025-1030, 6 pages.

Surmiak, Ewa, et al. "Rational design and synthesis of 1,5-disubstituted tetrazoles as potent inhibitors of the MDM2-p53 interaction," European Journal of Medicinal Chemistry, 126, (2017) 384-407, 24 pages.

Suryakiran, N., et al. "Facile N-tert-butoxycarbonylation of amines using La(NO3)3•6J2O as a mild and efficient catalyst under solvent-free conditions," Tetrahedron Letters, 47 (2006), 8039-8042; 4 pages.

Office Action (dated Jul. 21, 2010) for U.S. Appl. No. 12/004,979, filed Dec. 21, 2007.

Restriction Requirment (dated Sep. 14, 2012) for U.S. Appl. No. 12/626,068, filed Nov. 25, 2009.

Office Action (dated Jan. 4, 2013) for U.S. Appl. No. 12/626,068, filed Nov. 25, 2009.

Notice of Allowance (dated Apr. 29, 2013) for U.S. Appl. No. 12/626,068, filed Nov. 25, 2009.

Office Action (dated Mar. 16, 2011) for U.S. Appl. No. 11/663,047, filed Oct. 9, 2007.

Notice of Allowance (dated Aug. 22, 2011) for U.S. Appl. No. 11/663,047, filed Oct. 9, 2007.

Restriction Requirement (dated Oct. 8, 2010) for U.S. Appl. No. 11/992,152, filed Nov. 3, 2009.

Office Action (dated Dec. 10, 2010) for U.S. Appl. No. 11/992,152, filed Nov. 3, 2009.

Restriction Requirement (dated Feb. 7, 2013) for U.S. Appl. No. 13/345,194, filed Jan. 6, 2012.

Office Action (dated Apr. 29, 2013) for U.S. Appl. No. 13/345,194, filed Jan. 6, 2012.

Office Action (dated Oct. 15, 2013) for U.S. Appl. No. 13/345,194, filed Jan. 6, 2012.

Notice of Allowance (dated Feb. 6, 2014) for U.S. Appl. No. 13/345,194, filed Jan. 6, 2012.

Restriction Requirement (dated Mar. 13, 2012) for U.S. Appl. No. 12/751,375, filed Mar. 31, 2010.

Office Action (dated Jul. 13, 2012) for U.S. Appl. No. 12/751,375, filed Mar. 31, 2010.

(56) References Cited

OTHER PUBLICATIONS

Office Action (dated Apr. 12, 2013) for U.S. Appl. No. 12/751,375, filed Mar. 31, 2010.
Office Action (dated Jan. 12, 2015) for U.S. Appl. No. 12/751,375, filed Mar. 31, 2010.
Office Action (dated Jun. 3, 2015) for U.S. Appl. No. 12/751,375, filed Mar. 31, 2010.
Notice of Allowance (dated Jul. 7, 2015) for U.S. Appl. No. 12/751,375, filed Mar. 31, 2010.
Restriction Requirement (dated May 18, 2007) for U.S. Appl. No. 10/943,072, filed Sep. 14, 2004.
Office Action (dated Jul. 9, 2007) for U.S. Appl. No. 10/943,072, filed Sep. 14, 2004.
Office Action (dated Dec. 21, 2007) for U.S. Appl. No. 10/943,072, filed Sep. 14, 2004.
Advisory Action (dated Feb. 27, 2008) for U.S. Appl. No. 10/943,072, filed Sep. 14, 2004.
Office Action (dated May 15, 2008) for U.S. Appl. No. 10/943,072, filed Sep. 14, 2004.
Office Action (dated Jan. 8, 2009) for U.S. Appl. No. 10/943,072, filed Sep. 14, 2004.
Office Action (dated Jun. 22, 2009) for U.S. Appl. No. 10/943,072, filed Sep. 14, 2004.
Notice of Allowance (dated Dec. 11, 2009) for U.S. Appl. No. 10/943,072, filed Sep. 14, 2004.
Benedetti et al., "Life Tables and Survivor Functions", in BMDP Statistical Software Manual, BMDP Statistical Software, Inc., vol. 2, p. 573 and 689-718 (1988) 33 pages.
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974) 14 pages.
Bennett et al., "A peptide derived from a-fetoprotein prevents the growth of estrogen-dependent human breast cancers sensitive and resistan to tamoxifen", Proc. Natl. Acad. Sci. USA, 99(4):2211-2215 (2002) 5 pages.
Bergers et al., "Modes of resistance to anti-angiogenic therapy", Nat. Rev. Cancer, 8(8):592-603 (2008) 23 pages.
Bergh et al., "Integrin $\alpha v \beta 3$ contains a cell surface receptor site for thyroid hormone that is linked to activation of mitogen-activated protein kinase and induction of angiogenesis", Endocrinology, 146(7):2864-2871 (2005) 8 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bhat et al., "NCAM-180, the largest component of the neural cell adhesion molecule, is reduced in dysmyelinating quaking mutant mouse brain", Brain Res., 452:373-377 (1988) 5 pages.
Bilello et al., "Effect of 2', 3'-Didehydro-3'-Deoxythymidine in an In Vitro Hollow-Fiber Pharmacodynamic Model System Correlates with Results of Dose-Ranging Clinical Studies", Antimicrob Agents Chemother., 38(6):1386-1391 (1994) 6 pages.
Blaszczyk-Thurin et al., "An Experimental Vaccine Expressing Wild-Type p53 induces Protective Immunity Against Glioblastoma Cells with High Levels of Endogenous p53", Scand. J. Immunol., 56:361-375 (2002) 15 pages.
Blight, A.R., "Macrophages and Inflammatory Damage in Spinal Cord Injury", J. Neurotrauma, 9(Suppl. 1):S83-S91 (1992) 10 pages.
Blood et al., "Tumor interactions with the vasculature: angiogenesis and tumor metastasis", Bioch. Biophys. Acta, 1032:89-118 (1990) 30 pages.

Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.
Bomebroek et al., "Potential for imaging cerebral amyloid deposits using 123I-labelled serum amyloid P component and SpET", Cucl. Med. Commun., 17:929-933 (1996) 6 pages.
Bozarth et al., "An improved method for the quantitation of cellular migration: Rose of $\alpha 84$ $\beta 3$ integrin in endothelial and smooth muscle cell migration", Meth. Cell Sci., 19(3):179-187 (1997) 9 pages.
Brachmann et al., "The SIR2 gene family, conserved from bacteria to humans, functions in silencing, cell cycle progression, and chromosome stability", Genes Dev. 9:2888-2902 (1995) 15 pages.
Braughler et al., "Involvement of Lipid Peroxidation in CNS Injury", J. Neurotrauma, 9(Suppl. 1):S1-S7 (1992) 8 pages.
Breier et al., "The role of vascular endothelial growth factor in blood vessel formation", Trends in Cell Biol., 6:454_456 (1996) 3 pages.
Bridoux et al., "Semisynthesis and pharmacological activities of Tetrac analogs: Angiogenesis modulators", Bioorg. Med. Chem. Lett., 19:3259-3263 (2009) 5 pages.
Bridoux et al., "Semisynthesis and pharmacological activities of thyroxine analogs: Development of new angiogenesis modulators", Bioorg. Med. Chem. Lett., 20(11):3394-3398 (2010) 5 pages.
Brockhoff et al., "Differential impact of Cetuximab, Pertuzumab and Trastuzumab on BT474 and SK-BR-3 breast cancer proliferation", Cell Prolif., 40:488-507 (2007) 20 pages.
Brooks et al., "Antintegrin $\alpha v \beta 3$ blocks human breast cancer growth and angiogenesis in human skin", J. Clin. Invest., 96(4):1815-1822 (1995) 8 pages.
Bulitta et al., "Development and Qualification of a Pharmacodynamic Model for the Pronounced Inoculum Effect of Ceftazidime against *Pseudomonas aeruginosa*", Antimicrob. Agents Chemother., 53(1):46-56 (2009) 11 pages.
Burgman et al., "Effect of Inhibitors of Poly(ADP-Ribose)Polymerase on the Radiation Resposne of HeLa S3 Cells", Radiat Res., 119:380-386 (1989) 7 pages.
Carmeliet et al., "Molecular Basis of Angiogenesis Role of VEGF and VE-Cadherin", Ann. N.Y. Acad. Sci., 902:249-264 (2000) 16 pages.
Chanoine et al., "The role of transthyretin in the transport of thyroid hormone to cerebrospinal fluid and brain", Acta Medica Austriaca, 19(Suppl. 1):25-28 (19920) 5 pages.
Charness et al., "Ethanol Increases the Expression of Functional Delta-Opioid Receptors in Neurblastoma x Glioma NG108-15 Hybrid Cells", J. Biol. Chem., 261(7):3164-3169 (1986) 6 pages.
Charo et al., "The Vitronectin Receptor $\alpha v \beta 3$ Binds Fibronectin and Acts in Concert with $\alpha 5 \beta 1$ in Promoting Cellular Attachment and Spreading on Fibronectin", J. Cell Biol., 111(6 Pt. 1): 2795-2800 (1990) 6 pages.
Chase et al., "Principles of Radioisotope Methodology", 2nd Ed., Minneapolis, MN. Burgess Publ. Co., 1962, pp. 68, 87-90. 7 pages.
Chavakis et al., "Kinetics of integrin expression in the mouse model of proliferative retinopathy and success of secondary intervention with cyclic RGD peptides", Diabetologia, 45:262-267 (2002) 6 pages.
Cheng et al., "Molecular Aspects of Thyroid Hormone Actions", Endocri. Rev., 31(2): 139-170 (2010) 32 pages.
Cheresh et al., "Biosynthetic and Functional Properties of an Arg-Gly-Asp-directed Receptor Involved in Human Melanoma Cell Attachment to Vitronectin, Fibrinogen and von Willibrand Factor", J. Biol. Chem., 262(36):17703-17711 (1987) 9 pages.
Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475.
Chiaguri et al., "Anoikis: A necessary death program for anchorage-dependent cells", Biochem. Pharmacol., 76:1352-1364 (2008) 13 pages.
Chinese Office Action for Application No. 2004800331846 dated Mar. 5, 2010 7 pages.
Chinese Office Action for Application No. 2004800331846, dated Nov. 30, 2007, cited CN 1126589. 6 pages.

(56) References Cited

OTHER PUBLICATIONS

Clifton et al., "Marked Protection by Moderate Hypothermia After Experimental Traumatic Brain Injury", J. Cereb. Blood Flow Metab., 11(1):114-121 (1991) 9 pages.
Cody et al., "Molecular modeling of the thyroid hormone interactions with αvβ3 integrin", Steroids, 72:165-170 (2007) 6 pages.
Cohen-Jonathan et al., "Radioresistance Induced by the High Molecular Forms of the Basic Fibroblast Growth Factor Is Associated with an increased G2 Delay and a Hyperphosphorylation of p34CDC2 in HeLa Cells", Cancer Res., 57:1364-1370 (1997) 7 pages.
Cohen-Jonathan et al., "αvβ3 integrin pathway controls glioma radioresistance through ILK", Proc. Amer. Assoc. Cancer Res., 47:5180 (2006) (Abstract Only) 2 pages.
Cox et al., "The repair of potentially lethal damage in X-irradiated cultures of normal and ataxia telangiectasia human fibroblasts", Int. J. Radiat. Biol., 39(4):357-365 (1981) 9 pages.
Cristofanilli et al., "Thyroid Hormone and Breast Carcinoma. Primary Hypothyroidism is Associated with a Reduced Incidence of Primary Breast Carcinoma", Cancer, 103(6):1122-1128 (2005) 7 pages.
D'Arezzo et al., "Rapid Nongenomic Effects of 3,5,3'-Triiodo-L Thyronine on the Intracellular pH of L-6 Myoblasts are Mediated by Intracellular Calcium Mobilization and Kinase Pathways", Endocrinol., 145(12):5694-5703 (2004) 10 pages.
Database BIOSIS [Online], Accession No. PREV20040016159, Abstract, Mousa et al., "Discovery of pro-angiogenic effects of thyroid hormone and analogs", Blood, 102(11):77b-78b (2003) 1 page.
Davis et al., "Acting via a Cell Surface Receptor, Thyroid Hormone is a Growth Factor for Glioma cells," Cancer Res., 66(14):7270-7275 (2006) 6 pages.
Davis et al., "Cell-surface receptor for thyroid hormone and tumor cell proliferation", Expert Reviews of Endocrinology and Metabolism, 1(6):753-761 (2006) 10 pages.
Davis et al., "Mechanisms of nongenomic actions of thyroid hormone", Frontiers Neuroendocrinol., 29:211-218 (2008) 8 pages.
Davis et al., "Proangiogenic Action of Thyroid Hormone is Fibroblast Growth Factor-Dependent and is initiated at the Cell Surface." Cir. Res., 94(2004):1500-1506 7 pages.
Nehls et al., "A Novel Micorcarrier-Based in Vitro Assay for Rapid and Reliable Quantification of Three-Dimensional Cell Migration and Angiogenesis", Microvasc. Res., 50(3):311-322 (1995) 12 pages.
Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages.
Newcomb et al., "Radiation Sensitivity of GL261 Murine Glioma Model and Enhanced Radiation Response by Flavopindol", Cell Cycle, 5(1):93-99 (2006) 7 pages.
Nilsson et al., "Evidence for Multiple Thyroxine-binding Sites in Human Prealbumin", J. Biol. Chem., 246(19): 6098-6105 (1971) 8 pages.
Nickoloff et al., "Aberrant Production of Interleukin-8 and Thrombospondin-1 by Psoriatic Keratinocytes Mediates Angiogenesis." Am. J. Pathol. 144.4(1994):820-828 9 pages.
Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages.
Oak et al., "Antiangiogenic properties of natural polyphenols from red wine and green tea", J. Nutr. Biochem., 16:1-8 (2005) 8 pages.
Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages.
Pages et al., "Signaling Angiogenesis via p42/p44 MAP Kinase Cascade", Ann. N.Y. Acad., Sci., 902:187-200 (2000) 14 pages.
Painter et al., "Membrane initiation of DNA synthesis", Nature, 270:543 (1977) 1 page.
Panter et al., "Pretreatment with NMDA antagonists limits release of excitatory amino acids following traumatic brain injury", Neurosci. Lett., 136(2):165-168 (1992) 4 pages.

Panyam, et al., "Biodegradable nanoparticles for drug and gene delivery to cells and tissues", Advanced Drug Delivery Reviews, 55: 329-347 (2009) 19 pages.
Pardridge, W.M., "Receptor-Mediated Peptide Transport through the Blood-Brain Barrier", Endocrine Rev., 7(3):314-330 (1986) 18 pages.
Park et al., "Effects of Tetramethoxystilbene on Hormone-Resistant Breast Cancer Cells: Biological and Biochemical Mechanisms of Action", Cancer Res., 67:5717-5726 (2007) 10 pages.
Parveen, et al., "Polymeric nanoparticles for cancer therapy", Journal of Drug Targeting, 16(2): 108-123, Feb. 2008. 16 pages.
Patel, D.K., "Clinical Use of Anti-Epidermal Growth Factor Receptor Monoclonal Antibodies in Metastatic Colorectal Cancer", Pharmacotherapy, 28(11 Pt.2):31S-41S (2008) 12 pages.
Penno et al., "Rapid and quantitative in vitro measurement of cellular chemotaxis and invasion", Meth. Cell Sci., 19:189-195 (1997) 7 pages.
Pirola, et al., "Resveratrol: One Molecule, Many Targets", IUBMB Life, vol. 60, Issue 5, pp. 323-332. 10 pages.
Plow et al., "Ligand Binding to Integrins", J. Biol. Chem., 275(29):21785-21788 (2000) 4 pages.
Powell, J., "The Serial Analysis of Gene Expression", in Meth. Mol. Biol., Chapter 20, 99:297-319 (2000) 23 pages.
Prichard et al., "Concurrent Cetuximab and Bevacizumab Therapy in a Murine Orthotopic Model of Anaplastic Thyroid Carcinoma", Laryngoscope, 117:674-679 (2007) 7 pages.
Pujol et al., "Letter to the editors: Prevention of thyroid neoplasm recurrence with Triac and levothyroxine", Clin. Endocnnol., 46(1):121-122 (1997) 2 pages.
Raue et al., "Multiple Endocrine Neoplasia Type 2", Horm. Res., 68(Suppl.5): 101-104 (2007) 4 pages.
Rayalam et al., "Resveratrol induces apoptosis and inhibits adipogenesis in 3T3-L1 adipocytes", Phytother. Res., 22:1367-1371 (2008) 5 pages.
Rebbaa et al., "Novel function of the thyroid hormone analog tetraiodothyroacetic acid: a cancer chemosensitizing and anticancer agent", Angiogenesis, 11(3):269-276 (2008) 8 pages.
Reinholt et al., "Osteopontin—a possible anchor of osteoclasts to bone", Proc. Natl. Acad. Sci. U.S.A., 87:4473-4475 (1990) 3 pages.
Remsen et al., "Antibodies to the Neural Cell Adhesion Molecule Disrupt Functional Recovery in Injured Nerves", Exp. Neurol., 110:268-273 (1990) 6 pages.
Ren et al., "Regulation of tumor angiogenesis by thrombospondin-1", Biochim. Biophys. Acta. 1765: 178-188 (2006) 11 pages.
Risau, W., "Mechanisims of angiogenesis", Nature, 386:671-674 (1997) 4 pages.
Sahni et al., "Stimulation of endothelial cell proliferation by FGF-2 in the presence of fibrinogen requires αvβ3", Blood, 104(12):3635-3641 (2004) 7 pages.
Saito et al., "Vector-mediated delivery of 125I-labeled β-amyloid peptide Aβ1-40 through the blood-brain barrier and binding to Alzheimer disease of the Aβ1 40/vector complex", Proc. Natl. Acad. Sci. US, 92:10227-10231 (1995) 5 pages.
Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages.
SAS/STAT Guide for Personal Computers, Version 6 Edition, p. 717 (1987) 3 pages.
Sato et al., "Neovascularization: General Remarks", Biotherapy, 15(6):631-636 (2001) (English Abstract) 6 pages.
Scanlan et al., "3-Iodothyronamine is an endogenous and rapid-acting derivative of thyroid hormone", Nat. Med., 10(6):638-642 (2004) 5 pages.
Scanlan et al., "Selective thyromimetics: Tissue-selective thyroid hormone analogs", Curr. Opin. Drug Discov. Dev., 4(5):614-622 (2001) 9 pages.
Schlange et al., "Autocrine WNT signaling contributes to breast cancer cell proliferation via the canonical WNT pathway and EGFR transactivation", Breast Cancer Res., 9:R63 (2007) 15 pages.
Schlumberger et al., "New therapeutic approaches to treat medullary thyroid carcinoma", Nat. Clin. Prac. Endocrinol. Metab., 4(10):22-32 (2008) 11 pages.

(56) References Cited

OTHER PUBLICATIONS

Schnell et al., "Expression of alpha v beta 3 integrin in patients with high and low grade glioma", Proc. Amer. Assoc. Cancer Res., 47:226 (2006) Abstract Only. 5 pages.
Schnell et al., "Expression of Integrin αvβ3 in Gliomas Correlates with Tumor Grade and Is not Restricted to Tumor Vasculature", Brain Pathol., 18:378-386 (2008) 9 pages.
Schreiber et al., "Hormone delivery systems to the brain-transthyretin", Exp. Clin. Endocrinol. Diabetes, 103(2): 75-80 (1995) 7 pages.
Schueneman et al., "SU11248 Maintenance Therapy Prevents Tumor Regrowth after Fractionated Irradiation of Murine Tumor Models", Cancer Res., 63:4009-4016 (2003) 8 pages.
Shih et al., "Thyroid Hormone Promotes Serine Phosphorylation of p53 by Mitogen-Activated Protein Kinase", Biochem., 40:2870-2878 (2001) 10 pages.
Shih et al., "Disparate Effects of Thyroid Hormone on Actions of Epidermal Growth Factor and Transforming Growth Factor-α Are Mediated by 3,5'-Cyclic Adenosine 5'-Monophosphate-Dependent Protein Kinase II", Endo., 145(4): 1708-1717 (2004) 10 pages.
Shih et al., "Inhibitory effect of epidermal growth factor on resveratrol-induced apoptosis in prostate cancer cells is mediated by protein kinase C-α", Mol. Cancer Ther., 3:1355-1363 (2004) 9 pages.
Shinohara et al., "Enhanced radiation damage of tumor vasculature by mTOR inhibitors", Oncogene, 24:5414-5422 (2005) 9 pages.
Skrovronsky et al., "In vivo detection of amyloid plaques in a mouse model of Alzheimer's disease", Proc. Natl. Acad. Sci US, 97(13):7609-7614 (2000) 6 pages.
Skuli et al., "αvβ3/αvβ5 integrins-FAK-RhoB: A Novel Pathway for Hypoxia Regulation in Glioblastoma", Cancer Res., 69(8):3308-3316 (2009) 9 pages.
Song et al., "Formulation and characterization of biodegradable nanoparticles for intravascular local drug delivery", J. Controlled Rel., 43:197-212 (1997) 16 pages.
Stefani et al., "The Effect of Resveratrol on a Cell Model of Human Aging", Ann. NY Acad. Sci., 1114:407-418 (2007) 12 pages.
Davis et al., "Promotion by thyroid hormone of cytoplasm-to-nucleus shutting of thyroid hormone receptors", Steroids, 73:1013-1017 (2008) 5 pages.
Davis et al., "Thyroxine Promotes Association of Mitogen-activated Protein Kinase and Nuclear Thyroid Hormone Receptor (TR) and Causes Serine Phosphorylation of TR", J. Biol. Chem., 275(48):38032-38039 (2000) 8 pages.
Davis et al., "Translational implications of nongenomic actions of thyroid hormone initiated at its integrin receptor", Am. J. Physiol. Endocrinol. Metab., 297:E1238-E1246 (2009) 9 pages.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.
Demediuk et al., "Traumatic Spinal Cord Injury in Rats Causes Increases in Tissue Thromboxane But Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573(1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.
Ding et al., "Radioprotection of Hematopoietic Tissue by Fibroblast Growth Factors in Fractionated Radiation Experiments", Acta Oncol., 36(3):337-340 (1997) 4 pages.
Dixon et al., "A fluid percussion model of experimental brain injury in the rat", J. Neurosurg., 67(1):110-119 (1987) 11 pages.
Drusano et al., "Pharmacodynamics of Abacavir in an In Vitro Hollow-Fiber Model System", Antimicrob. Agents Chemother, 46(2):464-470 (2002) 7 pages.
Dupont et al., "Antiangiogenic and antimetastatic properties of Neovastat (Æ941), an orally active extract derived from cartilage tissue", Clin. Experim. Metastasis, 19:145-153 (2002) 9 pages.
Edwards et al., "Trypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10 (1983)10 pages.
Ely and Berne, "Protective Effects of Adenosine in Myocardial Ischemia", Circulation, 85:893-904 (1992) 13 pages.
Ethier et al., "Adenosine stimulates proliferation of human endothelial cells in culture", Am. J. Physiol., 265:H131-H138 (1993) 8 pages.
Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages.
Faden et al., "Endogenous Opioid Immunoreactivity in Rat Spinal Cord Following Traumatic Injury", Ann. Neurol., 17(4):386-390 (1985) 5 pages.
Faden, A.I., "Experimental Neurobiology of Central Nervous System Trauma", Crit. Rev. Neurobiol., 7(3-4):175-186 (1993) 13 pages.
Feeney et al., "Amphetamine, Haloperidol, and Experience Interact to Affect Rate of Recovery After Motor Cortex Injury", Science, 217(4562):855-857 (1982) 4 pages.
Fei et al., "P53 and radiation responses", Oncogene, 22:5774-5783 (2003) 10 pages.
Felding-Habermann et al., "Integrin activation controls metastasis in human breast cancer", Proc. Natl. Acad. Sci. U.S.A., 98(4):1853-1858 (2001) 6 pages.
Feng et al., "Fibrin and Collagen Differentially Regulate Human Dermal Microfascular Endothelial Cell Integrins: Stablization of αv/β3 mRNA by Fibrin", J. Invest. Dermatol., 113(6):913-919 (1999) 7 pages.
Fife et al., "Effects of tetracyclines on angiogenesis in vitro", Cancer Letters, 153:75-78 (2000) 4 pages.
Folkman, J., "Angiogenesis in cancer, vascular, rheumatoid and other disease", Nat. Med., 1(1):27-31 (1995) 5 pages.
Freese et al., "Characterization and mechanism of glutamate neurotoxicity in primary striatal cultures", Brain Res., 521(1-2):254-264 (1990) 12 pages.
Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.
Fujii et al., "Crystal Structure of Trimestatin, a Disintegrin Containing a Cell Adhesion Recognition Motif RGD", J. Mol. Biol., 332:1115-1122 (2003) 8 pages.
Gavrieli et al., "Identification of Programmed Cell Death In Situ via Specific Labeling of Nuclear DNA Fragmentation", J. Cell. Biol., 119(3):493-501 (1992) 9 pages.
GenBank Accession No. AF083106, Apr. 14, 2000 5 pages.
GenBank Accession No. AF083107, Mar. 21, 2001. 3 pages.
GenBank Accession No. NM_002210, Jun. 15, 2008 8 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.
Geng et al., "A Specific Antagonist of the p110δ Catalytic Component of Phosphatidylinositol 3'-Kinase, IC486068, Enhances Radiation-Induced Tumor Vascular Destruction", Cancer Res., 64:4893-4899 (2004) 7 pages.

(56) References Cited

OTHER PUBLICATIONS

Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages.

Gladson, C.L., "Expression of integrin $\alpha v \beta 3$ in Small Blood Vessels of Glioblastoma Tumors", J. Neuropath. Exp. Neurol., 55(11):1143-1149(1996) 7 pages.

Glinskii et al., "Modification of survival pathway gene expression in human breast cancer cells by tetraiodothyroacetic acid (tetrac)", Cell Cycle, 8(21):3562-3570 (2009) 9 pages.

Glinsky et al., "Classification of Human Breast Cancer Using Gene Expression Profiling as a Component of the Survival Predictor Algorithm", Clin. Cancer Res., 10:2272-2283 (2004) 12 pages.

Glinsky et al., "Gene expression profiling predicts clinical outcome of prostate cancer", J. Clin. Invest., 113(6):913-923 (2004) 11 pages.

Glinsky et al., "Microarray analysis identifies a death-from-cancer signature predicting therapy failure in patients with multiple types of cancer", J. Clin. Invest., 115(6):1503-1521 (2005) 19 pages.

Glinsky et al., "Microarray Analysis of Xenograft-Derived Cancer Cell Lines Representing Multiple Experimental Models of Human Prostate Cancer", Mol. Carcinog., 37:209-221 (2003) 13 pages.

Goldstein et al., "Influence of Lesion Size and Location on Amphetamine-Facilitated Recovery of Beam-Walking in Rats", Behav. Neurosci., 104(2):320-327 (1990) 9 pages.

Goldstein, A., "Estimating the Error Variance and the Confidence Interval for a Regression Line", in Biostatistics, The MacMillan Co., New York, pp. 139-146 (1964) 10 pages.

\* cited by examiner

Composition 201    Composition 202

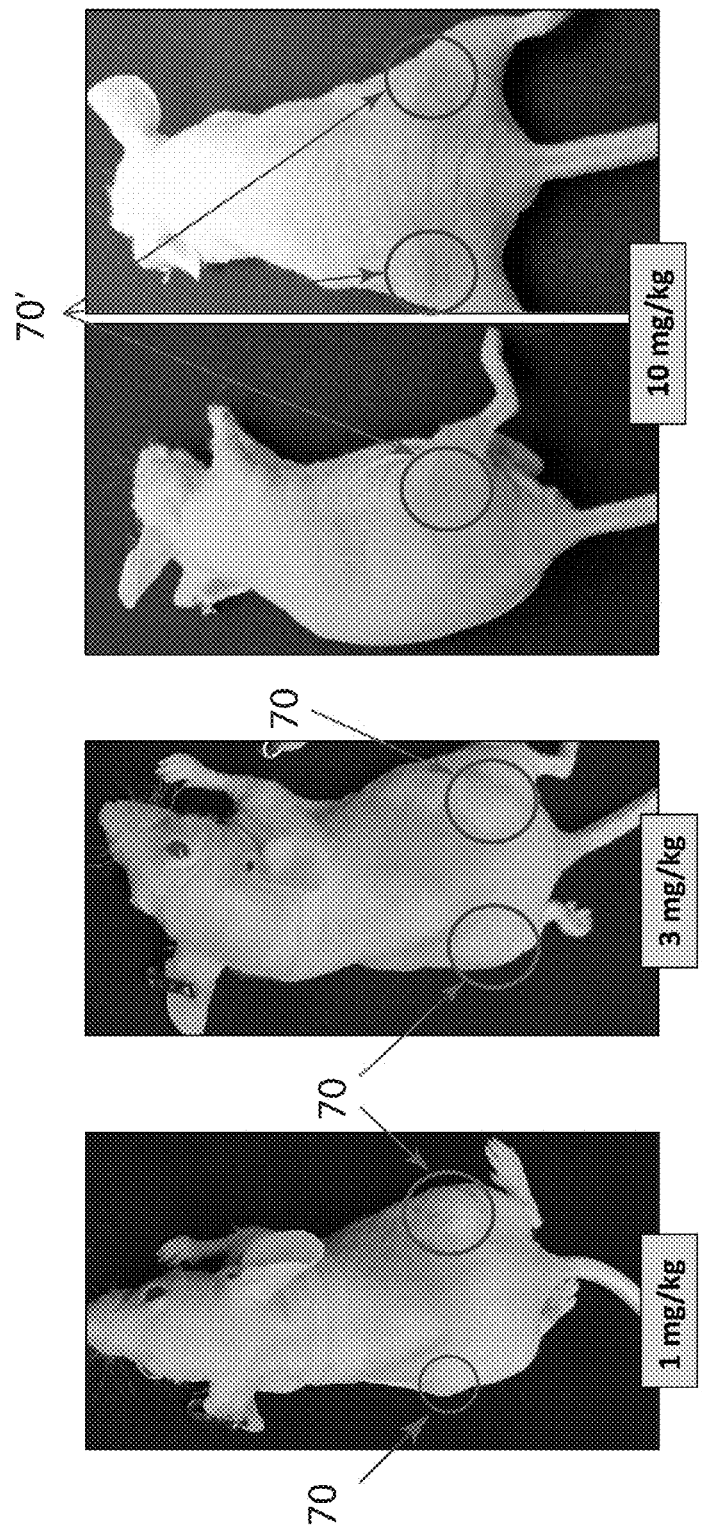

COMPOSITION AND METHOD FOR DUAL TARGETING IN TREATMENT OF NEUROENDOCRINE TUMORS

TECHNICAL FIELD

The present disclosure relates generally to compositions for targeting and treating neuroendocrine tumors. The composition in particular may include thyroid hormone αvβ3 integrin receptor antagonists (referred to as "thyrointegrin antagonists") and compounds that are targets of the norepinephrine transporter (NET) or the catecholamine transporter (such as benzyl guanidine ("BG") or its derivatives).

BACKGROUND

The norepinephrine/catecholamine transporter ("norepinephrine transporter") is essential for norepinephrine uptake at the synaptic terminals and adrenal chromaffin cells. In neuroendocrine tumors, the norepinephrine transporter is highly active and can be targeted for imaging and/or therapy with localized radiotherapy. One of the most widely used theranostic agents targeting the norepinephrine transporter is meta-iodobenzylguanidine (MIBG), a guanidine analog of norepinephrine. 123I/131I-MIBG theranostics have been applied in the clinical evaluation and management of neuroendocrine tumors, especially in neuroblastoma, paraganglioma, and pheochromocytoma. 123I-MIBG imaging has been used in the evaluation of neuroblastoma, and 131I-MIBG for the treatment of relapsed high-risk neuroblastoma, however, the outcome remains sub-optimal. Positron Emission Tomography (PET) tracers targeting the norepinephrine transporter and its targets represent a better option for the imaging and assessment after treatment of neuroblastoma, paraganglioma/pheochromocytoma, and carcinoids.

Integrins are a super-family of cell surface adhesion receptors, which control the attachment of cells with the solid extracellular environment, both to the extracellular matrix (ECM), and to other cells. Adhesion is of fundamental importance to a cell; it provides anchorage, cues for migration, and signals for growth and differentiation. Integrins are directly involved in numerous normal and pathological conditions, and as such are primary targets for therapeutic intervention. Integrins are integral transmembrane proteins, heterodimers, whose binding specificity depends on which of the 14 α-chains are combined with which of the 8 β-chains. The integrins are classified in four overlapping subfamilies, containing the β1, β2, β3 or αv chains. A cell may express several different integrins from each subfamily. In the last several decades, it has been shown that integrins are major receptors involved in cell adhesion, and so may be a suitable target for therapeutic intervention. Integrin αvβ3 regulates cell growth and survival, since ligation of this receptor can, under some circumstances, induce apoptosis in tumor cells. Disruption of cell adhesion with anti-αvβ3 antibodies, RGD peptides, peptide mimetic or non-peptide derivatives, and other integrin antagonists has been shown to slow tumor growth.

Thyrointegrin antagonists have been shown to effect tumor angiogenesis by interaction with integrin αvβ3. The effect of thyrointegrin antagonists is described in U.S. Pat. Pub. No. 2017/0348425 titled Non-Cleavable Polymer Conjugated with Alpa V Beta 3 Integrin Thyroid Antagonists, the contents of which are incorporated by reference.

A composition comprising both a thyrointegrin antagonist compound and a norepinephrine transporter target compound would be well received in the art.

SUMMARY

According to one aspect, a composition comprises N-benzyl guanidine and a thyrointegrin αvβ3 receptor antagonist, wherein the N-benzyl guanidine and the thyrointegrin αvβ3 receptor antagonist are connected by a linker.

According to another aspect, a composition comprises a general formula:

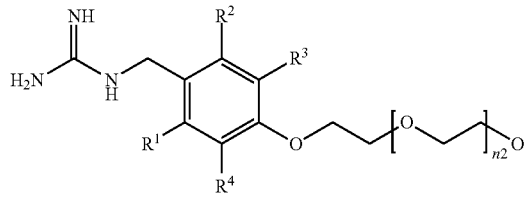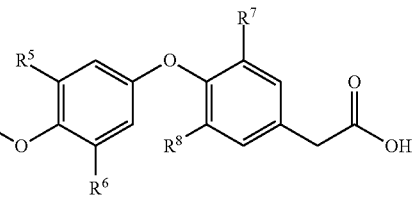

or a salt thereof, wherein R1, R2, R3, and R4 are each independently selected from the group consisting of hydrogen, iodine, fluorine, bromine, a methoxy group, a nitro group, an amine group, and a nitrile group, wherein R5, R6, R7, and R8 are each independently selected from the group consisting of hydrogen, iodine, and an alkane group, and $n1 \geq 0$; $n2 \geq 1$, and

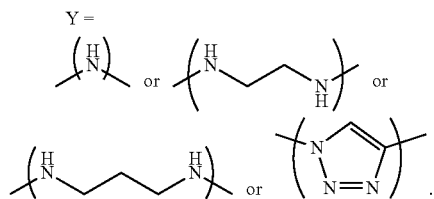

According to another aspect, a composition for dual targeting of tumor cells comprises a norepinephrine transporter target and a thyrointegrin αvβ3 receptor antagonist, wherein the norepinephrine transporter target and the αvβ3 thyrointegrin receptor antagonist are connected by a linker, further wherein the composition is configured to dual target tumor cells via a) the norepinephrine transporter and b) reaction with the integrin αvβ3 receptor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some of the embodiments will be described in detail with reference made to the following figures, in which like designations denote like members, wherein:

FIG. 4b depicts a detailed schematic of the synthetic pathway of FIG. 4a;

FIG. 7b shows images of mice that have been treated with Composition 300 and demonstrate significant reduction or absence of visible subcutaneous tumors (significant shrinkage to elimination of tumors) in a dose-dependent manner along with disappearance of the observed abnormal animal head movements;

DETAILED DESCRIPTION

Figure 1:
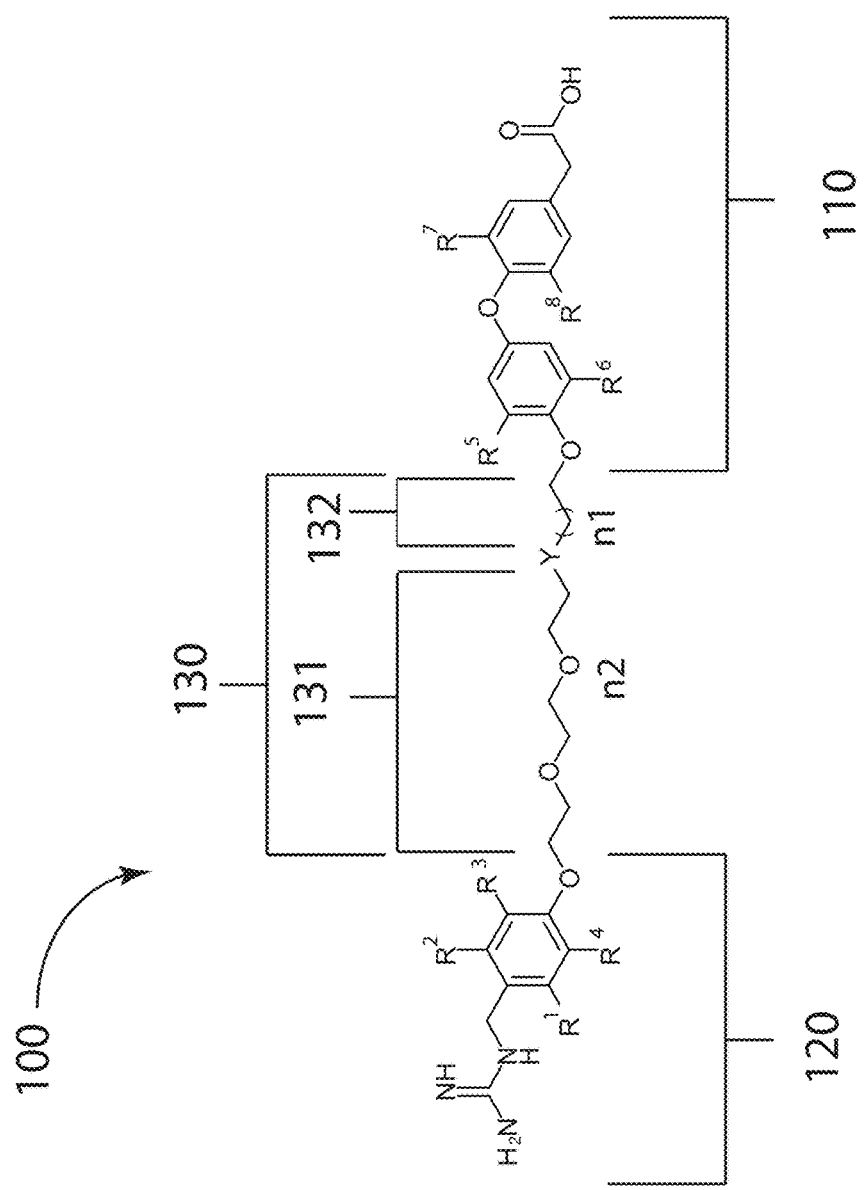
FIG. 1 depicts a general formula of an exemplary composition for use in dual targeting of neuroendocrine tumors.

A detailed description of the hereinafter-described embodiments of the disclosed composition and method is presented herein by way of exemplification and not limitation with reference to the Figures. Although certain embodiments are shown and described in detail, it should be understood that various changes and modifications might be made without departing from the scope of the appended claims. The scope of the present disclosure will in no way be limited to the number of constituting components, the materials thereof, the shapes thereof, colors thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

OVERVIEW

Embodiments of the present disclosure describe new chemical compositions, and methods of synthesis thereof. The compositions disclosed and described herein may be directed toward anti-angiogenic agents, particularly thyro-integrin antagonists, which may be capable of interacting with one or more cell surface receptors of the integrin $\alpha v\beta 3$ receptor family. The compositions disclosed and described herein may also be directed toward targets of the norepinephrine transporter (also known as the catecholamine transporter). Targets of the norepinephrine transporter may act as neuroendocrine tumor cell targeting agents.

The compositions disclosed and described herein may be directed toward a composition containing both a thyrointegrin antagonist and a norepinephrine transporter target. Further, the composition may use a polymer or other linker to link the thyrointegrin antagonist and the norepinephrine transporter target.

The norepinephrine transporter is a regulator of catecholamine uptake in normal physiology and is highly expressed and over-active in neuroendocrine tumors like neuroblastoma. Although the norepinephrine analog, meta-iodobenzylguanidine (MIBG), is an established substrate for the norepinephrine transporter, analogs such as (123)I/(131)I-MIBG or analogs having Fluoride (F18) instead of Iodide (radioactive) may also be used for diagnostic imaging of neuroblastoma and other neuroendocrine tumors.

Investigations have demonstrated that various neuroblastoma cell lines highly express the αvβ3 integrin receptors (90-95%). However, high affinity αvβ3 integrin receptor antagonists showed limited (40-50%) efficacy in term of tumor growth rate and cancer viability inhibition. Similarly, benzyl guanidine and its derivatives demonstrated limited anti-cancer efficacy of neuroblastoma despite its maximal (90-100%) uptake into neuroblastoma and other neuroendocrine tumors. Furthermore, treatment combinations of norepinephrine transporter targets such as benzyl guanidine or its derivatives together with thyrointegrin antagonists such as triazole tetraiodothyroacetic acid derivatives did not exceed 50% suppression of neuroblastoma growth and viability.

In contrast and unexpectedly, conjugation of norepinephrine transporter targets such as benzyl guanidine derivatives and thyrointegrin antagonists such as triazole tetraiodothryoacetic acid derivatives via different polymer linker such as Polyethylene Glycol (PEG) into a single novel chemical entity resulted in maximal uptake into neuroblastoma and other neuroendocrine tumors along with maximal (80-100%) suppression of tumor growth and viability at different doses. A thyrointegrin antagonist conjugated via a linker with a norepinephrine/catecholamine transporter target compound may provide a composition that has a dual targeting effect for neuroendocrine tumor targeting. For example, the composition may comprise an alpha-V-beta-3 (αvβ3) integrin-thyroid hormone receptor antagonist linked to benzyl guanidine (or a benzyl guanidine derivative) according to one embodiment of the invention.

The compositions described herein may be comprised of compounds, for example a thyrointegrin antagonist or derivative thereof covalently linked to a target of the norepinephrine transporter to form a single chemical entity. The thyrointegrin antagonist and the norepinephrine target may be joined via a linker.

Reference may be made to specific thyrointegrin compounds and norepinephrine compounds, for example, tetrac, triac, and benzyl guanidine. These phrases include derivatives of such compounds in accordance with the full teachings of this disclosure, even where such derivatives are not specifically listed.

Referring to the drawings, FIG. 1 depicts an embodiment of a general formula 100 comprising a thyrointegrin antagonist 110 joined to a norepinephrine transporter target 120 via a linker 130. The composition may be referred to as a thyrointegrin antagonist derivative conjugated to a benzyl guanidine derivative via the linker 130, or a thyrointegrin antagonist derivative conjugated to a benzyl guanidine derivative modified with the linker 130. FIG. 1 depicts a carboxylic acid form of the general formula 100. As would be apparent to one skilled in the art, a salt (e.g. a sodium salt) of the general formula 100 may also be used.

The linker 130 comprises a spacer 132 and a polymer 131. The linker 130 resists biodegradation such that the linker remains uncleaved under physiological conditions. In one embodiment, the spacer 132 comprises a $CH_2$ unit and an adjacent repeating linkage of methylene ($CH_2$) units which may be defined by n1 repeats wherein n1 is an integer that is ≥0. In other embodiments, n1 may be ≥1, ≥2 or ≥3. The linker 130 further comprises a moiety "Y." Embodiments of the moiety "Y", may in some instances be may be an amine. For example, the moiety Y of the general formula may be a divalent alkane having one amine group or a divalent alkane having two amine groups as shown by the examples of general formula 200a and 200b of FIGS. 2a and 2b. In another embodiment, the moiety Y may be a triazole as shown by the example of general formula 200c shown in FIG. 2c. The polymer 131 may comprise a polyether such as polyethylene glycol (PEG). Other polymers may be used, including chitosan, alginic acid, hyaluronic acid, and other polymers. In embodiments using PEG as the polymer 131, the polymer may have a molecular weight between 200 and 4,000 g per mole.

The term thyroid antagonist describes a compound that has the ability to inhibit or antagonize one or more thyroid hormone receptors known by a person skilled in the art, for example the integrin family of thyroid hormone receptors, such as the thyroid hormone cell surface receptor αvβ3. The thyrointegrin antagonist 110 may be an anti-angiogenic thyroid hormone or a thyroid hormone receptor antagonist. For example, the thyrointegrin antagonist 110 may be an alpha-V-beta-3 (αvβ3) integrin-thyroid hormone receptor antagonist.

Specific embodiments of the thyrointegrin antagonist 110 may include tetraiodothyroacetic acid (tetrac), triiodothyroacetic acid (triac), derivatives thereof and variations thereof. Examples of one or more variations of the thyrointegrin antagonist comprising tetrac and triac may include, in some embodiments Diaminotetrac (DAT) or Diaminotriac (DATri) (hereinafter may be referred to interchangeably as "DAT"), Monoaminotetrac (MAT) or Monoaminotriac (MATri) (hereinafter referred to interchangeable as "MAT"), Triazoletetrac (TAT) or Triazoletriac (TATri) (hereinafter referred to interchangeable as "TAT"), derivatives thereof or other thyroid antagonist known by those skilled in the art. Thyrointegrin antagonists may be of the type described in U.S. Pat. Pub. No. 2017/0348425 titled Non-Cleavable Polymer Conjugated with Alpa V Beta 3 Integrin Thyroid Antagonists, the contents of which are incorporated by reference.

Exemplary thyrointegrin antagonists based on the general structure 100 from FIG. 1 are shown below in Table 1.

TABLE 1

| | | Exemplary Thyrointegrin Antagonists | | |
|---|---|---|---|---|
| | $R^5$ | $R^6$ | $R^7$ | $R^8$ |
| 1 | | | | |
| 2 | H | H | H | H |

TABLE 1-continued

Exemplary Thyrointegrin Antagonists

| | | | | |
|---|---|---|---|---|
| 3 | I | H | H | H |
| 4 | H | I | H | H |
| 5 | H | H | I | H |
| 6 | H | H | H | I |
| 7 | I | I | H | H |
| 8 | I | H | I | H |
| 9 | H | H | I | I |
| 10 | I | I | I | H |
| 11 | H | I | I | I |
| 12 | I | I | I | I |
| 13 | H | H | H | H |
| 14 | iPr | H | H | H |
| 15 | H | iPr | H | H |
| 16 | H | H | iPr | H |
| 17 | H | H | H | iPr |
| 18 | iPr | iPr | H | H |
| 19 | iPr | H | iPr | H |
| 20 | H | H | iPr | iPr |
| 21 | iPr | iPr | iPr | H |
| 22 | H | iPr | iPr | iPr |
| 23 | iPr | iPr | iPr | iPr |
| 24 | tBu | H | H | H |

TABLE 1-continued

Exemplary Thyrointegrin Antagonists

| | R5 | R6 | R7 | R8 |
|---|---|---|---|---|
| 25 | H | C(CH$_3$)$_3$ | H | H |
| 26 | H | H | C(CH$_3$)$_3$ | H |
| 27 | H | H | H | C(CH$_3$)$_3$ |
| 28 | C(CH$_3$)$_3$ | C(CH$_3$)$_3$ | H | H |
| 29 | C(CH$_3$)$_3$ | H | C(CH$_3$)$_3$ | H |
| 30 | H | H | C(CH$_3$)$_3$ | C(CH$_3$)$_3$ |
| 31 | C(CH$_3$)$_3$ | C(CH$_3$)$_3$ | C(CH$_3$)$_3$ | H |
| 32 | H | C(CH$_3$)$_3$ | C(CH$_3$)$_3$ | C(CH$_3$)$_3$ |
| 33 | C(CH$_3$)$_3$ | C(CH$_3$)$_3$ | C(CH$_3$)$_3$ | C(CH$_3$)$_3$ |

In some embodiments of the thyrointegrin antagonist 110, the variables depicted as R5, R6, R7, and R8 may each independently be substituted for molecules such as hydrogen, iodine, and alkanes. In some embodiments, the alkanes have four or fewer carbons. For example, as shown in Table 1, in some embodiments of the thyrointegrin antagonist 110, the variables depicted as R5, R6, R7, and R8 may each independently be substituted for molecules of hydrogen, iodine, or alkane groups such as isopropyl or isobutyl. In the embodiments of Table 1, the alkanes have four or fewer carbons.

The norepinephrine transporter target 120 may be a neuroendocrine tumor cell targeting agent. As an example, the norepinephrine transporter target 120 may be benzyl guanidine or a benzyl guanidine derivative. As a further example, the norepinephrine transporter target 120 may be N-benzyl guanidine or a derivative thereof.

Exemplary norepinephrine transporter targets 120 based on the general formula 100 from FIG. 1 are shown below in Table 2.

TABLE 2

Exemplary Norepinephrine Transporter Targets

| | R$_1$ | R$_2$ | R$_3$ | R$_4$ |
|---|---|---|---|---|
| 1 | F | H | H | H |
| 2 | H | F | H | H |
| 3 | H | H | F | H |
| 4 | H | H | H | F |
| 5 | Br | H | H | H |
| 6 | H | Br | H | H |
| 7 | H | H | Br | H |
| 8 | H | H | H | Br |
| 9 | I | H | H | H |
| 10 | H | I | H | H |
| 11 | H | H | I | H |
| 12 | H | H | H | I |
| 13 | OH | H | H | H |
| 14 | H | OH | H | H |
| 15 | H | H | OH | H |
| 16 | H | H | H | OH |
| 17 | OMe | H | H | H |
| 18 | H | OMe | H | H |

TABLE 2-continued

Exemplary Norepinephrine Transporter Targets

| | $R_1$ | $R_2$ | $R_3$ | $R_4$ |
|---|---|---|---|---|
| 19 | H | H | OMe | H |
| 20 | H | H | H | OMe |
| 21 | NO2 | H | H | H |
| 22 | H | NO2 | H | H |
| 23 | H | H | NO2 | H |
| 24 | H | H | H | NO2 |
| 25 | NH2 | H | H | H |
| 26 | H | NH2 | H | H |
| 27 | H | H | NH2 | H |
| 28 | H | H | H | NH2 |
| 29 | CN | H | H | H |
| 30 | H | CN | H | H |
| 31 | H | H | CN | H |
| 32 | H | H | H | CN |

In some embodiments of the norepinephrine transporter target 120, the variables depicted as R1, R2, R3, and R4 may be each independently be substituted for molecules such as hydrogen, iodine, fluorine, bromine, a methoxy group, a nitro group, an amine group, and a nitrile group. For example, in some embodiments of the norepinephrine transporter target 120, the variables depicted as R1, R2, R3, and R4 may be each independently be substituted for molecules of hydrogen, iodine, fluorine, bromine, a methoxy group, a nitro group, an amine group, and a nitrile group as described above in Table 2. Additional embodiments and substitutions may also be used. In one embodiment at least one of R1, R2, R3 and R4 is a radiolabel. Examples of suitable radiolabels include I(123), I(131) and F(18). The compound may be administered to humans or animals.

Any of the exemplary thyrointegrin antagonists 110 (along with any of the other thyrointegrin antagonist embodiments taught herein) may be joined via the linker 130 to any of the exemplary norepinephrine transporter targets 120 (along with any of the other norepinephrine transporter target embodiments taught herein) to form a composition.

As is clear from Table 1 and Table 2, there are a large number of compounds that may be used as the thyrointegrin antagonist 110 and a large number of compounds that may be used as the norepinephrine transporter target 120 in the composition. Further, the various thyrointegrin antagonists 110 may be combined with various norepinephrine transporter targets 120, resulting in a large number of potential chemical structures for the composition described herein.

Embodiments of each of the compositions described herein may have multiple types of utility for treating a plurality of different diseases modulated by angiogenesis or the inhibition thereof. Each of the compositions described in the present disclosure, in view of presence of the thyrointegrin antagonist 110 present in the described compositions, may have an affinity for targeting the integrin receptor αvβ3 located on numerous types of cells found throughout the human body and various animal bodies.

Moreover, embodiments of each of the compositions described in the current application may have utility for treating a plurality of different diseases characterized by activity of the norepinephrine transporter. Each of the compositions described in the present disclosure, in view of presence of the norepinephrine transporter target 120 present in the described compositions, may each have an affinity for targeting numerous types of cells found throughout the human body and various animal bodies that utilize the norepinephrine transporter. Each of the compositions described in the present disclosure may have increased affinity for targeting cells demonstrating increased or above average activity of the norepinephrine transporter, such as neuroendocrine tumor cells. As a more specific example, the composition may have increased affinity for targeting neuroblastoma, pheochromocytoma, pancreatic neuroendocrine tumor, and carcinoid tumor cells.

Still further, due to the composition's use of both a thyrointegrin antagonist 110 and a norepinephrine transporter target 120, the composition may have increased utility and efficacy against certain diseases and/or conditions. For example, neuroendocrine tumors are susceptible to treatment with thyrointegrin antagonists while also demonstrating increased activity of the norepinephrine transporter. The compositions described herein make use of both compounds for a dual targeting effect in treatment of neuroendocrine tumor cells. Further, the increased effect surpasses any increase expected or achieved by simultaneous separate treatment with a thyrointegrin antagonist and a norepinephrine transporter target. Further details regarding the beneficial utility is discussed below with respect to experimental studies.

As shown by the chemical structure of the general formula 100 of FIG. 1, embodiments of the chemical structure may include one or more variables defining the additional features of the thyrointegrin antagonist 110 of the general formula 100. For example, in some embodiments of the thyrointegrin antagonist 110, the variables depicted as R5, R6, R7, and R8 may be each independently be hydrogen, iodine, and alkanes as described above in Table 1.

Figure 2A:
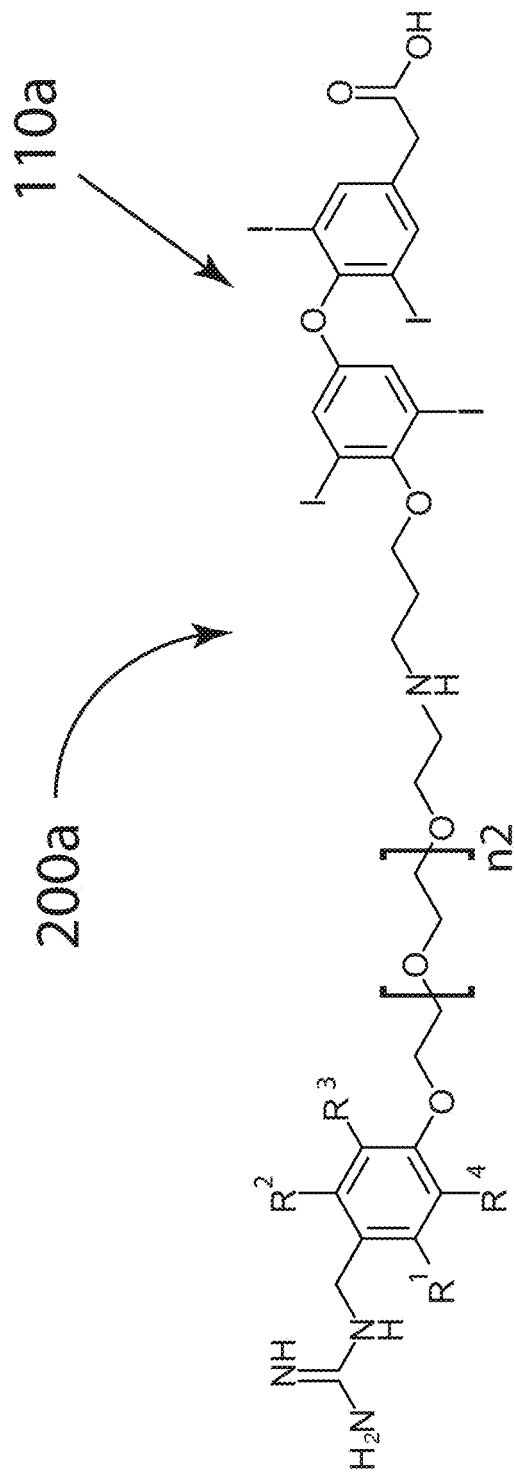
FIG. 2a depicts another general formula of an exemplary composition having a linker with a monoamine.
Figure 2B:
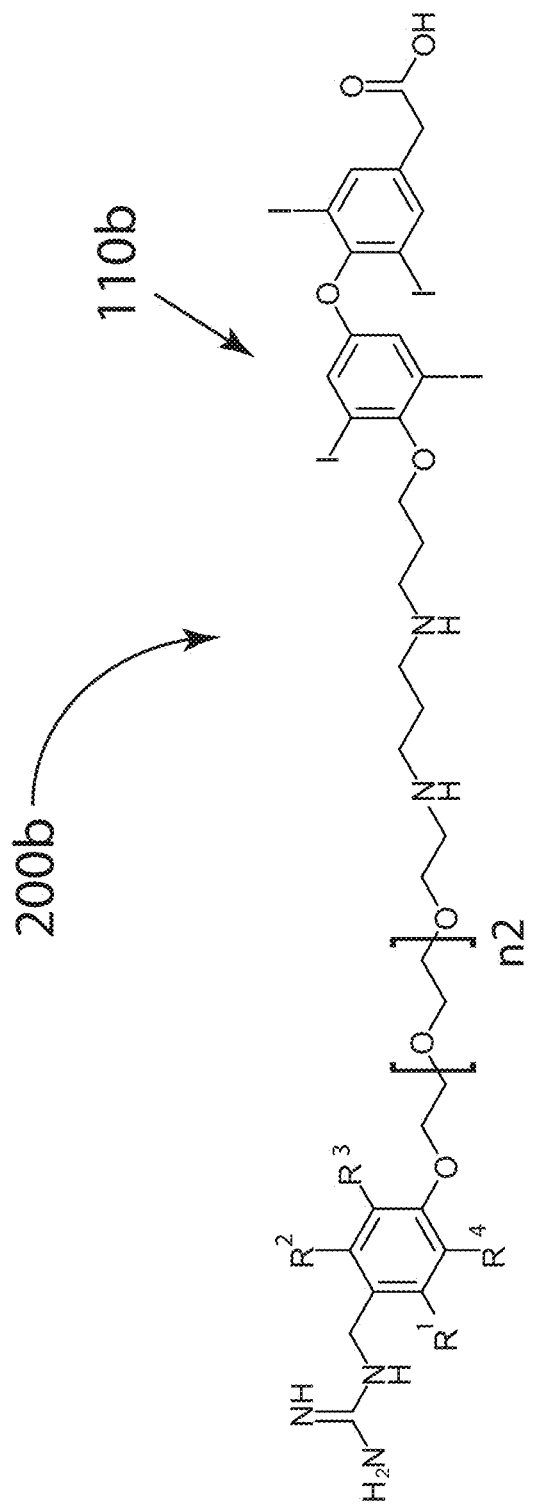
FIG. 2b depicts another general formula of an exemplary composition having a linker with a diamine.
Figure 2C:
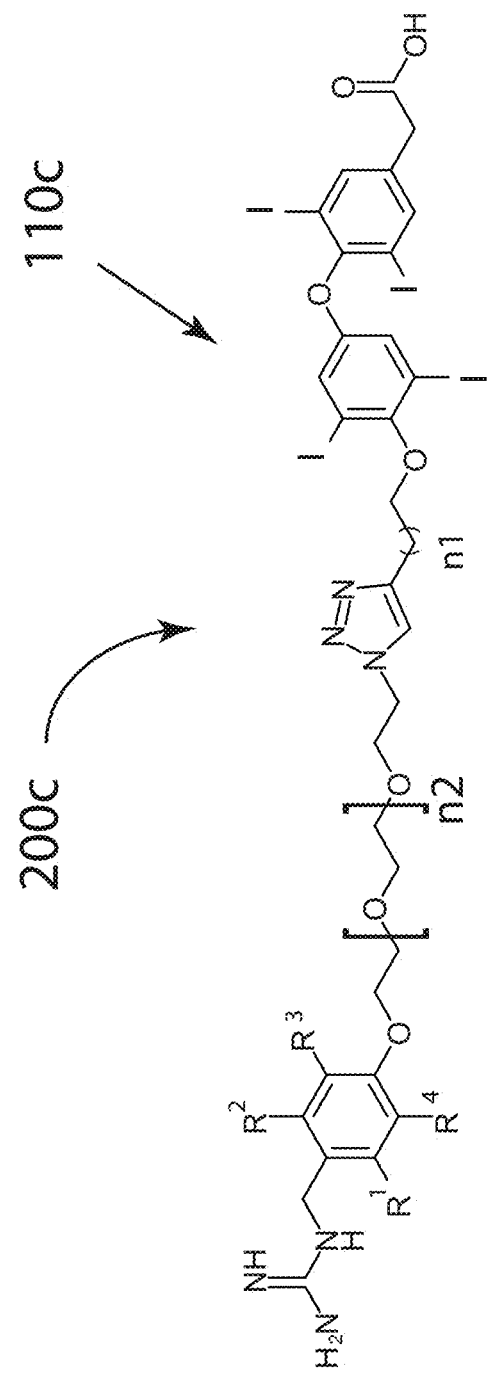
FIG. 2c depicts another general formula of an exemplary composition having a linker with a triazole.

There is thus a wide range of thyrointegrin antagonist compounds that may be used as the thyrointegrin antagonist 110 of the general formula 100. For example, as shown in FIG. 2a, the thyrointegrin antagonist 110a may comprise a substitution of iodine for R5-R8, resulting in the formation of a tetraiodothyroacetic acid (tetrac) derivative having a three-carbon linker and a monoamine as the Y moiety. General formula 200a may be referred to as monoamine-tetrac (MAT) conjugated via PEG to benzyl guanidine or a benzyl guanidine derivative. Likewise, in FIG. 2b, the tetrac molecule further comprises a diamino Y moiety connected to the carbon linker. This general formula 200b may be referred to as diamino tetrac (DAT) conjugated via PEG to benzyl guanidine or a benzyl guanidine derivative. In the alternative embodiment of FIG. 2c, the general formula 200c may comprise a triazole moiety connected to the single carbon of the carbon linker. This general formula 200c may be referred to as triazole tetrac (TAT) conjugated via PEG to benzyl guanidine or a benzyl guanidine derivative.

Other thyrointegrin antagonist compounds may also be used in forming the compositions described herein. For example, the general structure of the thyrointegrin antagonists 110a, 110b, and 110c may be used wherein only R5-R7 include iodine, thereby giving similar triac derivatives. Further, as shown in Table 1 above, similar structures may be used in which the thyrointegrin antagonist comprises a substitution of other elements or functional groups for any and/or all of R5-R8.

The norepinephrine transporter target 120 may comprise benzyl guanidine or a benzyl guanidine derivative. Embodiments of the chemical structure of the norepinephrine transporter target 120 may include one or more variables defining the additional features of the norepinephrine transporter target 120 of the general formula 100 shown in FIG. 1. For example, in some embodiments of the norepinephrine transporter target 120, the variables depicted as R1, R2, R3, and R4 may be each independently be substituted for molecules of hydrogen, iodine, fluorine, bromine, a methoxy group, a nitro group, an amine group, and a nitrile group as described above in Table 2.

Figure 3:
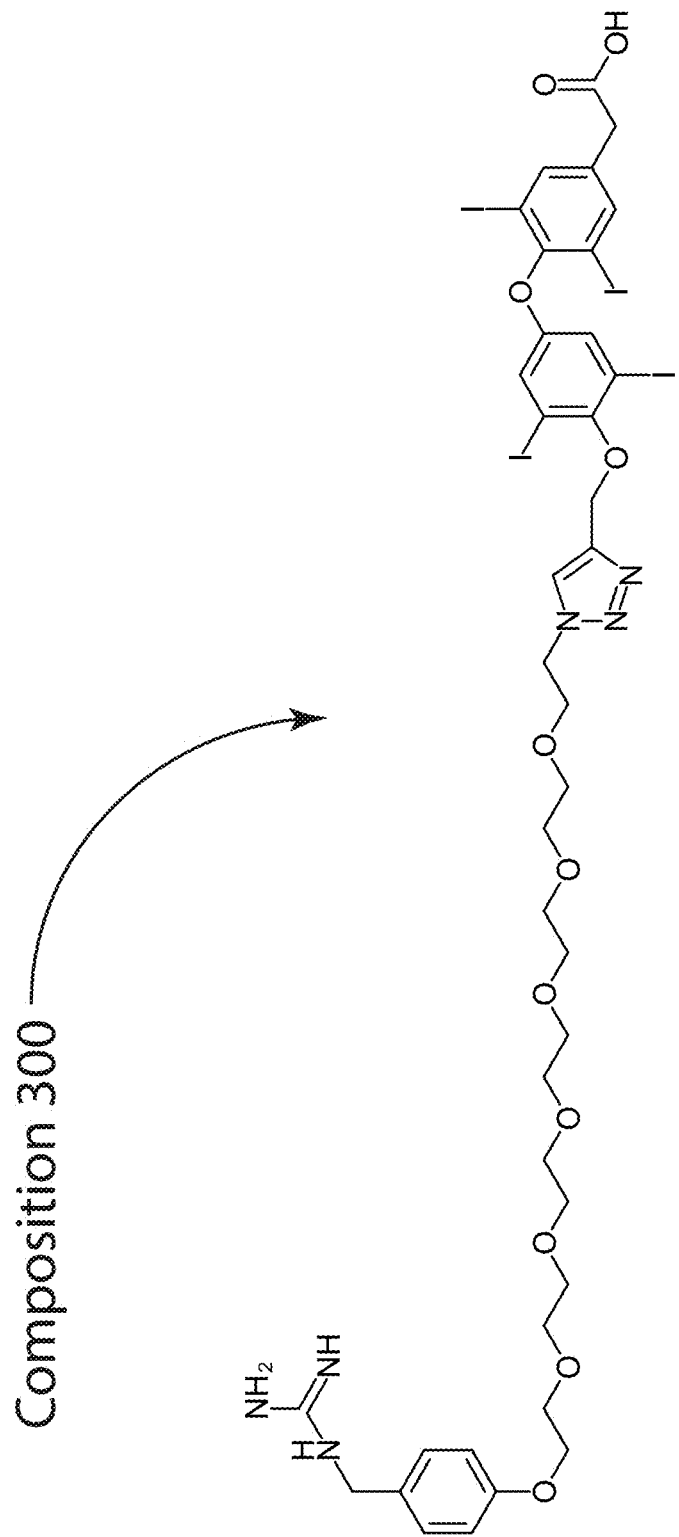
FIG. 3 depicts one exemplary composition for use in dual targeting of neuroendocrine tumors, referred to as Composition 300, BG-PEG-TAT, or BG-P-TAT.

FIG. 3 depicts an exemplary Composition 300 of the general formula 100. Composition 300 comprises triazole tetrac conjugated to benzyl guanidine modified PEG. Composition 300 may also be referred to as BG-PEG-TAT or BG-P-TAT.

Synthesis of the compositions described herein is demonstrated below, primarily with reference to the exemplary composition shown in FIG. 3, namely Composition 300. Synthesis of similar compositions, namely Composition 201 and Composition 202 (see FIG. 4c-4f) are also provided as examples and without limiting the disclosure to such compositions.

Example 1a: Synthesis of Exemplary Composition 300

This example provides a sample method for preparing Composition 300 shown in FIG. 3. Composition 300 is referred to as BG-PEG-TAT or BG-P-TAT. Composition 300 has the chemical name of 2-(4-(4-((1-(20-(4-(guanidinomethyl)phenoxy)-3,6,9,12,15,18-hexaoxaicosyl)-1H-1,2,3-triazol-4-yl)methoxy)-3,5-diiodophenoxy)-3,5-diiodophenyl)acetic acid, or [4-(4-{1-[2-(2-{2-[2-(2-{2-[2-(4-Guanidinomethyl-phenoxy)-ethoxy]-ethoxy}-ethoxy)-ethoxy]-ethoxy}-ethoxy)-ethyl]-1H-[1,2,3]triazol-4-ylmethoxy}-3,5-diiodo-phenoxy)-3,5-diiodo-phenyl]-acetic acid. The molecular weight of Composition 300 is 1284.44 g/mol.

All commercially available chemicals were used without further purification. All solvents were dried and anhydrous solvents were obtained using activated molecular sieves (0.3 or 0.4 nm depending on the type of solvent). All reactions (if not specifically containing water as reactant, solvent or co-solvent) were performed under Ar or $N_2$ atmosphere, in oven-dried glassware. All new compounds gave satisfactory $^1H$ NMR and mass spectrometry results. Melting points were determined on an Electrothermal MEL-TEMP® melting point apparatus and then on a Thomas HOOVER Unimel capillary melting point apparatus. Infrared spectra were recorded on a Thermo Electron Nicolet Avatar 330 FT-IR apparatus. UV spectra were obtained from a SHIMADZU UV-1650PC UV-vis spectrophotometer. The solution-state NMR experiments were all performed a Bruker Advance II 800 MHz spectrometer equipped with a cryogenically cooled probe (TCI) with z-axis gradients (Bruker BioSpin, Billerica, Mass.) at the Center for Biotechnology and Interdisciplinary Studies, Rensselaer Polytechnic Institute (RPI, Troy, N.Y.). All tubes used were 5 mm outside diameter. NMR data were referenced to chloroform ($CDCl_3$; 7.27 ppm $^1H$, 77.20 ppm $^{13}C$) or DMSO-d6 (δ=2.50 ppm, 38.92 ppm $^{13}C$) as internal reference. Chemical shifts δ are given in ppm; multiplicities are indicated as s (singlet), d (doublet), t (triplet), q (quartet), m (multiplet) and br (broad); coupling constants, J, are reported in Hz. Thin layer chromatography was performed on silica gel plates with fluorescent indicator. Visualization was accomplished by UV light (254 and/or 365 nm) and/or by staining in ceric ammonium molybdate or sulfuric acid solution. Flash column chromatography was performed following the procedure indicated in J. Org. Chem. 43, 14, 1978, 2923-2925, with 230-400 mesh silica gel. High resolution mass spectral analysis was performed on either an Applied Biosystems API4000 LC/MS/MS or Applied Biosystems QSTAR XL mass spectrometers.

This example uses propargylated tetrac (PGT). Preparation of PGT or a derivative thereof from tetrac is described in U.S. Pat. Pub. No. 2017/0348425 titled Non-Cleavable Polymer Conjugated with Alpa V Beta 3 Integrin Thyroid Antagonists, the contents of which are incorporated by reference.

Figure 4A:
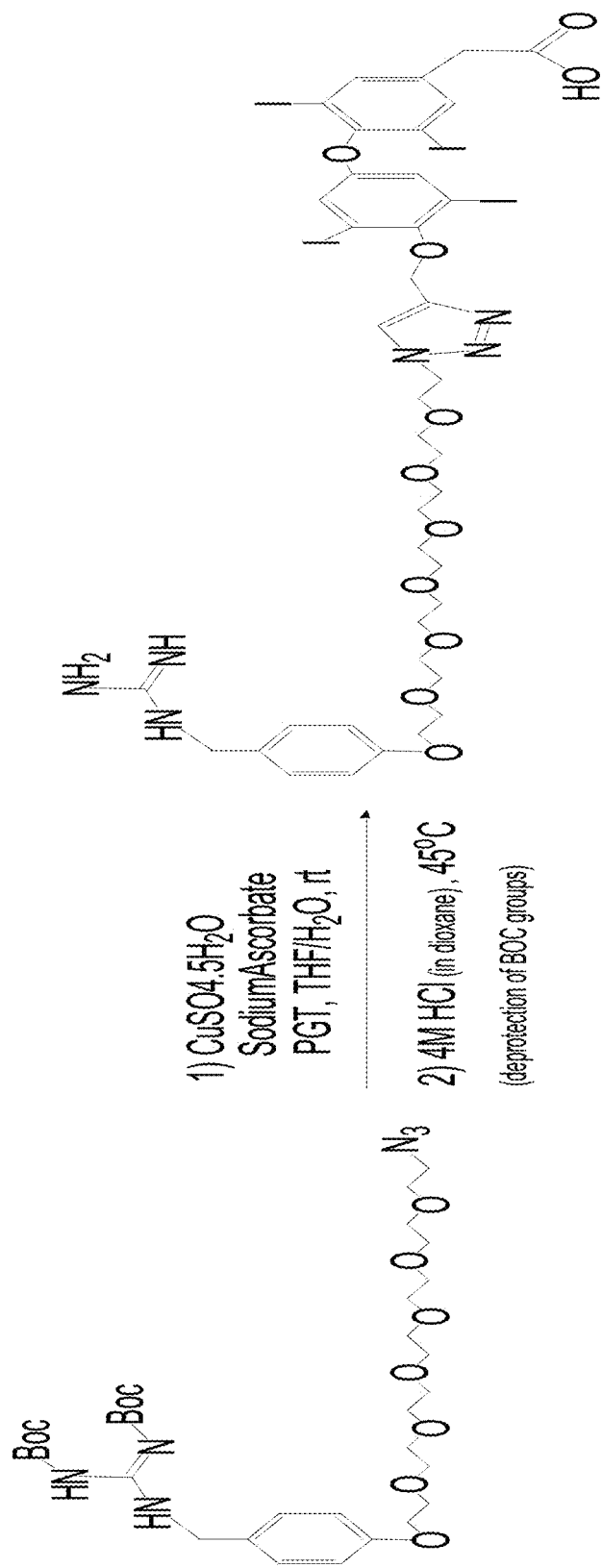
FIG. 4a depicts an overview of a synthetic pathway for Composition 300 from FIG. 3.

FIG. 4a depicts an overview of a synthetic pathway for Composition 300.

Figure 4B:
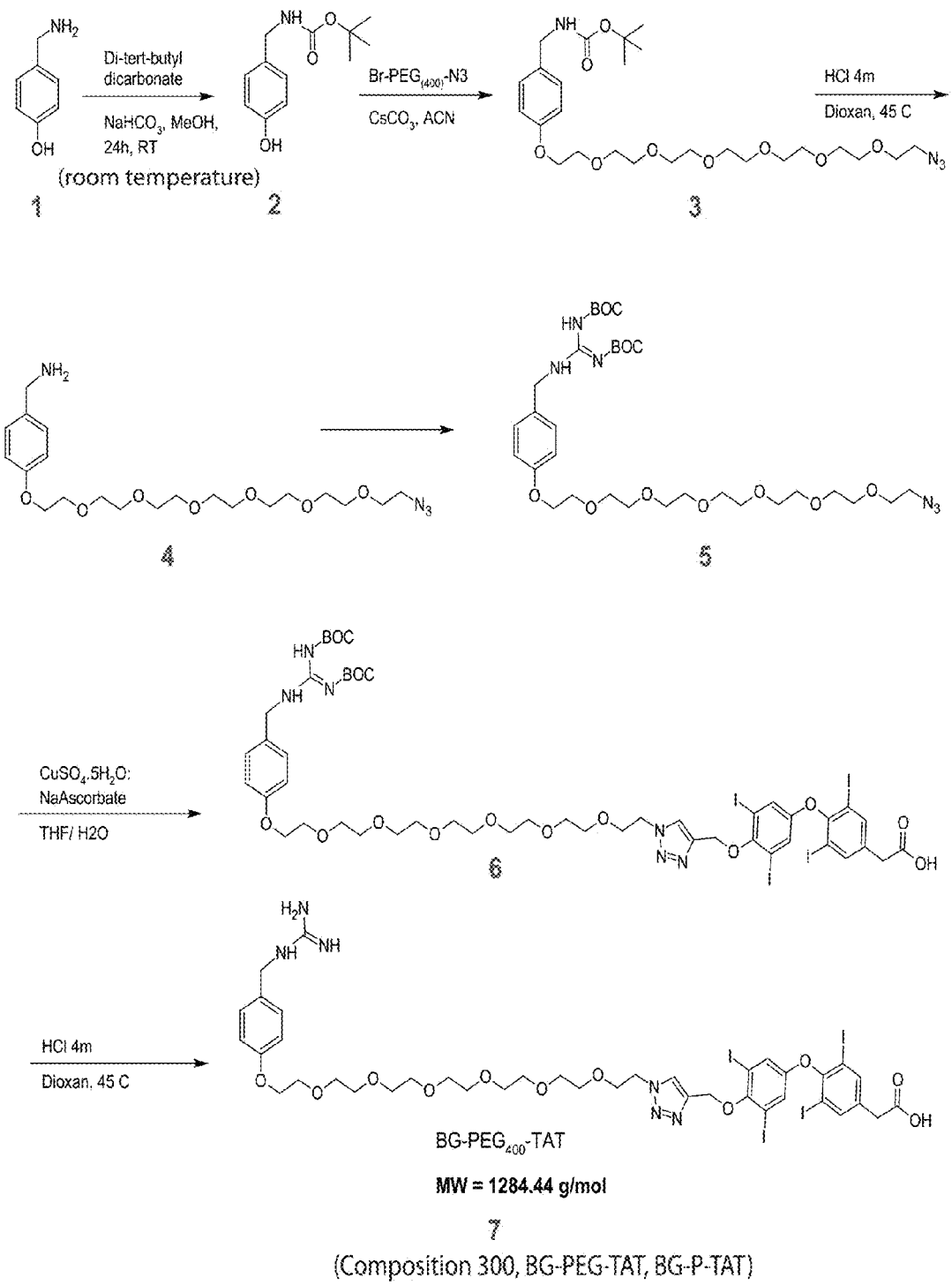

FIG. 4b depicts a detailed schematic of the synthetic pathway from FIG. 4a. FIG. 4a shows the scheme of synthesis of Composition 300 as an example of conjugation of tetrac analogs to benzyl guanine modified PEG via click chemistry. Other synthetic pathways may be used.

The individual steps of the scheme of synthesis of Composition 300 shown in FIG. 4b will be described in more detail below in which the intermediary products are referred to by the number shown in the click chemistry scheme.

Synthesis of Heterobifunctional PEG

Although heterobifunctional linker is commercial αvailable, for the purposes of this example the following synthetic route for preparation is used:

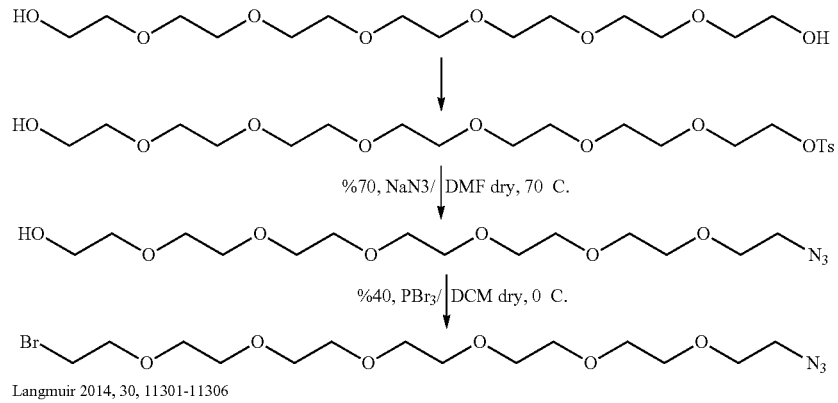

Langmuir 2014, 30, 11301-11306

Synthesis of Product 2 tert-butyl [(4-hydroxyphenyl)methyl]carbamate 2

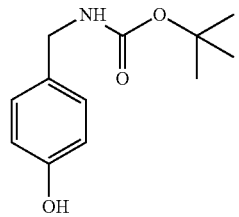 [SMILES: CC(C)(C)OC(=O)NCc1ccc(O)cc1]

Tert-butyl [(4-hydroxyphenyl)methyl]carbamate was synthesized according to the protecting method previously published {1) ACS Medicinal Chemistry Letters, 8(10), 1025-1030; 2017. 2) European Journal of Medicinal Chemistry, 126, 384-407; 2017. 3) Tetrahedron Letters, 47(46), 8039-8042; 3006} the contents of which are hereby incorporated by reference. Product 1,4-Hydroxybenzylamine (0.62 g, 5 mmol) slowly added with stirring to a solution of di-tert-butyl dicarbonate (1.2 g, 5.1 mmol) at room temperature. After the reaction mixture was stirred for 8 h, the oily residue was purified by column chromatography [SiO2: EtOAc/hexanes (1:4)] to afford 0.82 g of N-Boc-4-hydroxybenzylamine as a colorless oil with 71% yield.

Synthesis of Product 3 Etherification of tert-Butoxycarbonyl-4-hydroxybenzylamine to Bromo-Azido Modified PEG(400) 3

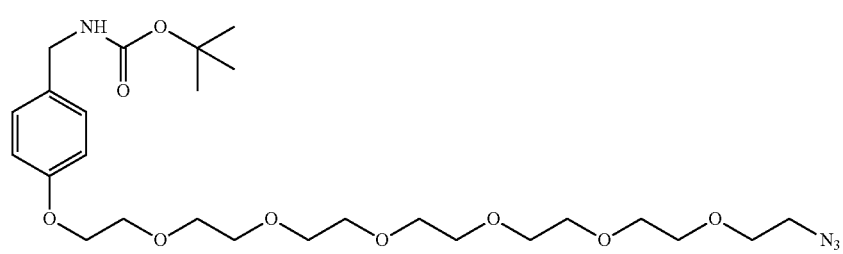

3

CsCO3 (867 mg, 2.67 mmol, 3 eq) was added with stirring to a solution of tert-Butoxycarbonyl-4-hydroxybenzylamine (300 mg, 0.896 mmol, 1 eq) in CAN (25 mL) at room temperature. After the reaction mixture was stirred for 30 min, Bromo-azido modified PEG(400) (445 mg, 1.05 mmol, 1.2 eq) added to mixture and then temperature increased till reflux for 24 h. It was filtered to remove excess of CsCO3. The solvents were removed under reduced pressure, and the oily residue was purified by column chromatography [SiO2:EtOAc/hexanes (5:5)] to afford product 3 as a yellow oil. Yield: 433 mg, 87%.

Synthesis of Product 4. BOC De Protection

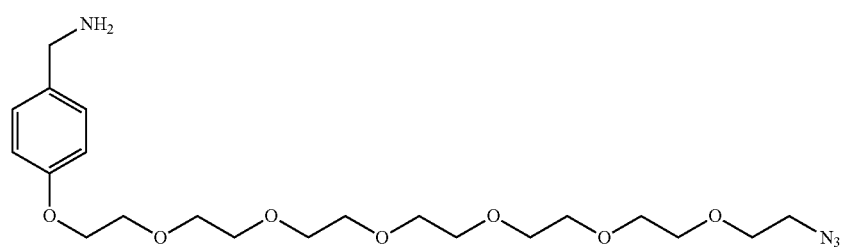

4

Product 3 (100 mg, 0.179 mmol, 3 eq) was dissolved in 3 ml anhydrous 1,4-dioxane and 3 ml HCl (4N in dioxane) added to it and stirred at room temperature. After 24 hours, the solvent was removed under reduced pressure, and the oily residue was purified to afford product 4 as a yellow oil in quantitative yield (Yield: 73 g, 90%)

Synthesis of Product 5. Guanidination of Product 4

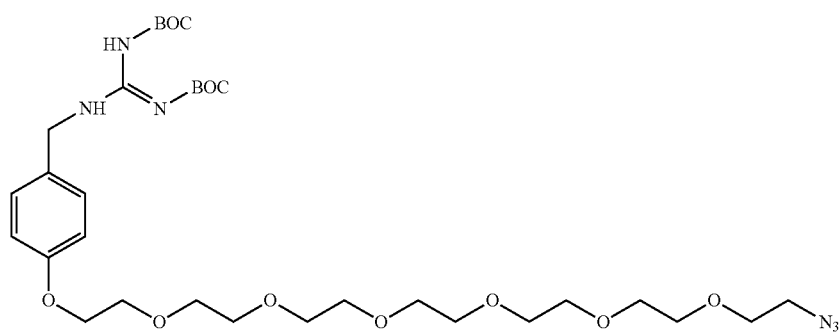

5

Product 4 (85 mg, 0.17 mmol, 1 eq), N,N'-Di-Boc-1H-pyrazole-1-carboxamidine (54 mg, 17 mg, 1 eq) was dissolved in 3-4 ml anhydrous diethylcarbodiimide "DCM" and then triethyl amine "TEA" (48 µl, 0.35 mmol, 2 eq) was added to the solution. The reaction mixture was stirred at room temperature for 12 h. After completion of the reaction the solvent was removed under reduced pressure and the residue dissolved in EtOAc (30 ml). The organic phase washed with % 5 HCl (25 ml) and brine (25 ml) and then dried (Mg2SO4). The solvent was removed under reduced pressure to yield product 5 which was purified by column chromatography [SiO2:EtOAc/hexanes (2:8)] Yield: 92 mg, 80%.

Synthesis of Product 6

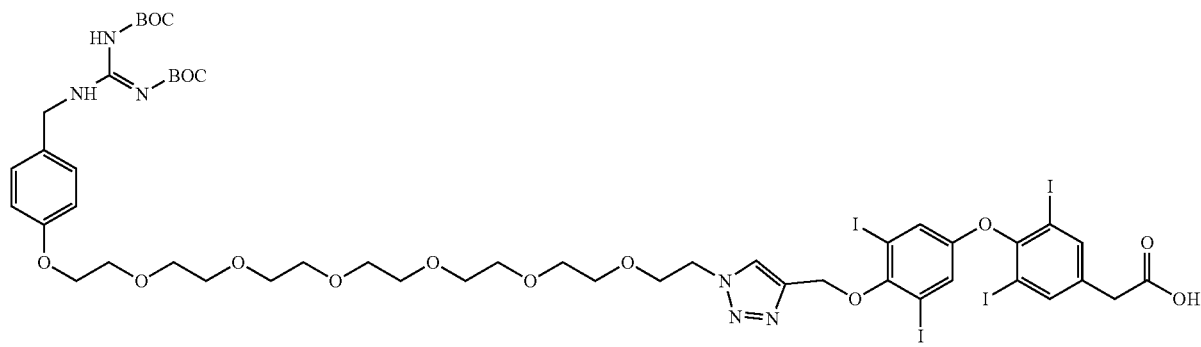

6

Product 5 (100 mg, 1 eq) and 1 eq of PGT were dissolved in 20 ml THF and stirred for 5 min then 0.5 eq of NaAscorbate and 0.5 eq of Coppersulfate in 2 ml water added to mixture and stirred for 24 hours in 65° C. After 24 hours, the solvents were removed under reduced pressure, and Product 6 purified in 65% yield.

Synthesis of Composition 300 (2-(4-(4-(0-(20-(4-(guanidinomethyl)phenoxy)-3,6,9,12,15,18-hexaoxa-icosyl)-1H-1,2,3-triazol-4-yl)methoxy)-3,5-diiodo-phenoxy)-3,5-diiodophenyl)acetic acid)

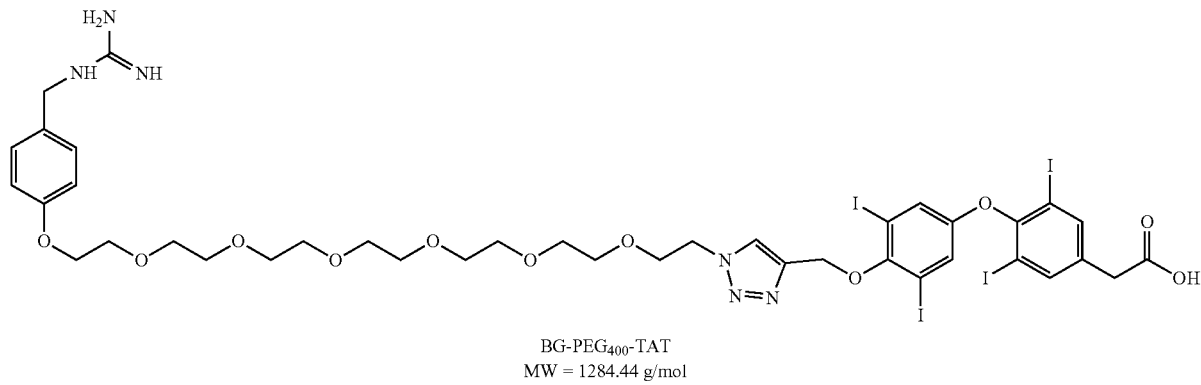

BG-PEG$_{400}$-TAT
MW = 1284.44 g/mol

Product 6 (50 mg) was dissolved in 3 ml anhydrous 1,4-dioxane and 3 ml HCl (4N in dioxane) added to it and stirred at 40 C. After 24 hours, the solvent was removed under reduced pressure, and the oily residue was purified to afford Composition 300 as a yellow powder.

Other methods of synthesis may be used to reach Composition 300 or to reach other compositions having the general formula 100 shown in the FIG. 1.

Example 1b: Synthesis of Additional Exemplary Compositions

Figure 4C:
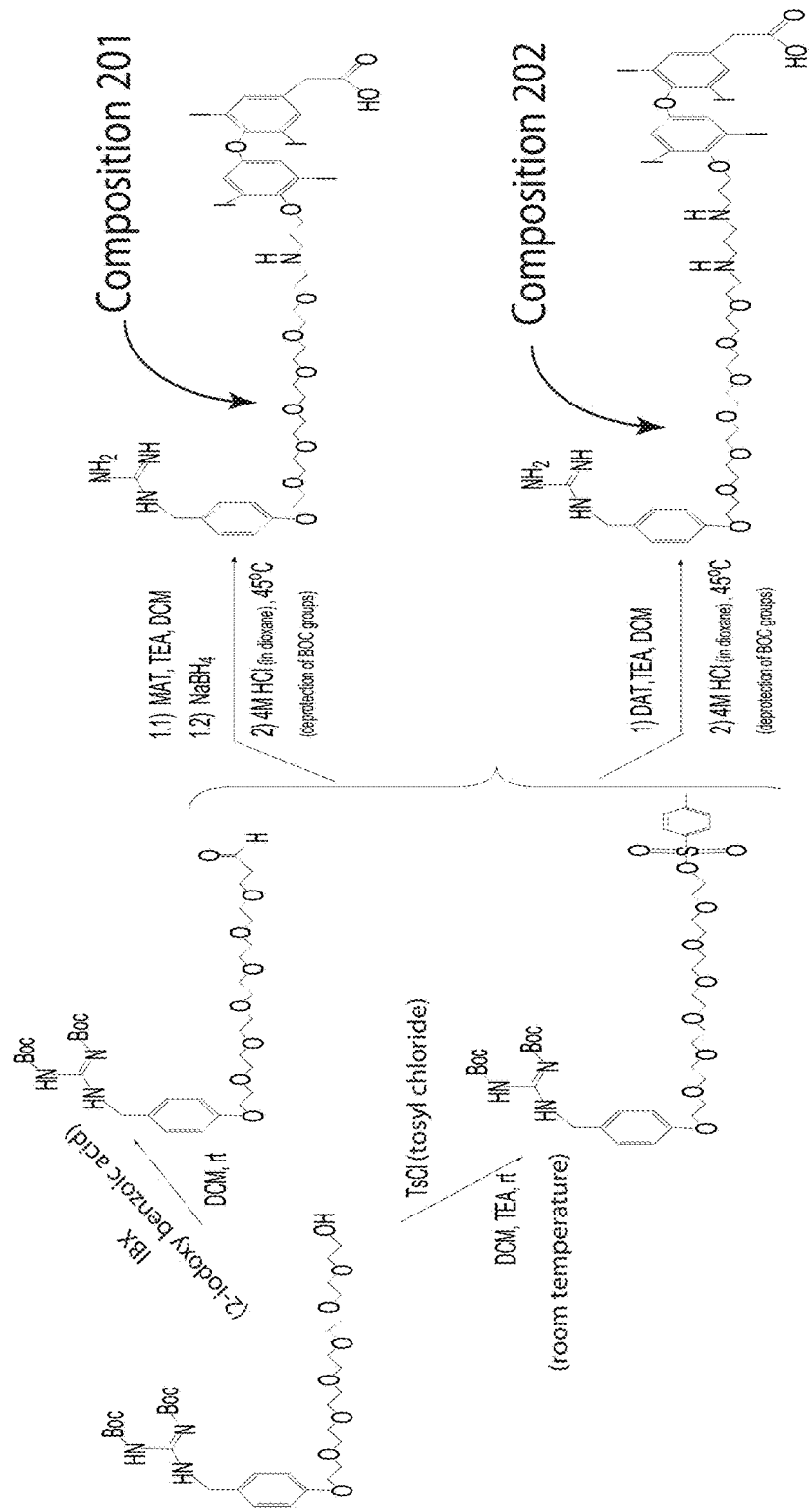
FIG. 4c depicts an overview of possible synthetic pathways for the production of two other exemplary compositions, referred to as Composition 201 (BG-PEG-MAT) and Composition 202 (BG-PEG-DAT), in which the production uses either a tosylate group or an aldehyde.
Figure 4D:
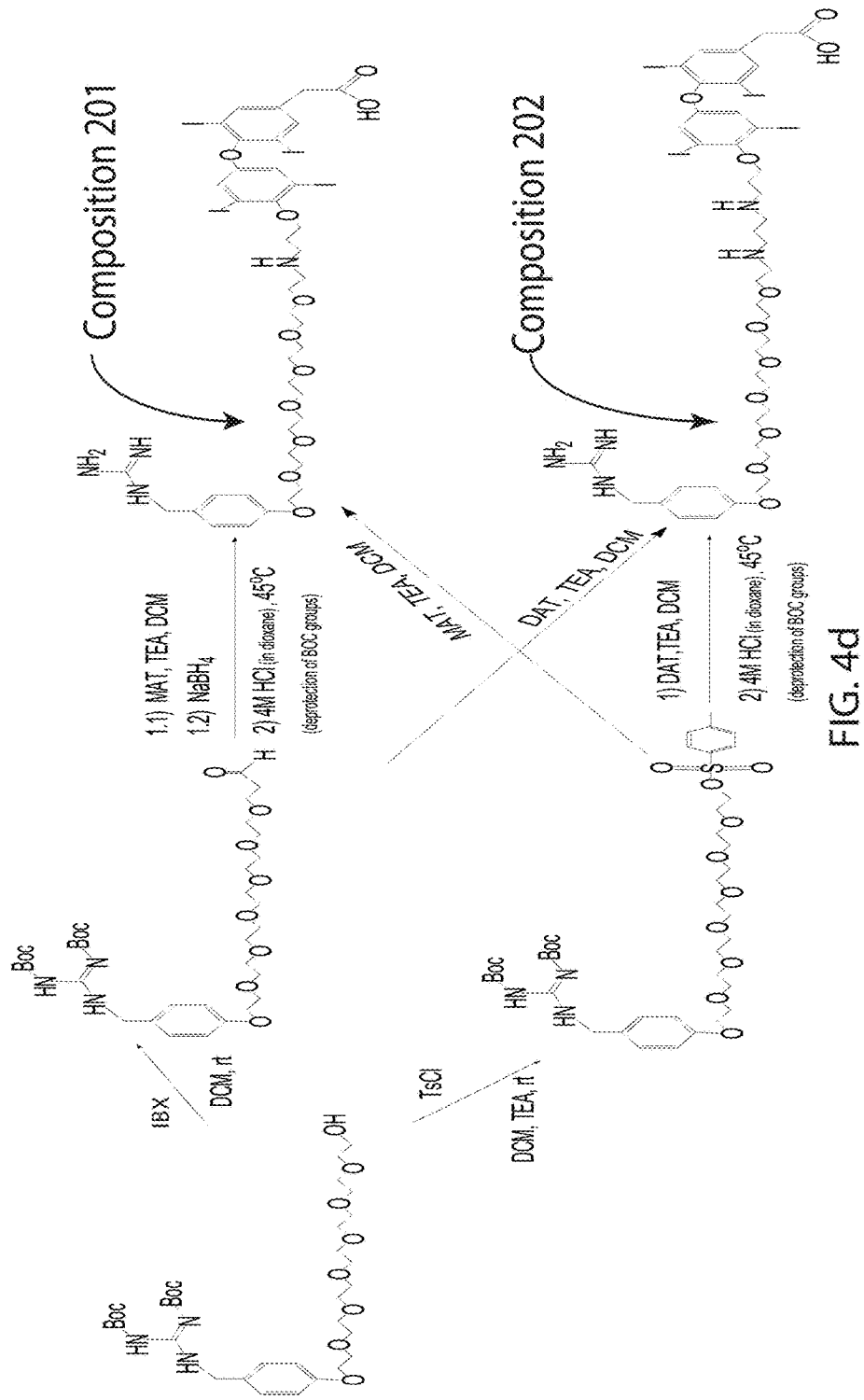
FIG. 4d depicts an overview of alternative synthetic pathways for the production of the compositions shown in FIG. 4c in which the production uses either a tosylate group or an aldehyde.

FIGS. 4c and 4d depict overviews of synthetic pathway for other exemplary compositions, for example Composition 201 following the general formula 200a and Composition 202 following the general formula 200b, using either a tosylate group or an aldehyde.

Composition 201 may be referred to as BG-P-MAT, BG-PEG-MAT, or benzyl guanidine conjugated to monoaminotetrac via PEG. Composition 202 may be referred to as BG-P-DAT, BG-PEG-DAT, or benzyl guanidine conjugated to diaminotetrac via PEG. Benzyl guanidine derivatives or other norepinephrine transport targets may be used as described herein. Tetrac derivatives or other thyrointegrin antagonists may also be used as described herein, including but not limited to triac and triac derivatives.

Figure 4E:
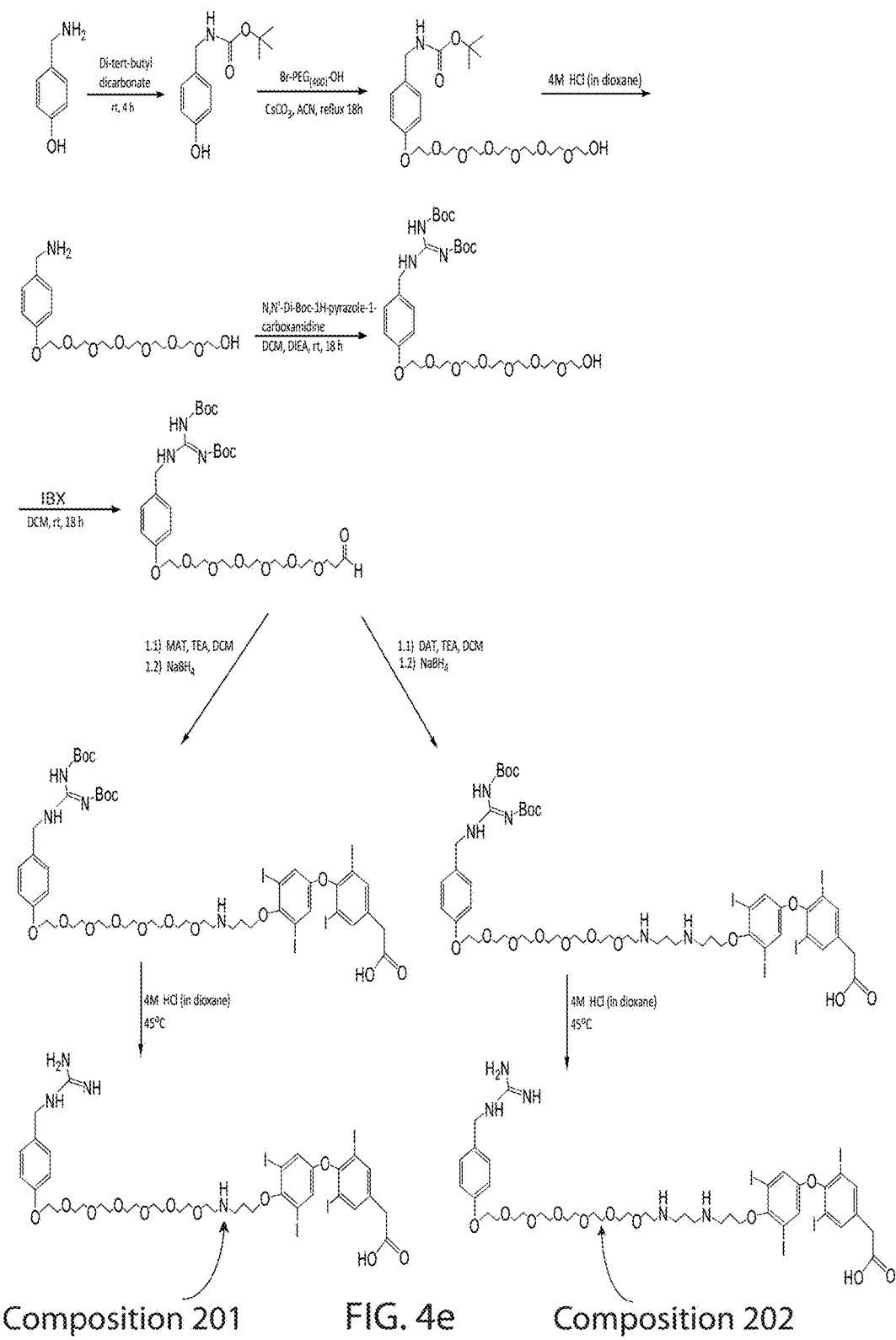
FIG. 4e depicts a detailed schematic of the synthetic pathways of FIGS. 4c and 4d that use an aldehyde.
Figure 4F:
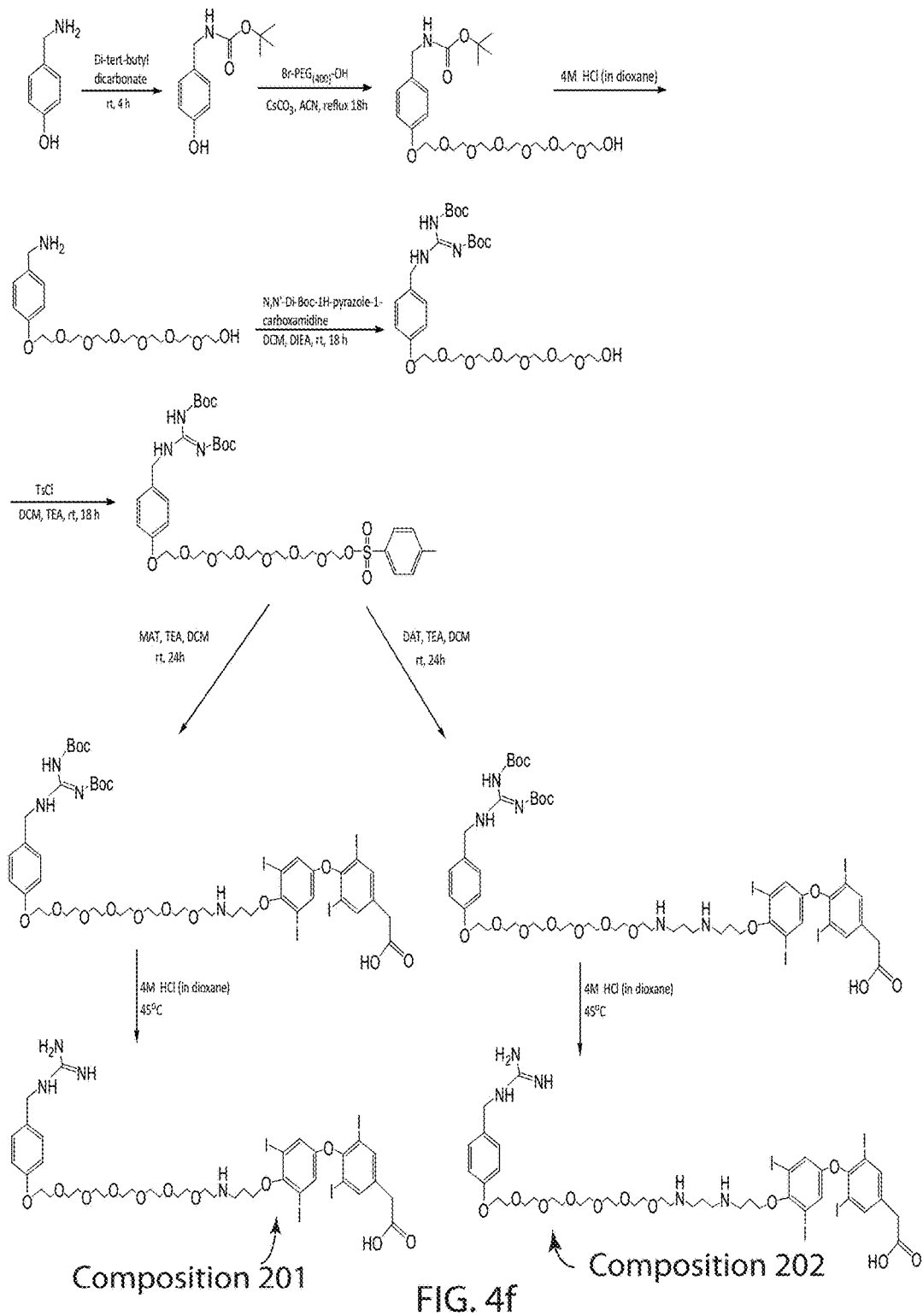
FIG. 4f depicts a detailed schematic of the synthetic pathways of FIGS. 4c and 4d using a tosylate group.

FIGS. 4e and 4f depict detailed schematics of the synthetic pathway from FIGS. 4c and 4d. FIGS. 4e and 4f shows the scheme of synthesis of Compositions 201 and 202 as further examples of conjugation of tetrac analogs to benzyl guanine modified PEG via click chemistry. Again, other synthetic pathways may be used.

Methods of Use

The compositions disclosed herein (including but not limited to the exemplary compositions such as Composition 300, Composition 201, and Composition 202) demonstrate novel dual targeting in treatment of cancer cells and tumors, particularly in treatment of neuroendocrine tumors such as neuroblastoma, pheochromocytoma, pancreatic neuroendocrine tumors, and carcinoid tumors. Further, the compositions show increased efficacy against neuroendocrine tumor cells when compared with thyrointegrin antagonist or nor-epinephrine transporter targets used or administered separately, i.e., not conjugated into a single composition.

The compositions may also be used for imaging of cancer cell/tumors. For example, the compositions described herein may be used to image neuroblastoma, pheochromocytoma, pancreatic neuroendocrine tumors, and carcinoid tumors. Imaging may be desirable for diagnosis and/or for treatment monitoring. Moreover, the compositions may be used for simultaneous treatment and imaging. For example, the compositions may demonstrate increased retention in the targeted cancer cells/tumors, allowing for enhanced treatment and more effective imaging.

Example 2: Effect on Subcutaneously Implanted Tumor in Female Nude Mice

The efficacy of Composition 300 (BG-P-TAT) was tested using neuroblastoma SKNF2 cells implanted into nude female mice.

Fifteen (15) female nude mice were implanted with twice with 10$^6$ cells/implant. The SKNF2 cell line was used with subcutaneous xenografts.

Eight (8) days following implantation, the mice were divided into four groups receiving the following treatment for 15 days:

| Group | Treatment Compound | Dosage |
| --- | --- | --- |
| Group 1 | Control - PBS | |
| Group 2 | Composition 300 (BG-PEG-TAT) | 1 mg/kg |
| Group 3 | Composition 300 (BG-PEG-TAT) | 3 mg/kg |
| Group 4 | Composition 300 (BG-PEG-TAT) | 10 mg/kg |

Figure 5:
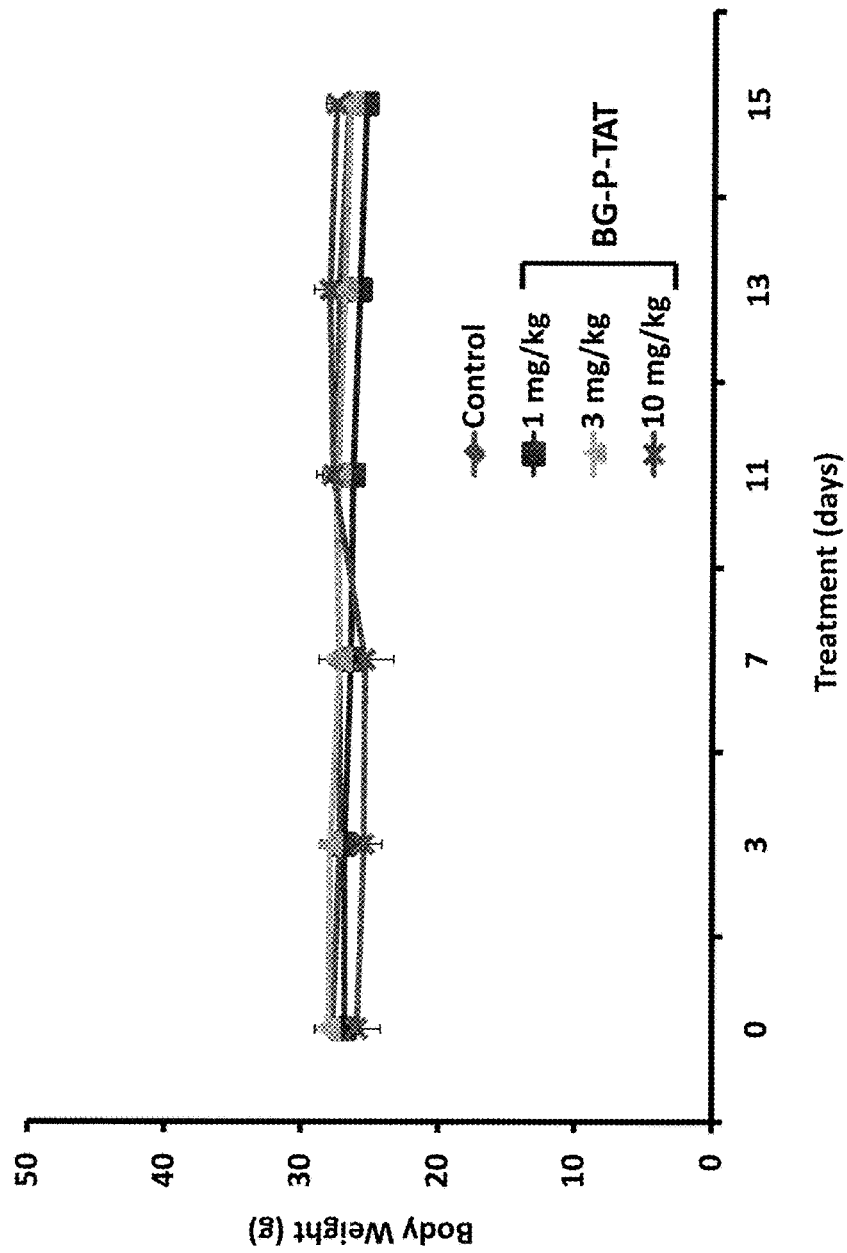
FIG. 5 depicts a graph showing no significant changes in body weight of mice during multi-day treatment with either a control or Composition 300 when administered at different doses ranging from 1-10 mg/kg subcutaneously daily for 15 days.

Following fifteen (15) days of treatment, tumors were collected in order to evaluate histopathology, and the following results were collected:

FIG. 5 shows the effect of the control and Composition 300 (BG-PEG-TAT) treatment on body weight of mice implanted with SKNF2 cell lines. As is shown, the body weight was consistent across all groups. Data demonstrate that daily treatment with Composition 300 (BG-PEG-TAT) at different doses 1, 3 and 10 mg/kg daily for 15 days have no effect on animal body weight versus control animals.

Figure 6:
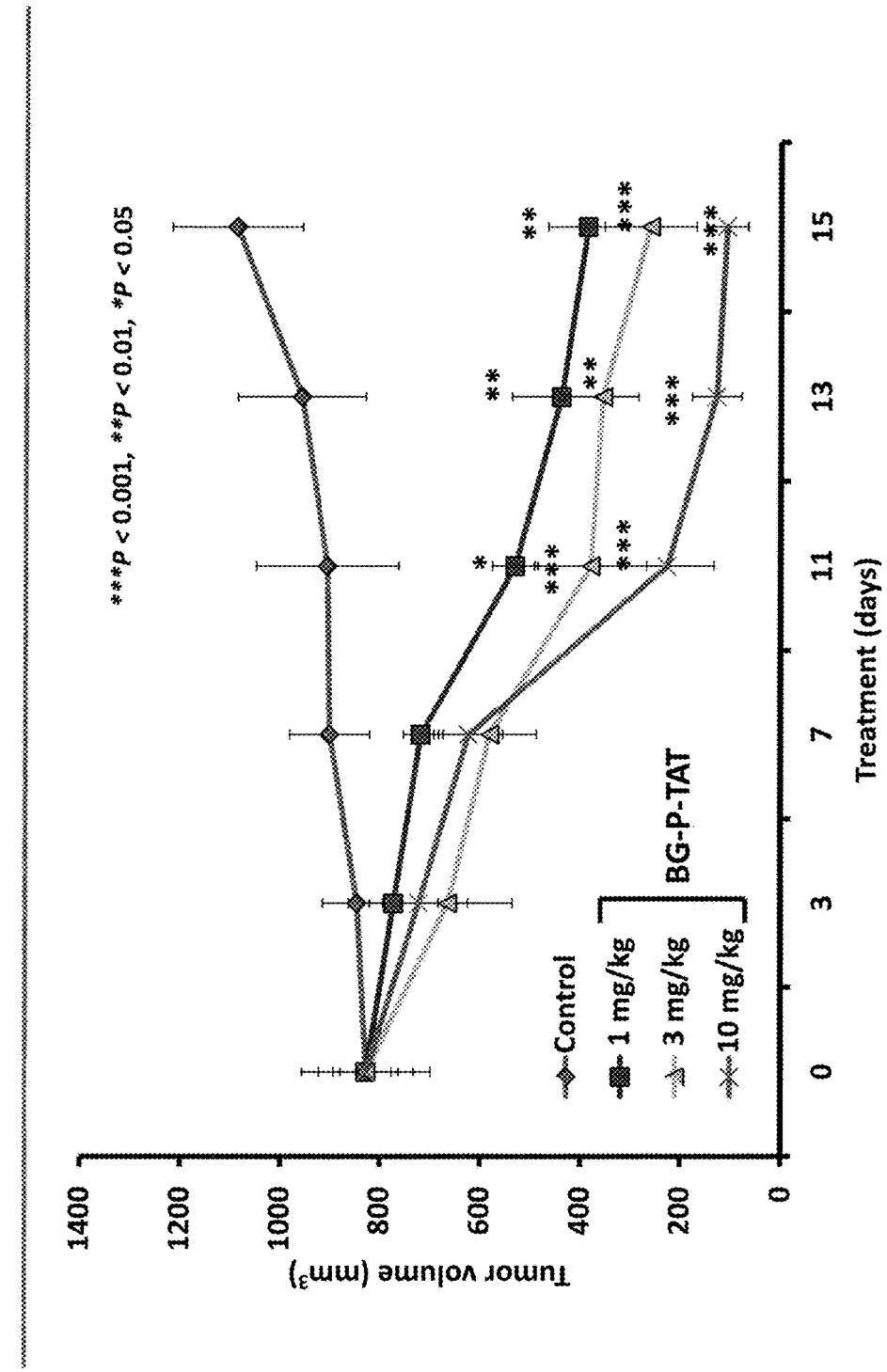
FIG. 6 depicts a graph showing dose-dependent decreases in tumor volume over time (15 days) in the mice during the multi-day treatment at 1-10 mg/kg, subcutaneously with Composition 300, compared with increase in tumor volume for a control group.

FIG. 6 shows the effect of Composition 300 (BG-PEG-TAT) treatment versus control on tumor volumes of mice implanted with SKNF2 cell lines. As shown, the control group showed an increase in tumor volume from approximately 825 mm³ to 1050 mm³ over the 15 days of treatment. All groups receiving treatment with Composition 300 (BG-PEG-TAT) showed decreased tumor size. Further, the groups receiving treatment with Composition 300 (BG-PEG-TAT) showed dose-dependent decreases in tumor size, with the 10 mg/kg Group showing a tumor size reduction from approximately 825 mm³ to 100 mm³.

Figure 7A:
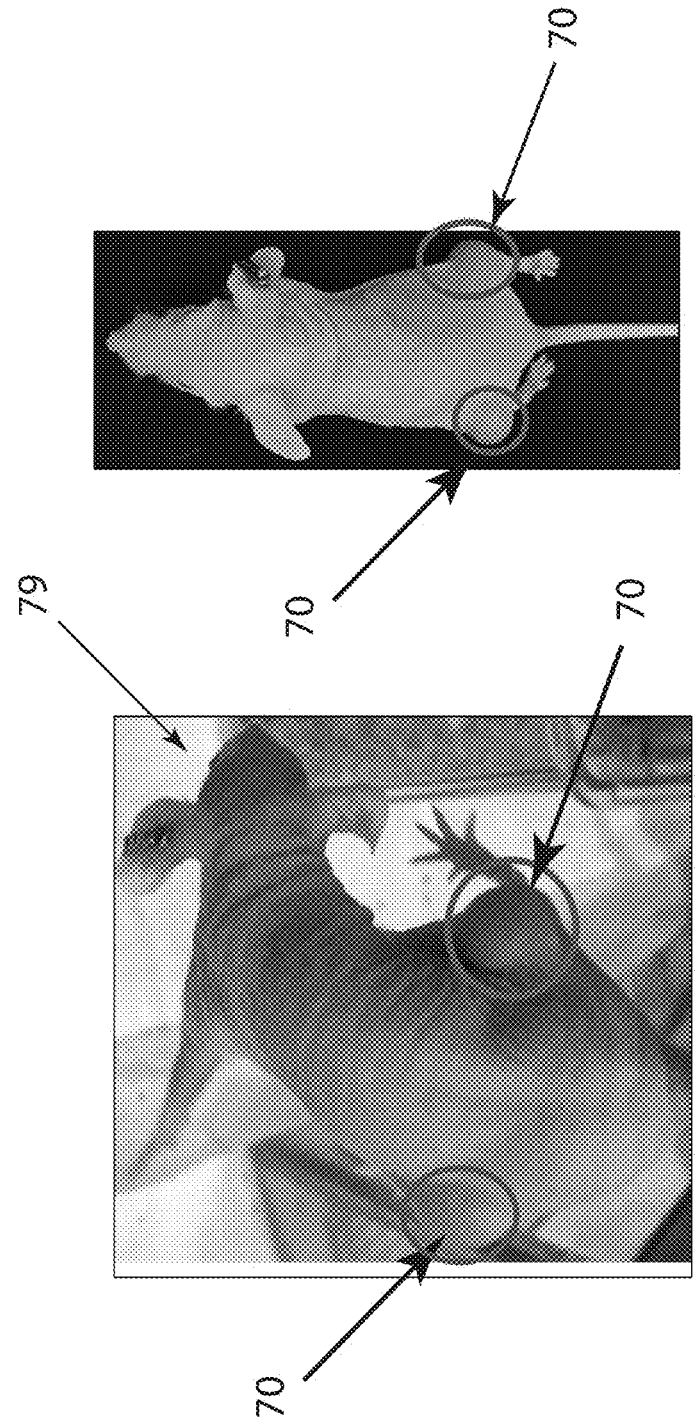
FIG. 7a shows images of mice in the control group with visible large subcutaneous tumors, along with abnormal animal head movements suggesting accompanying central behavioral changes.

FIGS. 7a-7b comprise photographs of mice from each treatment group in which subcutaneous tumors 70 can be visually compared. As shown in FIG. 7a, the control group shows large, clearly visible tumors 70. Control animals also showed abnormal circling (head rotation) 79, which was absent in all treatment arms. The abnormal circling is believed to be an effect of the tumor on the central nervous system.

As shown in FIG. 7b, the treatment groups show clear dose dependent reductions in the size of the tumors 70 to complete absence at the 10 mg/kg dose. As shown, in the 10 mg/kg treatment group there is an absence of any visible tumor at the tumor location 70'.

Figure 8:
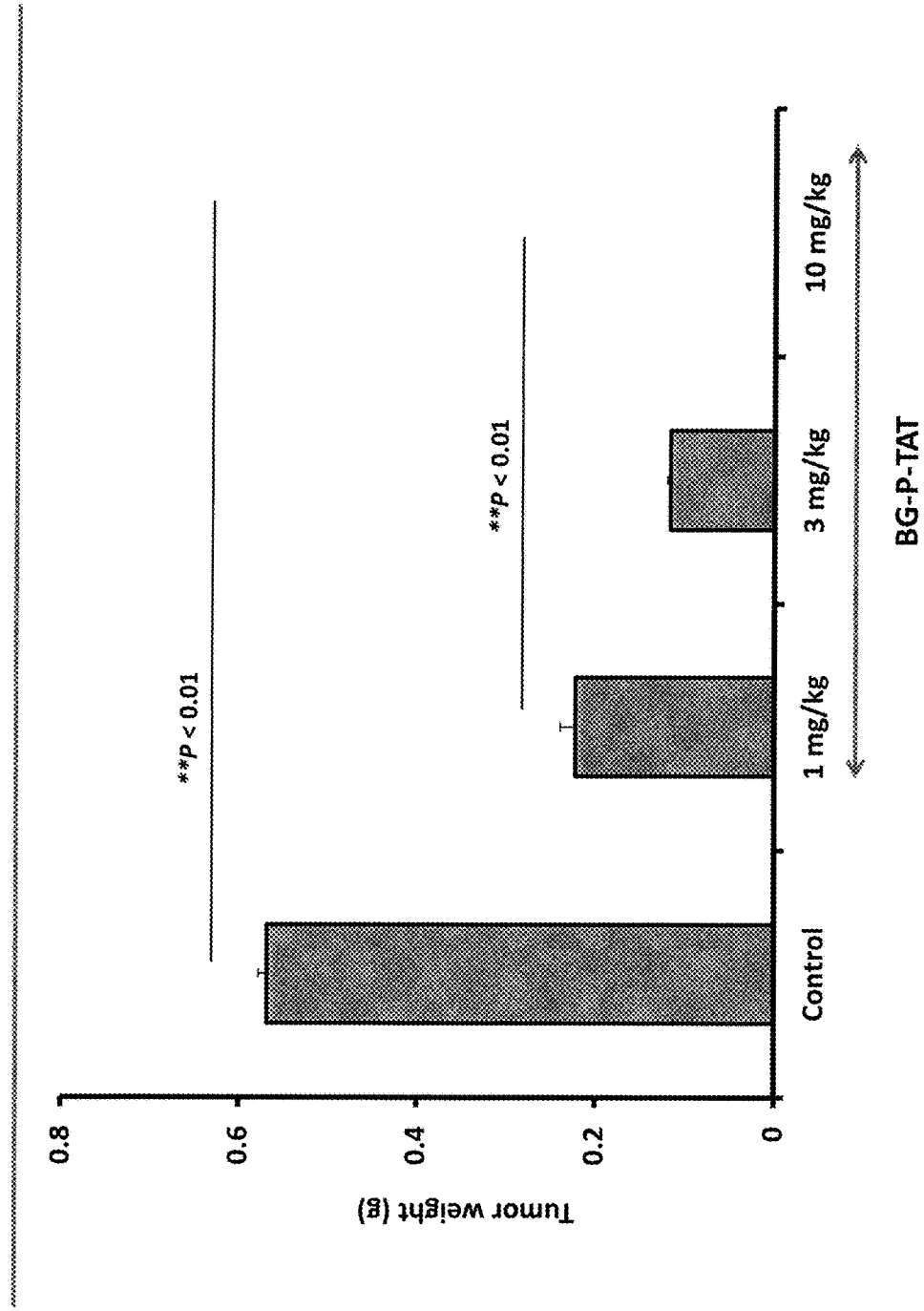
FIG. 8 is a graph of tumor weight as a function of dosage of Composition 300 showing significant tumor shrinkage to complete disappearance of the tumor.

FIG. 8 shows the effect of the control and Composition 300 (BG-PEG-TAT) treatment on tumor weight of mice implanted with SKNF2 cell lines. As can be seen, the treatment groups show a dose-dependent reduction of tumor weight in comparison with the control group. Data showed 60%, 80% and 100% tumor shrinkage at the 1, 3, ad 10 mg/kg doses, respectively.

Figure 9A:
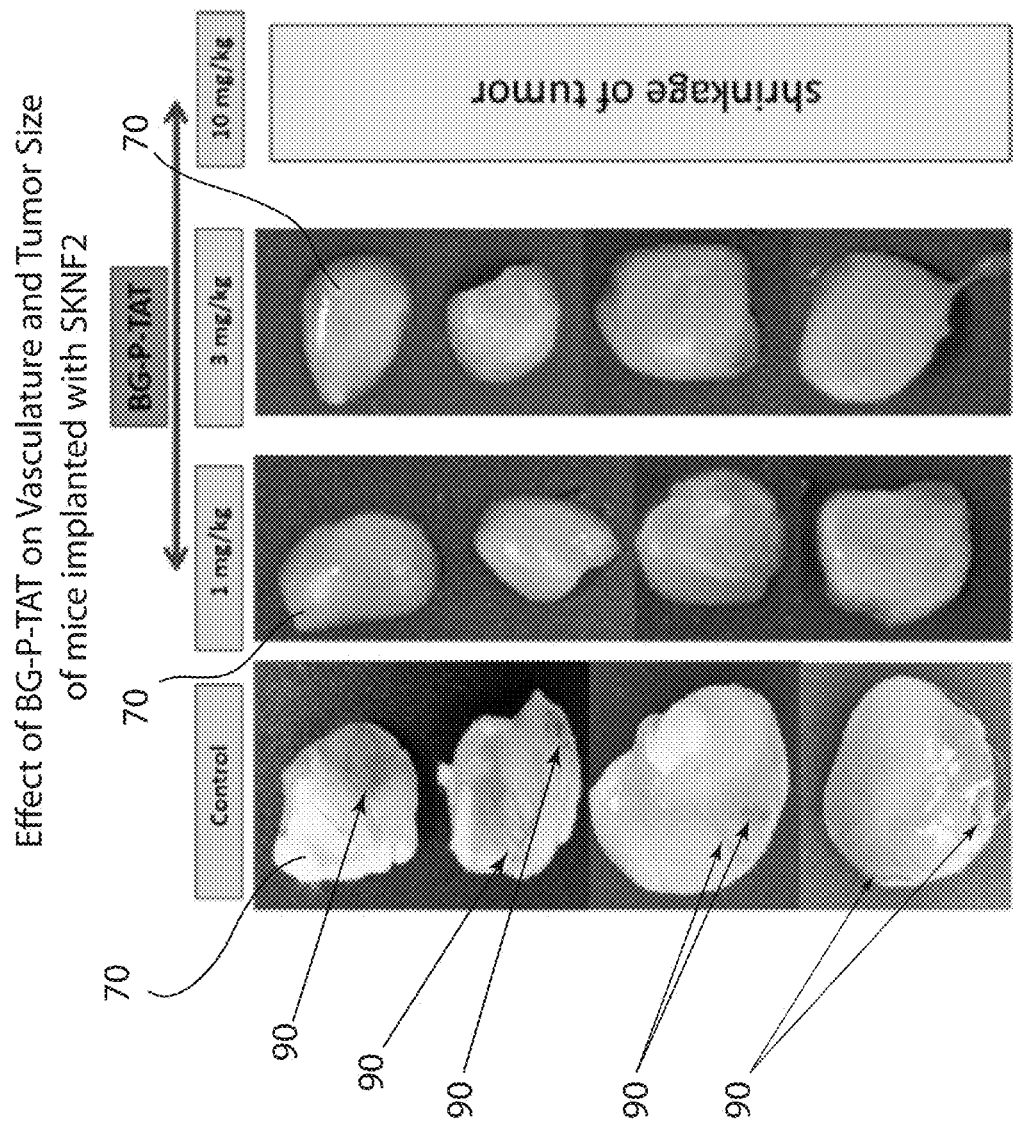
FIG. 9a are photographs of tumors showing relative tumor size and de-vascularization as a function of dosage of Composition 300.
Figure 9B:
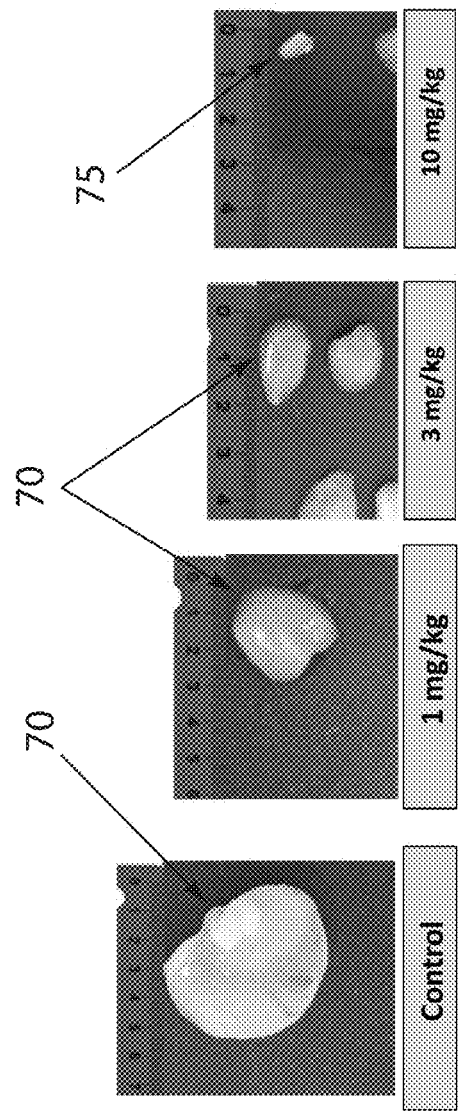
FIG. 9b are photographs of tumors showing absolute tumor size as a function of dosage of Composition 300 demonstrating distinct tumor shrinkage to disappearance at the 10 mg/kg dosage level.

FIG. 9a and FIG. 9b shows the effect of the control and Composition 300 (BG-PEG-TAT) treatment on vasculature and tumor size of mice implanted with SKNF2 cell lines. As can be seen, the control group demonstrated significant increases in size of the tumors 70 as increased vascularization. Vascularized areas 90 of the control group tumors 70 are clearly visible. In contrast, the treatment groups show a dose-dependent reduction in size of the tumors 70, including tumor shrinkage at the 10 mg/kg dose. Tumor vasculature was also clearly diminished as shown. In fact, as shown in FIG. 9b, with respect to the 10 mg/kg group, there was only necrotic skin 75 at the location of the implanted tumor 70' (see FIG. 7b) to be removed for histopathological examination; the treatment demonstrated tumor shrinkage at this dose.

Figure 10:
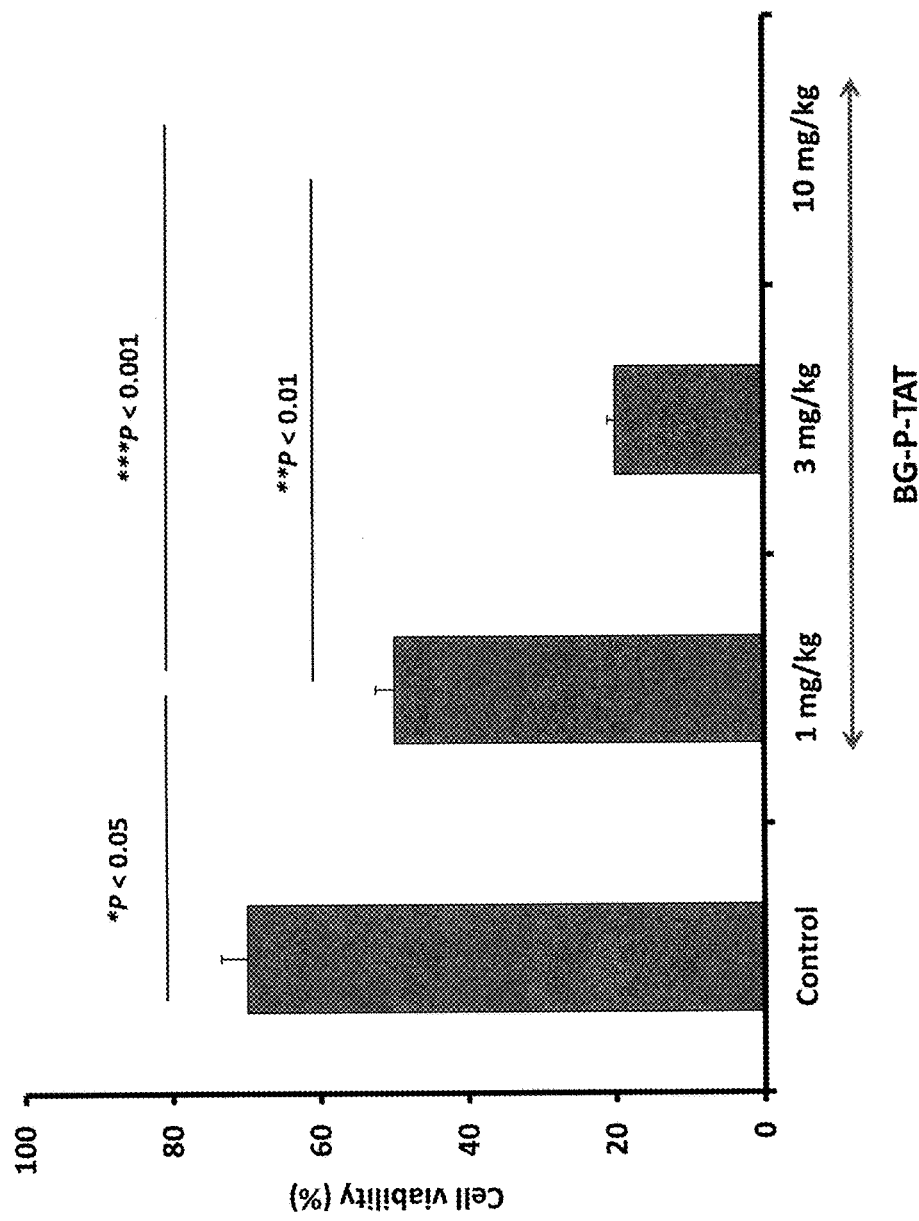
FIG. 10 is a graph of neuroblastoma cancer cell viability as a function of dosage of Composition 300 showing loss of cancer cell viability to complete loss at the 10 mg/kg dosage level.

FIG. 10 shows the effect of the control and Composition 300 (BG-PEG-TAT) treatment on tumor cell viability of mice implanted with SKNF2 cell lines. As can be seen, the treatment groups show a dose-dependent reduction in tumor cell viability. 70-75% cell viability was shown in control with 20-30% necrosis in the center of the tumor. In contrast, Composition 300 (BG-PEG-TAT) treatment at different doses showed loss of cell viability to 50%, 20, and 0.00% at 1, 3, and 10 mg/kg, daily treatment for 15 days, respectively. The 10 mg/kg group demonstrated a total lack of viable tumor cells following fifteen (15) days of treatment.

Figure 11:
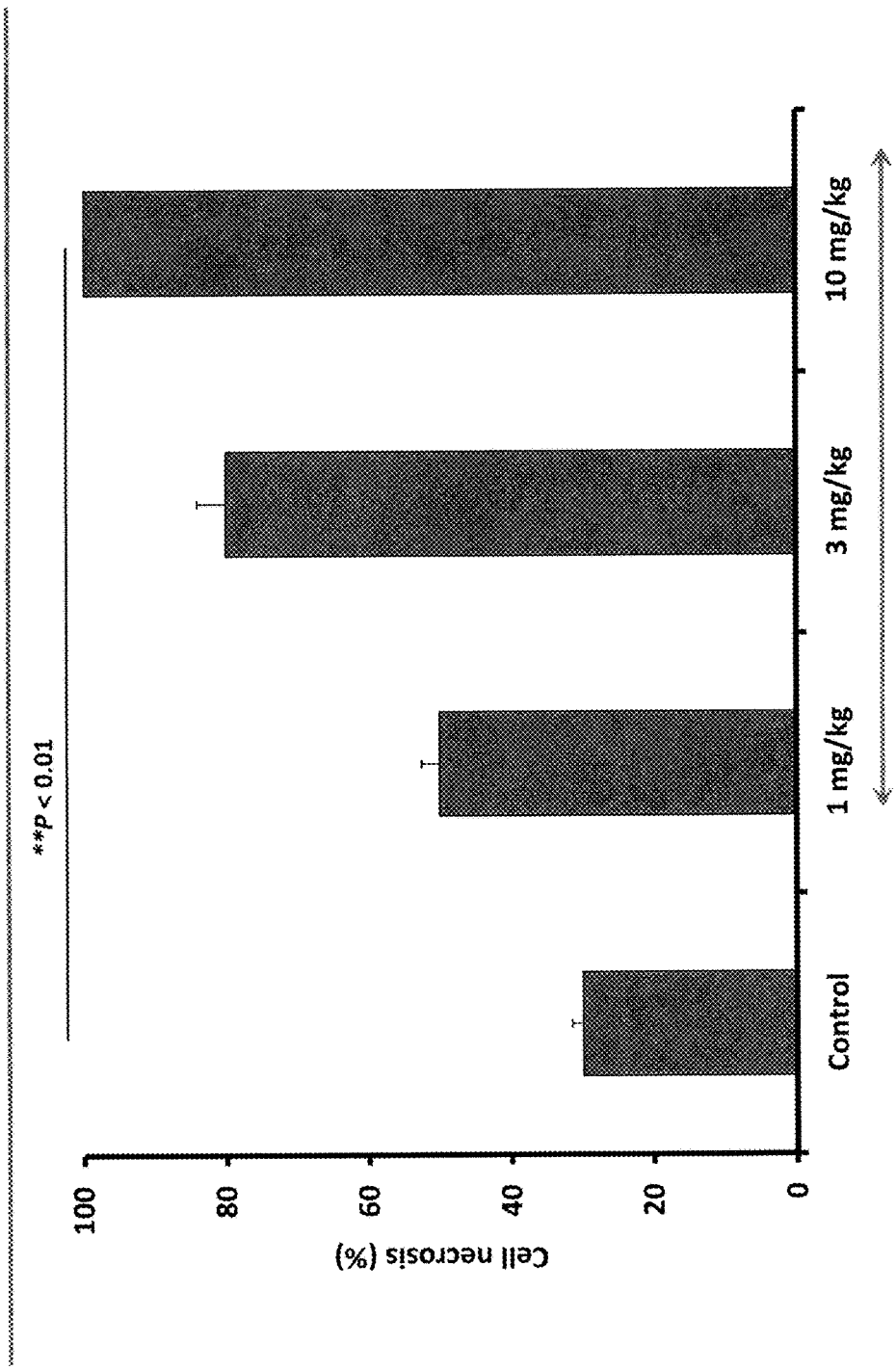
FIG. 11 is a graph of neuroblastoma cancer cell necrosis as a function of dosage of Composition 300 showing increase in cancer cell necrosis from 80-100% at the 3 and 10 mg/kg doses.

FIG. 11 shows the effect of the control and Composition 300 (BG-PEG-TAT) treatment on tumor cell necrosis of mice implanted with SKNF2 cell lines. As can be seen, the treatment groups show a dose-dependent increase in tumor cell necrosis. The 10 mg/kg group demonstrated a tumor cell necrosis rate approaching 100%, the 3 mg/kg group demonstrated a tumor cell necrosis rate of approximately 80%, and the 1 mg/kg demonstrated a tumor cell necrosis rate of approximately 50%.

Example 3: Comparative Examples

Figure 12A:
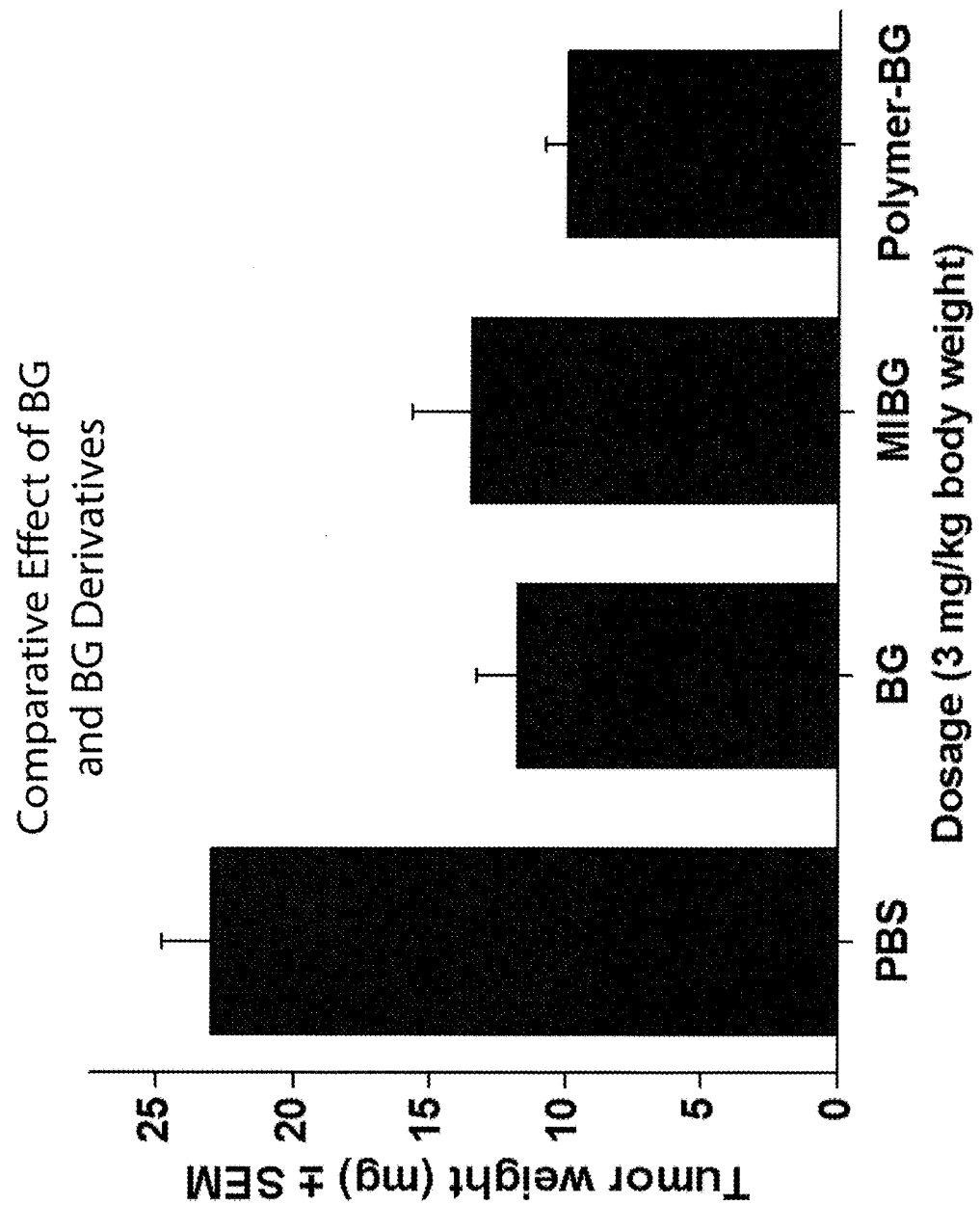
FIG. 12a is a graph of tumor weight shrinkage as a function of treatment with different benzyl guanidine derivatives including MIBG, BG, and polymer conjugated BG administered subcutaneously daily for 15 days at 3 mg/kg showing comparable shrinkage ranging from 40-50% as compared to control (PBS vehicle)
Figure 12B:
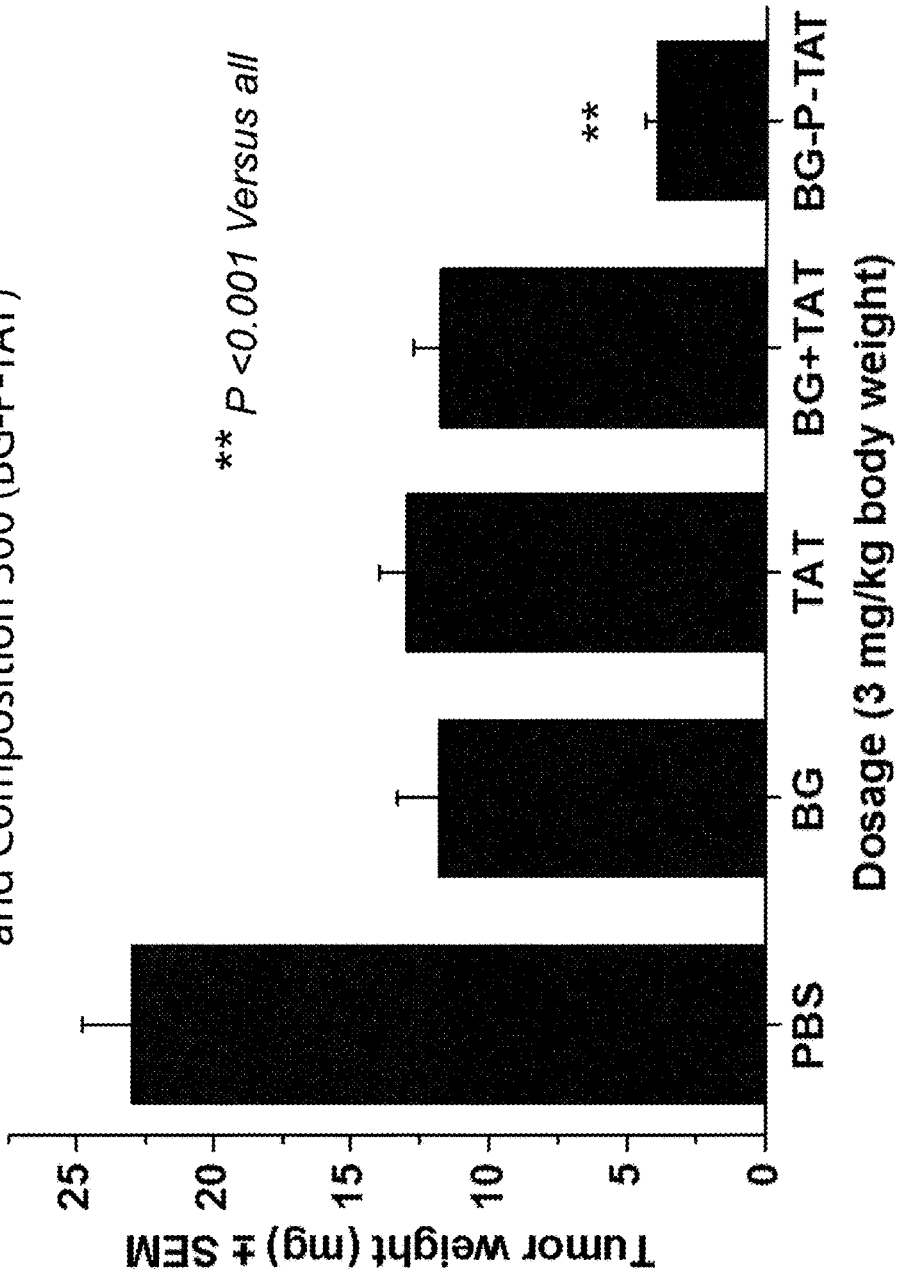
FIG. 12b is a graph of tumor weight shrinkage as a function of treatment with benzyl guanidine, TAT derivative, or BG and TAT derivative co-administered versus BG-P-TAT (Composition 300) all administered at 3 mg/kg, subcutaneously daily for 15 days (data demonstrated 40-50% tumor shrinkage with BG, TAT, or BG co-administered with TAT versus 80% shrinkage with BG-P-TAT (Composition 300) as well as maximal loss of cancer cell viability with BG-P-TAT)

FIGS. 12a and 12b shown the effect of the control and treatment with BG, BG derivatives, thyrointegrin antagonists such as TAT derivatives, and combinations (co-administration) thereof, versus Composition 300 (BG-P-TAT) on tumor cell necrosis of mice implanted with SKNF2 cell lines.

In summary, known thyrointegrin antagonists for treatment of tumor cells achieve substantially inferior results when compared with Composition 300 (BG-P-TAT). For example, triazole tetrac derivatives delivered subcutaneously daily for three (3) weeks at 3 mg/kg has been shown to reduce tumor growth by approximately 40-50% and reduce tumor viability by approximately 40-50%. Similarly, triazole tetrac derivatives have also been shown to reduce tumor growth by approximately 40-50% and reduce tumor viability by approximately 40-50%. Further, even a combination treatment of two triazole tetrac derivatives in combination delivered subcutaneously daily for three (3) weeks at 3 mg/kg only achieves a reduction of 40-50% for tumor growth and tumor viability. Similar results are obtained with treatments using benzyl guanidine and benzyl guanidine derivatives. Further, even co-administration of benzyl guanidine and thyrointegrin antagonists fails to demonstrate increased efficacy over the 40-50% mark.

In contrast, treatment with Composition 300 (BG-P-TAT) resulted in 80% reduction in tumor where the viability of residual tumor was reduced by 80%.

Comparative Example 3a: Effect of TAT Derivative on Tumor Weight

The αvβ3 integrin receptor antagonists (thyrointegrin antagonists) showed limited (40-50%) efficacy in term of tumor growth rate and cancer viability inhibition in the case of neuroendocrine tumors such as neuroblastoma, pheochromocytoma, pancreatic neuroendocrine tumors, and carcinoid tumors. For example, the graph of FIG. 12b includes the effect of a triazole tetrac derivative (referred to as TAT) on tumor weight when compared with a control group (phosphate-buffered saline "PBS"). The specific derivative tested was beta cyclodextrin triazole tetrac. As shown, the 3 mg/kg dosage resulted in approximately 40-50% reduction of tumor weight.

Comparative Example 3b: Effect of Benzyl Guanidine and Derivatives on Tumor Weight Similarly, benzyl guanidine and its derivatives demonstrate limited (40-50%) efficacy in term of tumor growth rate and cancer viability inhibition in the case of neuroendocrine tumors such as neuroblastoma, pheochromocytoma, pancreatic neuroendocrine tumors, and carcinoid tumors. For example, the graph in FIG. 12a includes the effect of benzyl guanidine (BG) and benzyl guanidine derivatives (such as MIBG and a polymer conjugated benzyl guanidine (specifically PLGA-PEG-BG, referred to as polymer-BG) on tumor weight when compared with a control group (PBS). The treatment compounds demonstrated limited anti-cancer efficacy of neuroblastoma despite its maximal (90-100%) uptake into neuroblastoma and other neuroendocrine tumors.

Comparative Example 3c: Effect of Co-Administration of Separate Norepinephrine Transporter Target and Thyrointegrin Antagonist Furthermore, treatment combinations comprising co-administration of norepinephrine transporter targets such as benzyl guanidine or derivatives together with thyrointegrin antagonists such as triazole tetraiodothyroacetic acid derivatives did not exceed 40-50% suppression of neuroblastoma growth and viability. For example, benzyl guanidine co-administered with a tetrac derivative (BG+TAT) did not surpass the 40-50% efficacy demonstrated by individual treatment with either compound as shown in FIG. 12b (BG+TAT). Again, beta cyclodextrin triazole tetrac was the tetrac derivative used.

Comparative Example 3d: Effect of Composition 300 (BG-P-TAT) (Benzyl Guanidine Conjugated to TAT Via PEG)

Again, treatment with Composition 300 (BG-P-TAT) resulted in significant improvement in the effect on tumor weight compared with both the control and other types of treatments as shown in FIG. 12b. Composition 300 achieves approximately 80% reduction in tumor. Further, the viability of residual tumor was reduced by 80%. In fact, Composition 300 (TAT conjugated to BG) demonstrated a significant increase in efficacy over even co-administration of TAT and BG separately (BG+TAT).

The comparative examples from FIGS. 12a and 12b are summarized in the following Table 3:

TABLE 3

Comparative Tumor Growth Suppression and Tumor Survival Suppression Effect

| Treatment Compound/ Composition | Dosage | Percentage of Tumor Growth Suppression | Percentage of Tumor Survival Suppression |
|---|---|---|---|
| Benzyl guanidine (BG) | 3 mg/kg | 40-50% | 40-50% |
| Metaiodobenzylguanidine (MIBG) | 3 mg/kg | 40-50% | 40-50% |
| Benzyl guanidine with Polymer (PLGA-PEG-GB) (Polymer-BG) | 3 mg/kg | 40-50% | 40-50% |
| Triazole Tetrac Derivative 1 (beta cyclodextrin triazole tetrac) (TAT) | 3 mg/kg | 40-50% | 40-50% |
| Co-Administration of Benzyl guanidine and Triazole Tetrac Derivative 1 (BG + TAT) | 3 mg/kg | 40-50% | 40-50% |
| Composition 300 (BG-P-TAT) | 3 mg/kg | 80-90% | 80-90% |

Example 4: Imaging of Subcutaneously Implanted Tumor in Athymic Female Mice

Athymic female mice were implanted twice each with $10^6$ cells/implant. The SKNF1 cell line was used with subcutaneous xenografts.

Group 1 consisted of three mice and were treated with PEG-TAT-dye (Cy5). Group 2 consisted of three mice and were treated with PEG-BG-dye (Cy5). Group 3 consisted of three mice and were treated with TAT-PEG-BG-dye (Cy5) wherein the TAT and BG were covalently linked with a PEG linker as compound 300. The treatment groups are shown below:

| Group | Treatment Composition |
|---|---|
| Group 1 | PEG modified triazole tetrac derivative with Cy5 dye |

| Group | Treatment Composition |
|---|---|
| Group 2 | PEG modified benzyl guanidine derivative with Cy5 dye |
| Group 3 | Composition 300 with Cy5 dye |

Figure 13A:
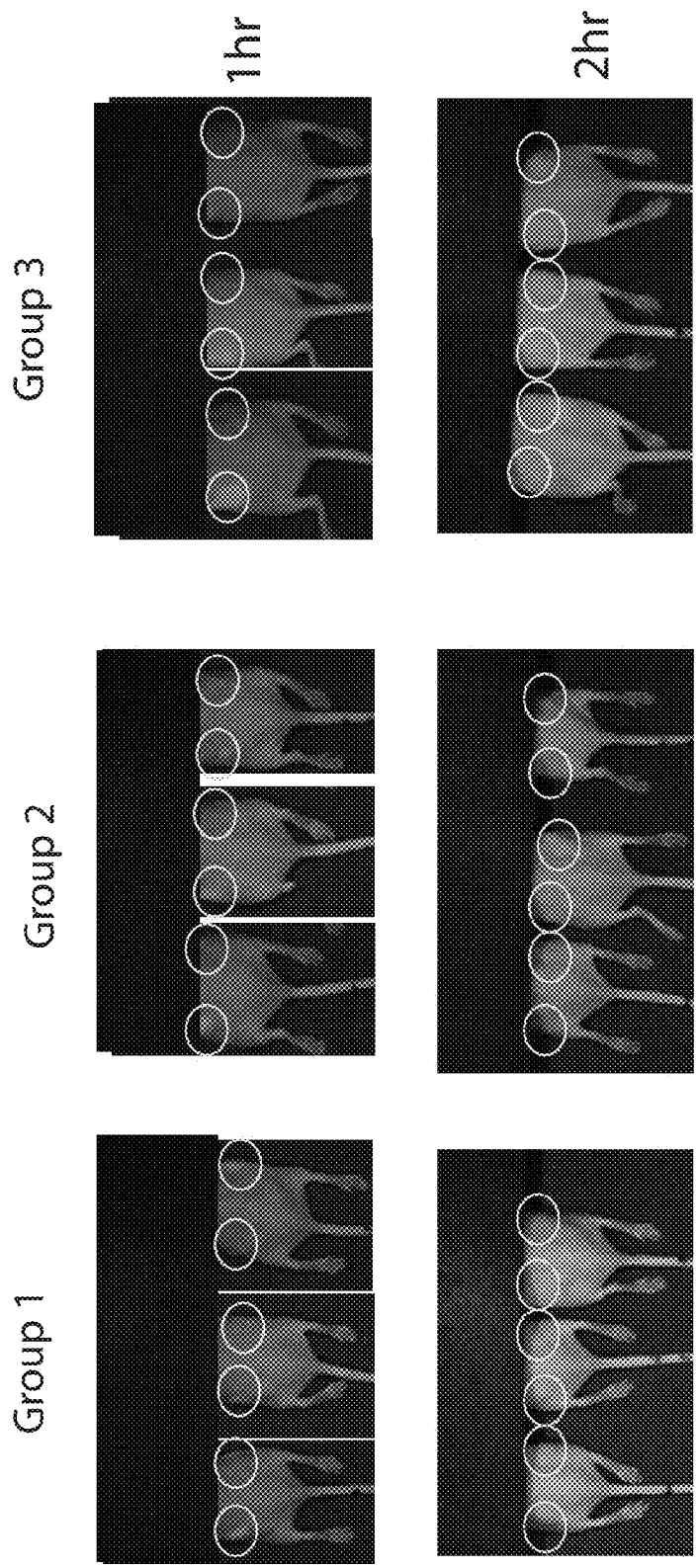
FIG. 13a are photographs of fluorescence images of various mice at 1 and 2 hours post-administration of Cy5 labeled polymer conjugated TAT (Group 1), polymer conjugated BG (Group 2), and Polymer conjugated BG-TAT (Composition 300) (Group 3)
Figure 13B:
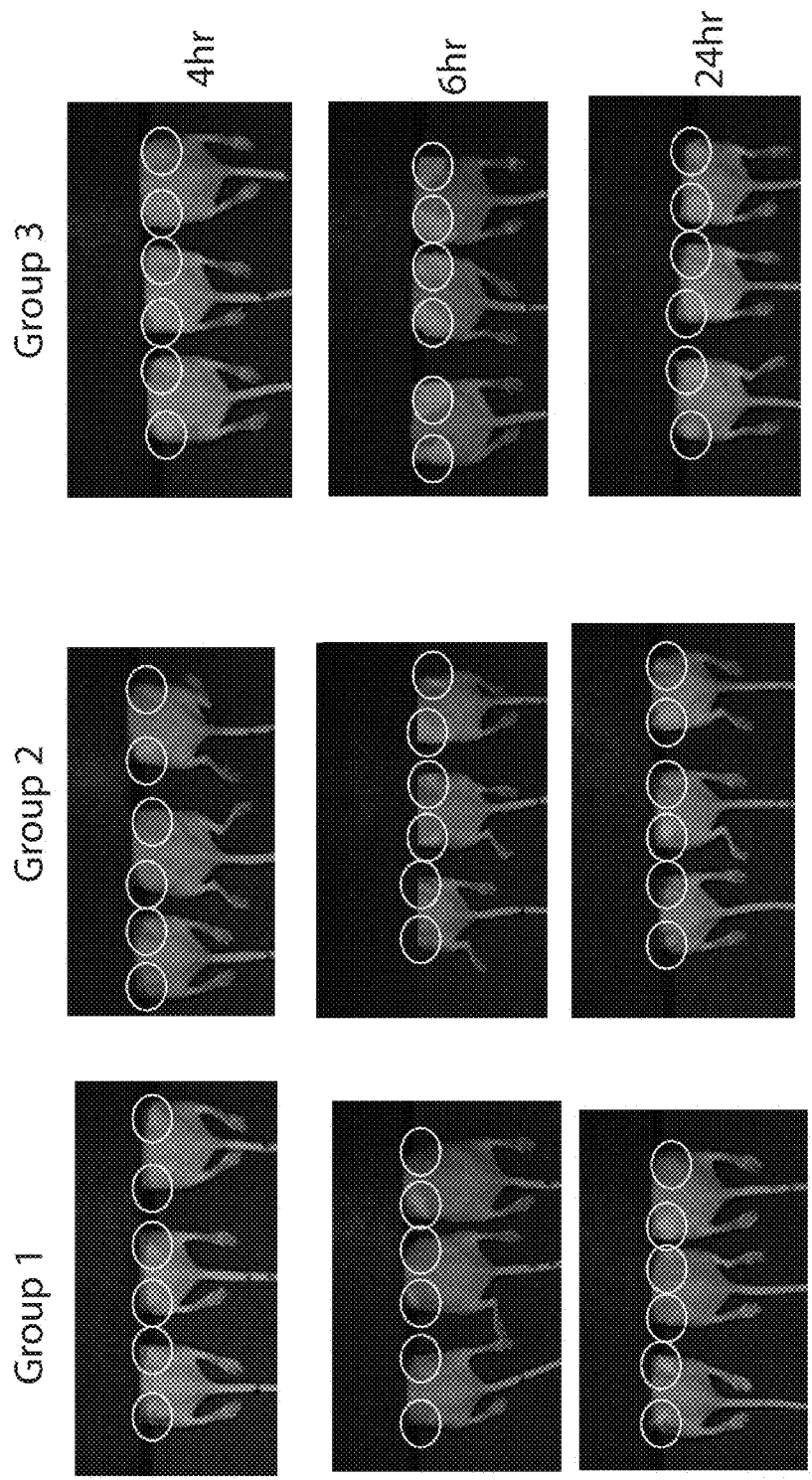
FIG. 13b are photographs of fluorescence images of the mice of FIGS. 13a at 4, 6, and 24 hours post-administration (data clearly showed distinct and highest intensity accumulation (delineation and imaging) in neuroblastoma tumor and its spread with Cy5-labeled polymer conjugated BG-P-TAT (Composition 300)).

Fluorescence imaging (Cy5) was conducted 1 hour, 2 hours, 4 hours, 6 hours, and 24 hours post-administration. Imaging results are shown in FIGS. 13a and 13b, in which the tumor location is circled in yellow and the Cy5 dye appears as red. As shown in these figures, there was a dramatic increase in the fluorescence signal when the TAT and BG were covalently linked and Composition 300 showed marked improvement in both uptake into the SKNF1 neuroblastoma tumors and retention time within the tumor when compared with either a triazole tetrac derivative alone or a benzyl guanidine derivative alone.

Neuroblastoma tumor cells were used in the treatment example discussed. Those skilled in the art would appreciate these examples are valid models for treatment of other tumor types, particularly other neuroendocrine tumors. Further, any tumor or disease state demonstrating increased activity of the norepinephrine transporter in which thyrointegrin moderated antiangiogenic activity would be desired may be treated by the disclosed compositions.

In light of these examples, the compositions described herein show increased efficacy against tumor cells, particularly neuroendocrine tumors. These compositions may be used to treat neuroendocrine tumors such as neuroblastoma, pheochromocytoma, pancreatic neuroendocrine tumors, and carcinoid tumors, for example by injectable, topical, sublingual, oral, and other routes of administration.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A composition comprising: a compound of a general formula:

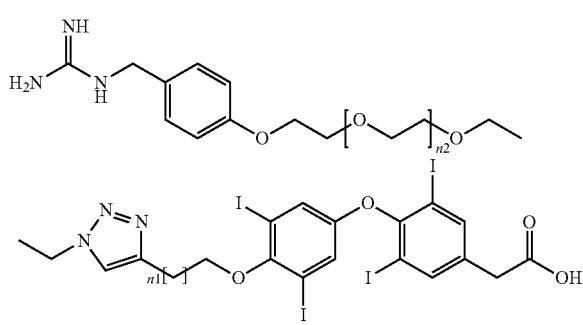

or a salt thereof;
wherein $n_1 \geq 0$ and $n_2 \geq 1$.

2. The composition of claim 1, wherein the compound has a general formula of

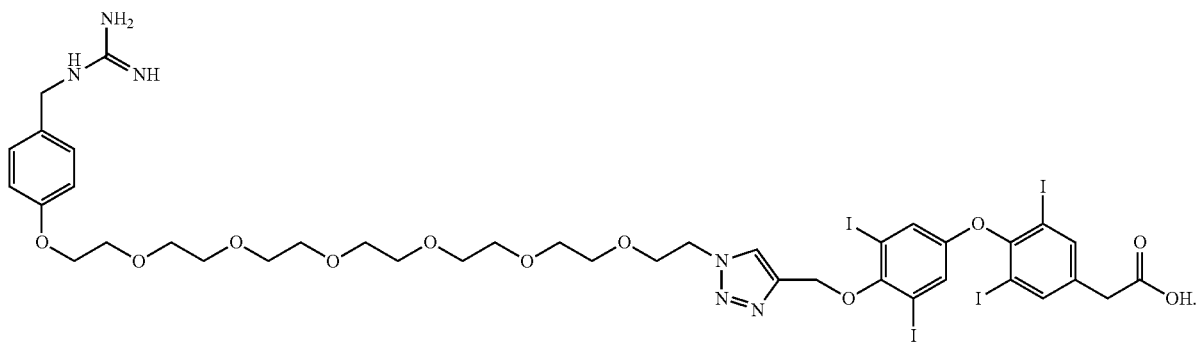

3. The composition of claim 1, wherein the composition is used for the treatment of a neuroendocrine tumor by administration in a therapeutic dose.

4. The composition of claim 1, wherein the composition has a utility for the treatment of a neuroendocrine tumor.

5. The composition of claim 4, wherein the neuroendocrine tumor is one of a neuroblastoma, pheochromocytoma, pancreatic neuroendocrine tumor, and carcinoid tumor.

6. The composition of claim 1, wherein the composition targets neuroendocrine tumor cells via a norepinephrine transporter.

7. The composition of claim 1, wherein the composition targets neuroendocrine tumor cells via binding with an integrin αvβ3 receptor.

8. The composition of claim 1, wherein the composition targets neuroendocrine tumor cells via both a) the norepinephrine transporter and b) reaction with the integrin αvβ3 receptor.

9. A method of treating a neuroendocrine tumor, comprising:

administering to a subject in need thereof a therapeutically effective amount of a composition comprising a compound having a chemical formula:

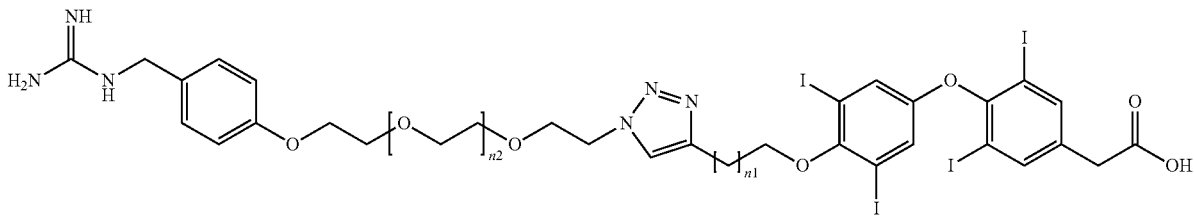

or a salt thereof;

wherein $n_1 \geq 0$ and $n_2 \geq 1$.

10. The method of claim 9, wherein the compound has a chemical formula of

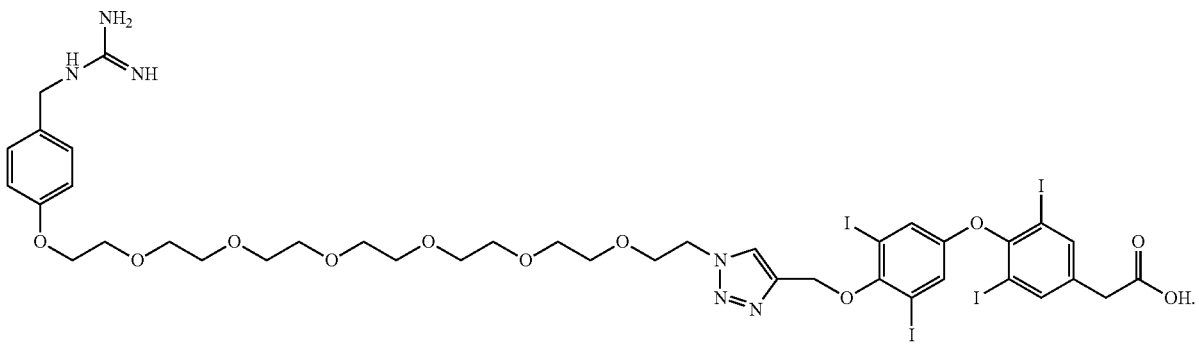 [SMILES: N=C(N)NCc1ccc(OCCOCCOCCOCCOCCOCCOCCn2cc(COc3c(I)cc(Oc4c(I)cc(CC(=O)O)cc4I)cc3I)nn2)cc1]

11. The method of claim 9, wherein the neuroendocrine tumor is one of a neuroblastoma, pheochromocytoma, pancreatic neuroendocrine tumor, and carcinoid tumor.

12. The method of claim 9, wherein the composition targets neuroendocrine tumor cells via a norepinephrine transporter.

13. The method of claim 9, wherein the composition targets neuroendocrine tumor cells via binding with an integrin αvβ3 receptor.

14. The method of claim 9, wherein the composition targets neuroendocrine tumor cells via both a) the norepinephrine transporter and b) reaction with the integrin αvβ3 receptor.

15. A composition comprising:
N-benzyl guanidine; and
triazole tetrac;
wherein the N-benzyl guanidine and the triazole tetrac are conjugated by polyethylene glycol.

16. The composition of claim 15, wherein the composition is used for the treatment of a neuroendocrine tumor by administration in a therapeutic dose.

17. The composition of claim 15, wherein the composition has a utility for the treatment of a neuroendocrine tumor.

18. The composition of claim 17, wherein the neuroendocrine tumor is one of a neuroblastoma, pheochromocytoma, pancreatic neuroendocrine tumor, and carcinoid tumor.

19. The composition of claim 15, wherein the composition targets neuroendocrine tumor cells via a norepinephrine transporter.

20. The composition of claim 15, wherein the composition targets neuroendocrine tumor cells via binding with an integrin αvβ3 receptor.

21. The composition of claim 15, wherein the composition targets neuroendocrine tumor cells via both a) the norepinephrine transporter and b) reaction with the integrin αvβ3 receptor.

* * * * *